United States Patent
Shu et al.

(10) Patent No.: US 8,653,037 B2
(45) Date of Patent: Feb. 18, 2014

(54) PROTEINS THAT FLUORESCE AT INFRARED WAVELENGTHS OR GENERATE SINGLET OXYGEN UPON ILLUMINATION

(75) Inventors: Xiaokun Shu, San Diego, CA (US); Antoine Royant, Solana Beach, CA (US); Roger Tsien, La Jolla, CA (US)

(73) Assignees: The Centre National de la Recherche Scientifique, Paris (FR); The Regents of the University of California, Oakland, CA (US)

( * ) Notice: Subject to any disclaimer, the term of this patent is extended or adjusted under 35 U.S.C. 154(b) by 268 days.

(21) Appl. No.: 12/997,548

(22) PCT Filed: Jun. 11, 2009

(86) PCT No.: PCT/US2009/047088
§ 371 (c)(1),
(2), (4) Date: Mar. 23, 2011

(87) PCT Pub. No.: WO2009/152364
PCT Pub. Date: Dec. 17, 2009

(65) Prior Publication Data
US 2011/0177003 A1    Jul. 21, 2011

Related U.S. Application Data

(60) Provisional application No. 61/176,062, filed on May 6, 2009, provisional application No. 61/131,751, filed on Jun. 11, 2008.

(51) Int. Cl.
*A61K 38/16*    (2006.01)

(52) U.S. Cl.
USPC ......... 514/21.2; 435/320.1; 435/29; 530/324; 424/9.6

(58) Field of Classification Search
None
See application file for complete search history.

(56) References Cited

U.S. PATENT DOCUMENTS

2009/0061444 A1    3/2009    Ulijasz et al.

OTHER PUBLICATIONS

Contag, C.H. et al., "Advances in Vivo Bioluminescence Imaging of Gene Expression," *Annu. Rev. Biomed. Eng.*, 2002, vol. 4, pp. 235-260.
Davis, S.J. et al., "Bacteriophytochromes: Phytochrome-Like Photoreceptors from Nonphotosynthetic Eubacteria," *Science*, Dec. 24, 1999, vol. 286, pp. 2517-2520.

(Continued)

*Primary Examiner* — Cecilia J Tsang
*Assistant Examiner* — Randall L Beane
(74) *Attorney, Agent, or Firm* — Morgan, Lewis & Bockius LLP

(57) ABSTRACT

This invention provides novel truncation mutants of a phytochrome from the bacterium *Deinococcus radiodurans*. When expressed either in bacteria or mammalian cells, these mutant phytochromes spontaneously incorporate biliverdin, a ubiquitous intermediate in heme catabolism, and become fluorescent in the infrared (IR) region. These phytochromes are the first genetically encoded labels that can be excited by far-red light and fluorescent in the true IR (>700 nm). If these mutants instead incorporate protoporphyrin IX, an intermediate in heme biosynthesis, illumination now generates significant amounts of singlet oxygen. Singlet oxygen is useful because it can be used to kill individual proteins or cells, detect long-range protein-protein interactions, or generate electron-microscopic contrast. The invention also relates to methods of making and using such proteins and protein variants.

19 Claims, 43 Drawing Sheets

Infrared fluorescent proteins created by structure-based engineering of a bacteriophytochrome.
(A) Fourteen residues surrounding the biliverdin in DrCBD [Protein Data Bank (PDB) ID: 1ztu] were divided into seven groups and targeted for mutagenesis.
(B) Normalized excitation and emission spectra of IFP1.4.

(56) References Cited

OTHER PUBLICATIONS

Fischer, A.J. et al., "Harnessing phytochrome's glowing potential," *PNAS*, Dec. 14, 2004, vol. 101, No. 50, pp. 17334-17339.

Genbank Accession No. AAF12261, White, O. et al., Dec. 28, 2005, 2 pages.

International Search Report mailed on Jan. 27, 2010, for International Application No. PCT/US2009/047088 filed on Jun. 11, 2009, 2 pages.

Jiménez-Banzo, A. et al., "Singlet Oxygen Photosensitization by EGFP and its Chromophore HBDI," *Biophysical Journal*, Jan. 2008, vol. 94, pp. 168-172.

Martin, B.R. et al., "Mammalian cell-based optimization of the biarsenical-binding tetracysteine motif for improved fluorescence and affinity," *Nature Biotechnology Advance Online Publication*, Sep. 11, 2005, pp. 1-7.

Ntziachristos, V. et al., "Visualization of antitumor treatment by means of fluorescence molecular tomography with an annexin V-Cy5.5 conjugate," *PNAS*, Aug. 17, 2004, vol. 101, No. 33, pp. 12294-12299.

Rockwell, N.C. et al., "Phytochome Structure and Signaling Mechanisms," *Annu. Rev. Plant Biol.*, 2006, vol. 57, pp. 837-585.

Rusch, D.B. et al., "The *Sorcerer II* Global Ocean Sampling Expedition: Northwest Atlantic through Eastern Tropical Pacific," *PLoS Biology*, Mar. 2007, vol. 5, No. 3, e77, pp. 0398-0431.

Schroeder, T., "Imaging stem-cell-driven regeneration in mammals," *Nature*, May 15, 2008, vol. 453, pp. 345-351.

Shcherbo, D. et al., "Bright far-red fluorescent protein for whole-body imaging," *Nature Methods*, Sep. 2007, vol. 4, No. 9, pp. 741-746.

Shkrob, M.A. et al., "Far-red fluorescent proteins evolved from a blue chromoprotein from *Actinia equina*," *Biochem. J.*, 2005, vol. 392, pp. 649-654.

Wagner, J.R. et al., "A light-sensing knot revealed by the structure of the chromophore-binding domain of phytochrome," *Nature*, Nov. 17, 2005, vol. 438, pp. 325-331.

Wagner, J.R. et al., "Mutational Analysis of *Deinococcus radiodurans* Bacteriophytochrome Reveals Key Amino Acids Necessary for the Photochromicity and Proton Exchange Cycle of Phytochromes," *The Journal of Biological Chemistry*, May 2, 2008, vol. 283, No. 18, pp. 12212-12226.

Wang, L. et al., "Evolution of new nonantibody proteins via iterative somatic hypermutation," *PNAS*, Nov. 30, 2004, vol. 101, No. 48, pp. 16745-16749.

Weissleder, R. et al., "Imaging in the era of molecular oncology," *Nature*, Apr. 3, 2008, vol. 452, No. 7187, pp. 580-589.

Infrared fluorescent proteins created by structure-based engineering of a bacteriophytochrome. (A) Fourteen residues surrounding the biliverdin in DrCBD [Protein Data Bank (PDB) ID: 1ztu] were divided into seven groups and targeted for mutagenesis. (B) Normalized excitation and emission spectra of IFP1.4.

Fig. 2

| Fluorescent protein | Absorption max. (nm) | Extinct. coeff. (M$^{-1}$cm$^{-1}$) | Emission max. (nm) | Quantum yield | Relative brightness (%) | Stoichiometry |
|---|---|---|---|---|---|---|
| IFP1.0 | 699 | 60,000 | 722 | 0.028 | 100 | Dimer |
| IFP1.1 | 686 | 86,000 | 713 | 0.050 | 256 | Dimer |
| IFP1.2 | 684 | 86,000 | 707 | 0.066 | 338 | Dimer |
| IFP1.3 | 684 | 84,000 | 707 | 0.061 | 305 | Monomer |
| IFP1.4 | 684 | 92,000 | 708 | 0.070 | 383 | Monomer |

Evolution of IFPs showing the mutations introduced at each stage.

Fig. 4 (Sheet 1)

Protein Sequences of IFP1.0, IFP1.01, and IFP1.02 with Engineered His$_6$-Tags

1. DrCBD/D207H (IFP1.0-his6) (SEQ ID NO:2)
MSRDPLPFFPPLYLGGPEITTENCEREPIHIPGSIQPHGALLTADGHSGE
VLQMSLNAATFLGQEPTVLRGQTLAALLPEQWPALQAALPPGCPDALQYR
ATLDWPAAGHLSLTVHRVGELLILEFEPTEAWDSTGPHALRNAMFALESA
PNLRALAEVATQTVRELTGFDRVMLYKFAPDATGEVIAEARREGLHAFLG
HRFPASHIPAQARALYTRHLLRLTADTRAAAVPLDPVLNPQTNAPTPLGG
AVLRATSPMHMQYLRNMGVGSSLSVSVVVGGQLWGLIACHHQTPYVLPPD
LRTTLEYLGRLLSLQVQVKEAEFHHHHHH 2. DrCBD/D207H/I208T/A288V (IFP1.01_his6) (SEQ ID NO:3)
MSRDPLPFFPPLYLGGPEITTENCEREPIHIPGSIQPHGALLTADGHSGE
VLQMSLNAATFLGQEPTVLRGQTLAALLPEQWPALQAALPPGCPDALQYR
ATLDWPAAGHLSLTVHRVGELLILEFEPTEAWDSTGPHALRNAMFALESA
PNLRALAEVATQTVRELTGFDRVMLYKFAPDATGEVIAEARREGLHAFLG
HRFPASHTPAQARALYTRHLLRLTADTRAAAVPLDPVLNPQTNAPTPLGG
AVLRATSPMHMQYLRNMGVGSSLSVSVVVGGQLWGLIVCHHQTPYVLPPD
LRTTLEYLGRLLSLQVQVKEAEFHHHHHH

Fig. 4 (Sheet 2)

3. DrCBD/G119A/V186M/D207H/I208T/A288V (IFP1.02_his6)
(SEQ ID NO:4)

MSRDPLPFFPPLYLGGPEITTENCEREPIHIPGSIQPHGALLTADGHSGE
VLQMSLNAATFLGQEPTVLRGQTLAALLPEQWPALQAALPPGCPDALQYR
ATLDWPAAGHLSLTVHRVAELLILEFEPTEAWDSTGPHALRNAMFALESA
PNLRALAEVATQTVRELTGFDRVMLYKFAPDATGEMIAEARREGLHAFLG
HRFPASHTPAQARALYTRHLLRLTADTRAAAVPLDPVLNPQTNAPTPLGG
AVLRATSPMHMQYLRNMGVGSSLSVSVVVGGQLWGLIVCHHQTPYVLPPD
LRTTLEYLGRLLSLQVQVKEAEFHHHHHH

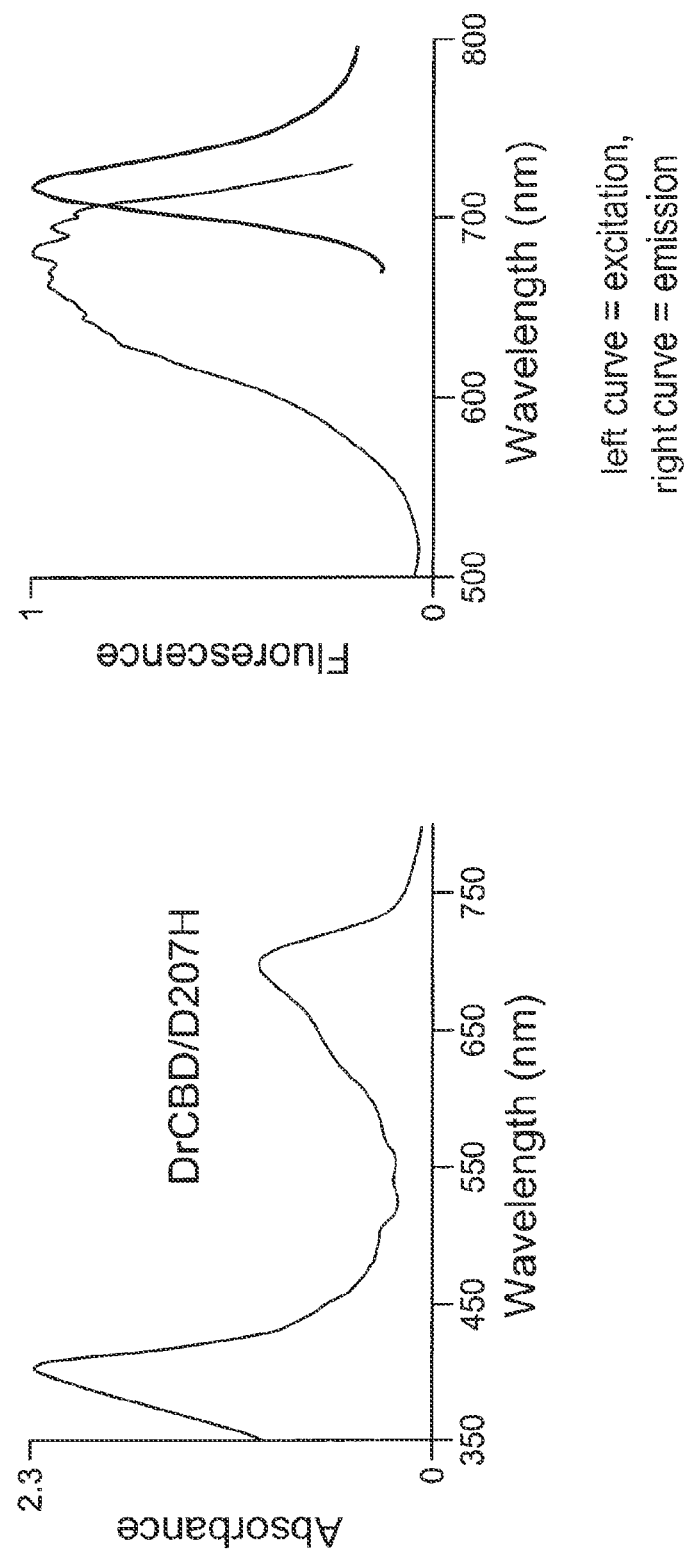
Fig. 5 (Sheet 1)
Absorbance and Fluorescence of IFP1.0, IFP1.01, and IFP1.02
1. DrCBD/D207H = IFP1.0 (QY~0.028, $\lambda_{ex}^{max}$ ~682 nm, $\lambda_{em}^{max}$ ~720 nm)
left curve = excitation, right curve = emission

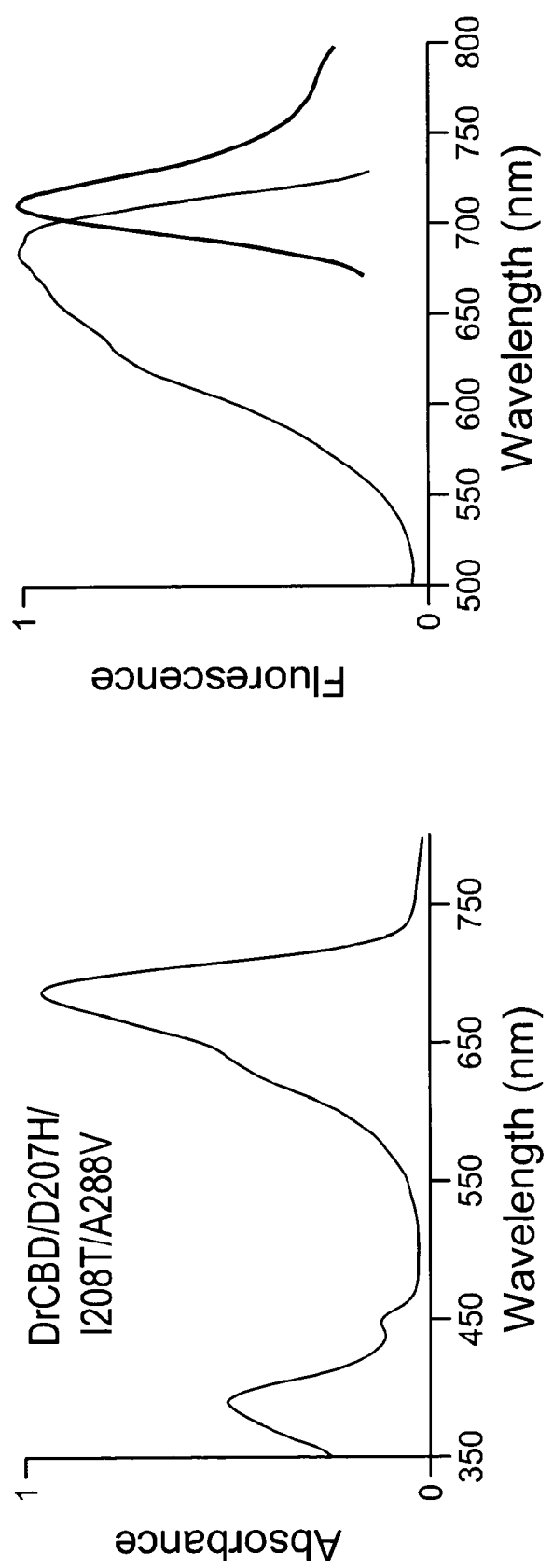
Fig. 5 (Sheet 2)
2. DrCBD/D207H/I208T/A288V = IFP1.01 (QY~0.050, $\lambda_{ex}^{max}$ = 686 nm, $\lambda_{em}^{max}$ = 713 nm)

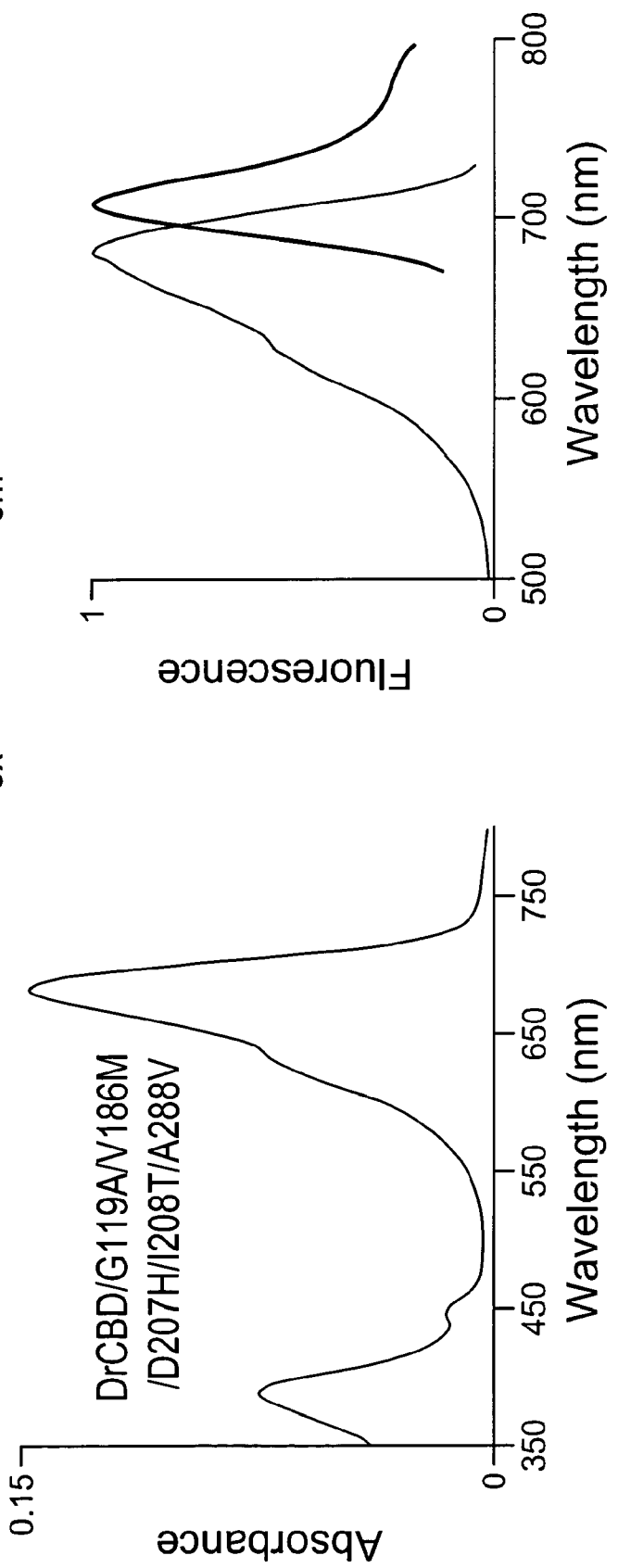
Fig. 5 (Sheet 3)

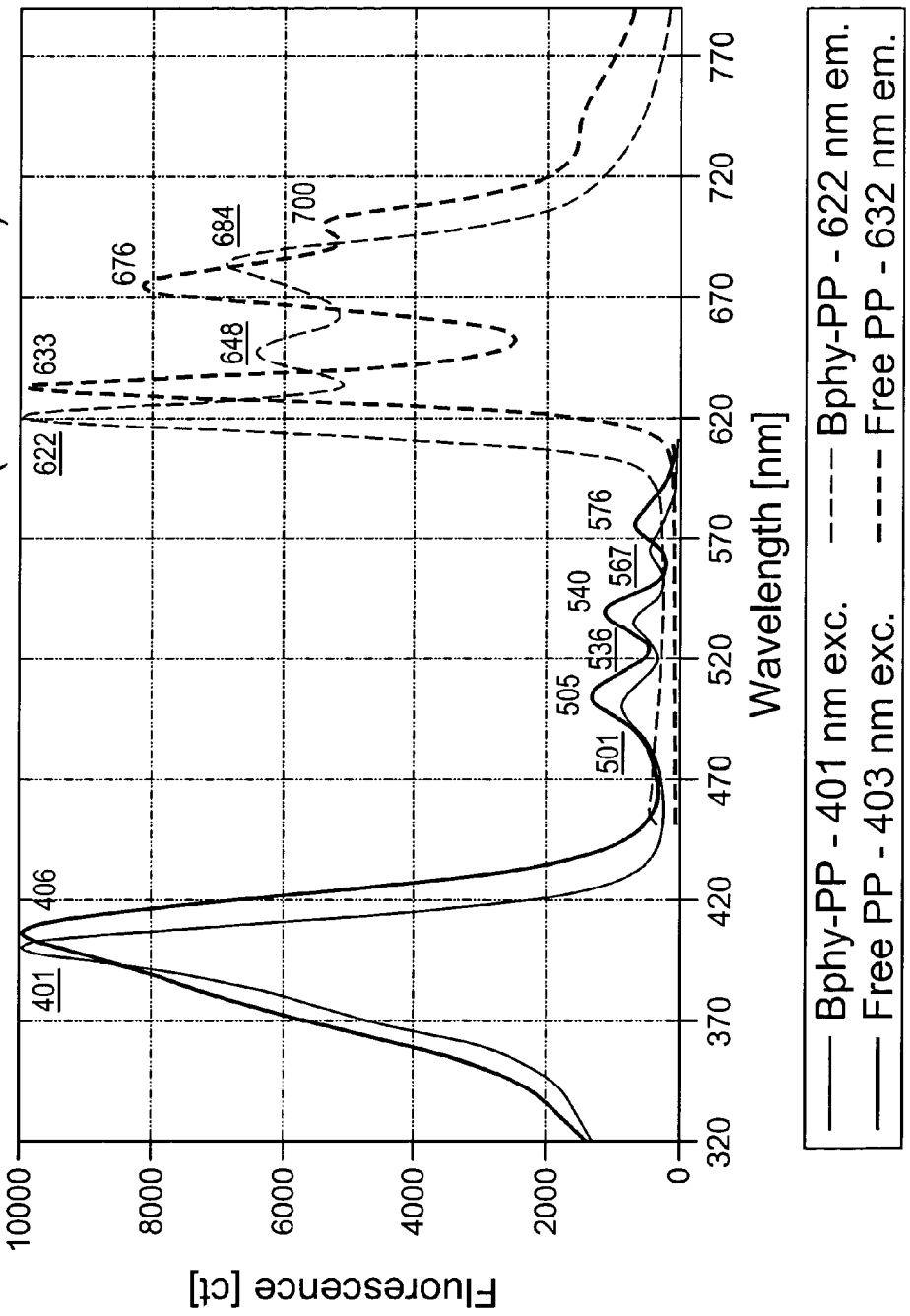

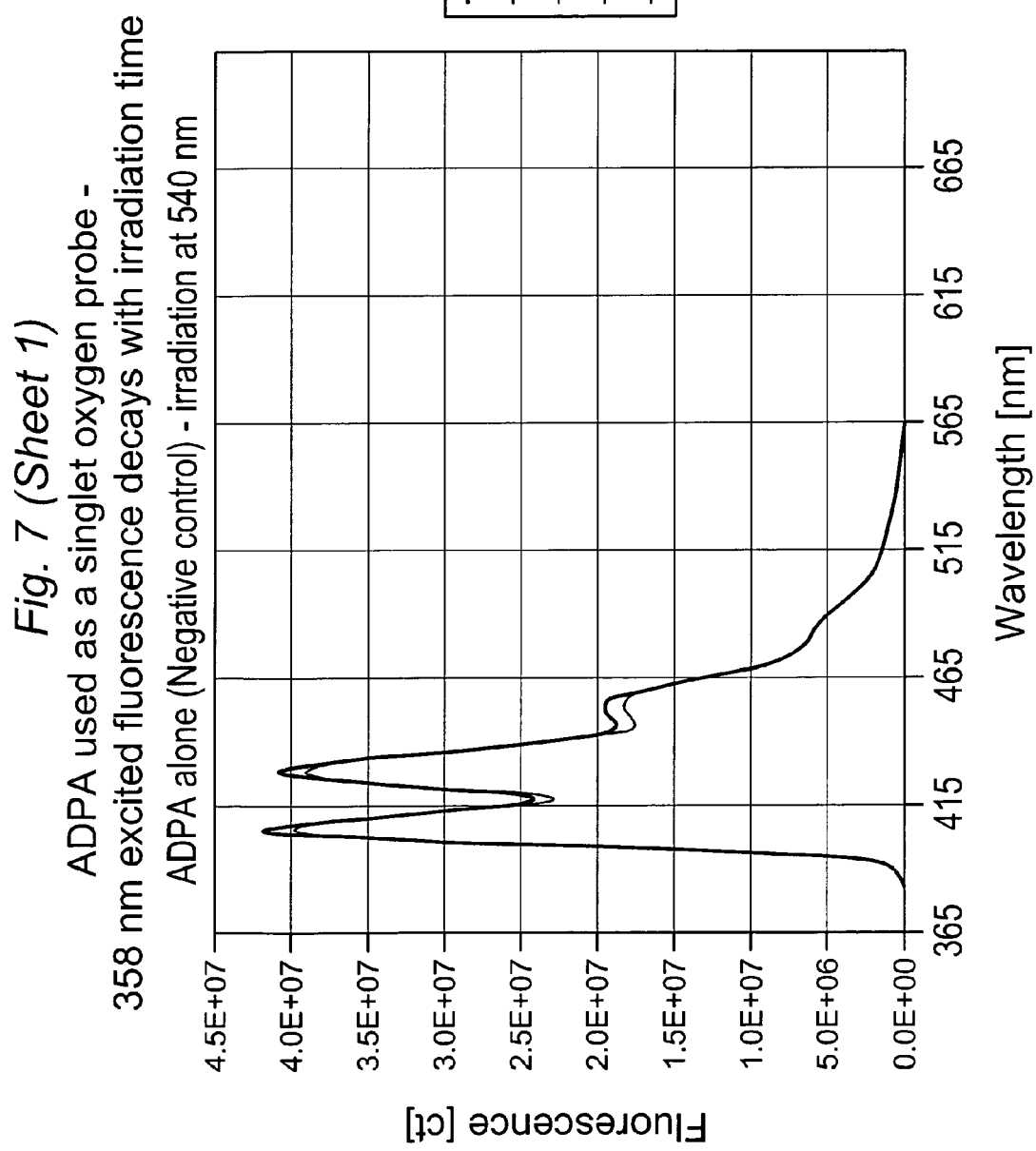

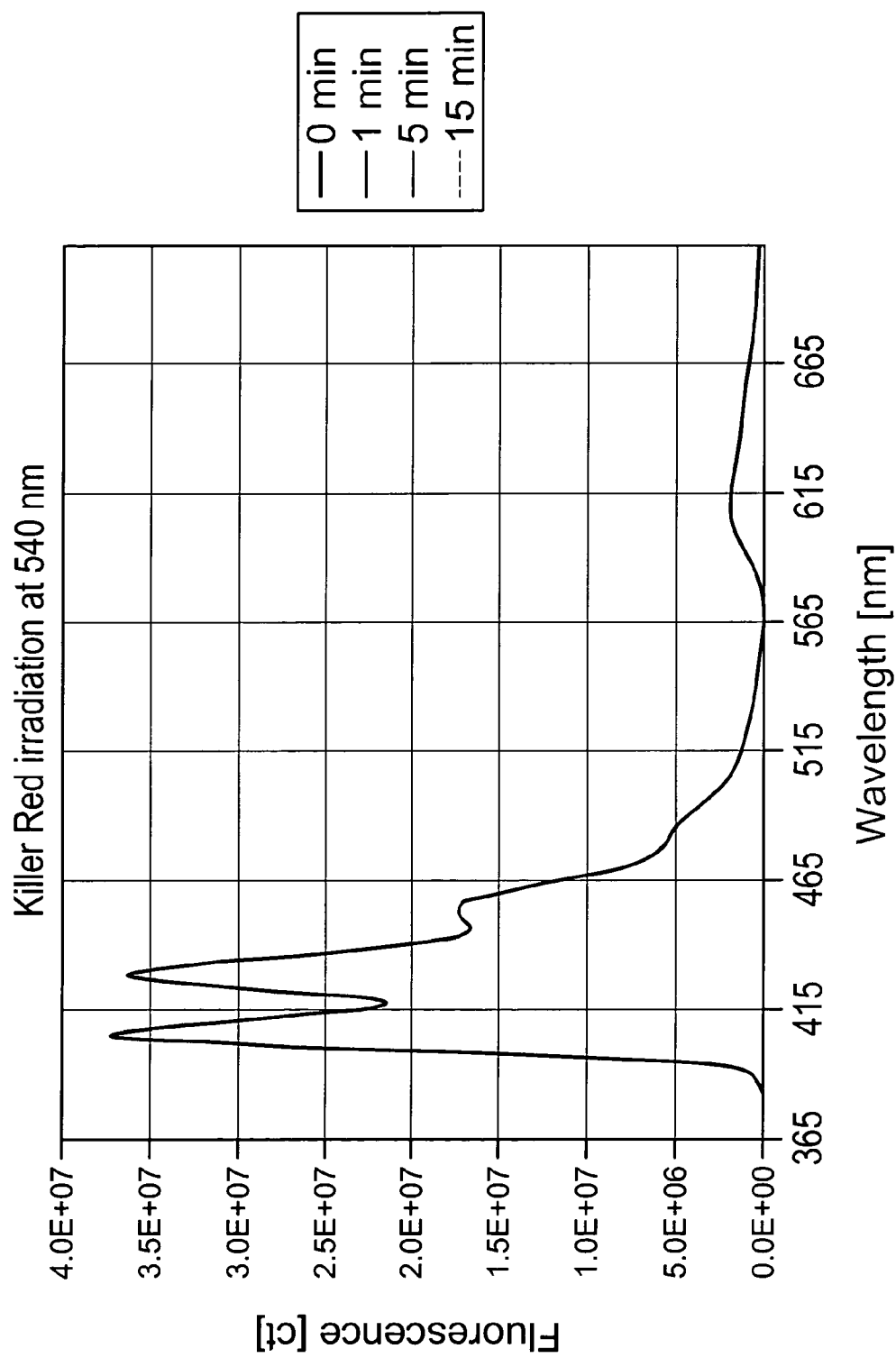

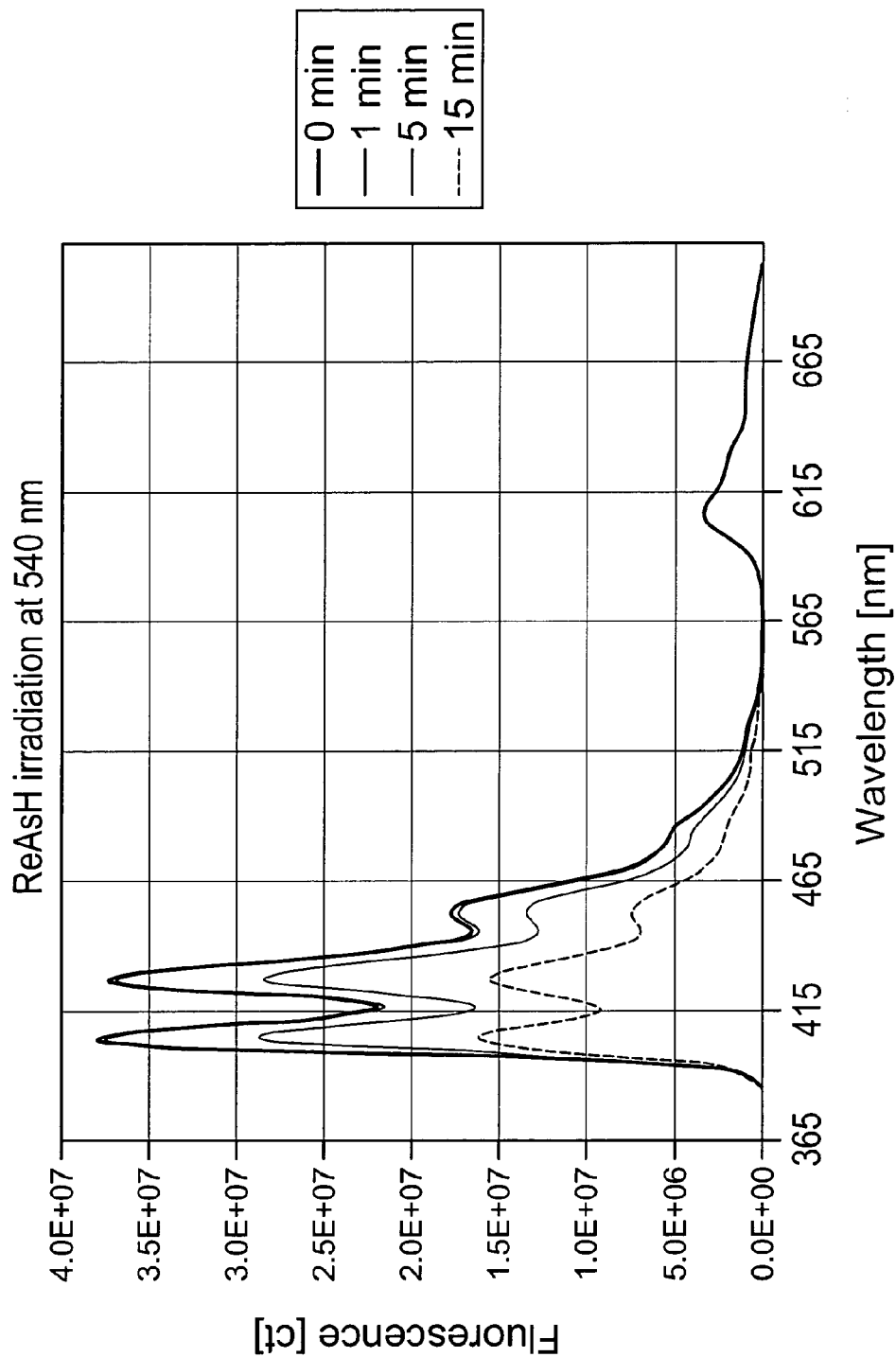
Fig. 7 (Sheet 3)

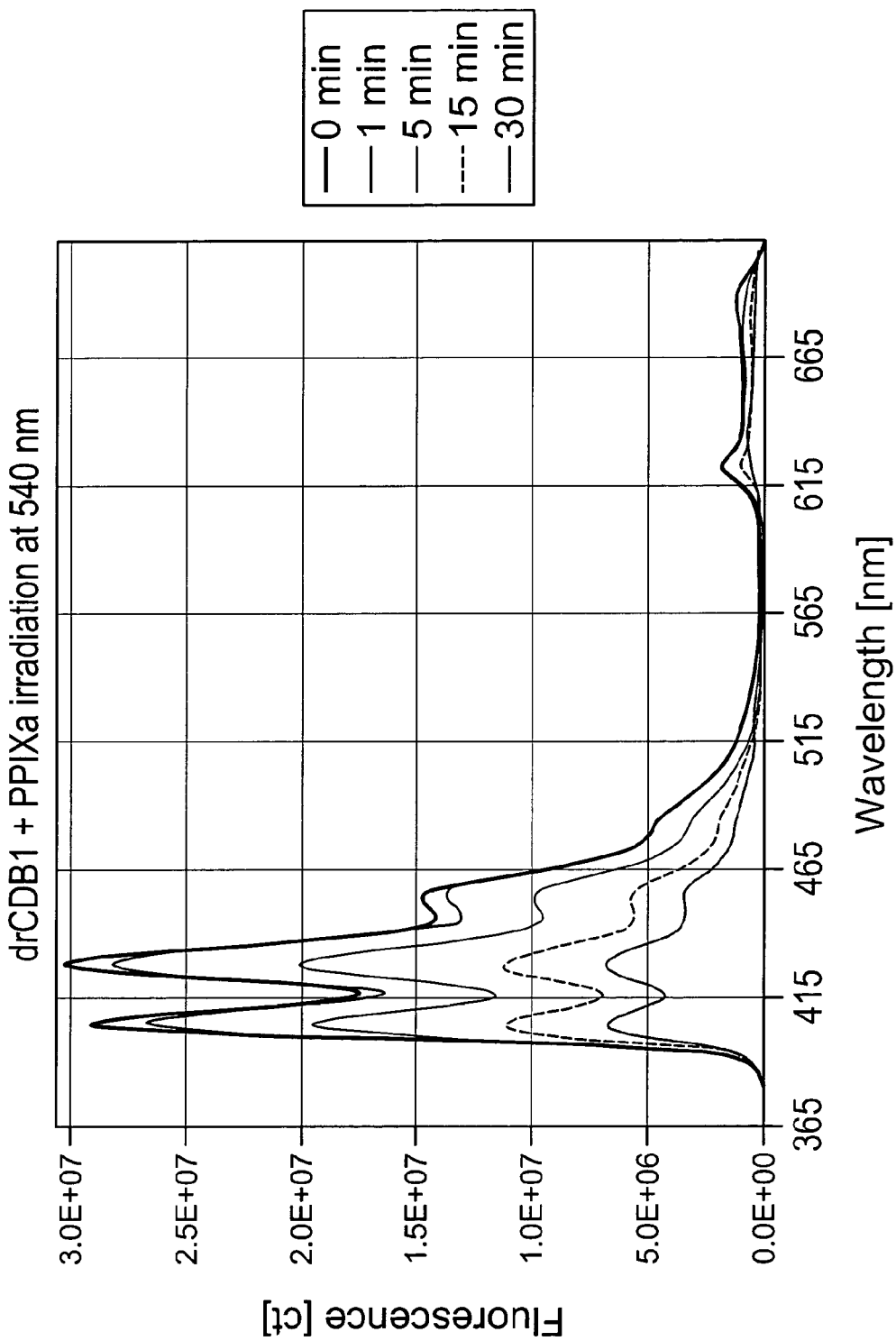
*Fig. 7 (Sheet 4)*

Fig. 8A (Sheet 1)

I. cDNA Sequences for Example 1

1. cDNA of DrCBD/D207H (codon optimized in *E. coli*) (SEQ ID NO:5)

ATGTCTCGTGATCGCTGCCGTGTTTTCCCGCGCTGTATCGGTGGTCCGGAGATCACCAC
TGAAAACTGTGAGCGTGAACCGATTCATATCCGGGTTCCATCCAGCCGCACGGTGCACTGC
TGACCGGCAGATGGCCACTCTGGCGAAGTGCTGCAGATGTCTCTGAACGCTGCAACTTTCCTG
GGTCAGGAGCCGACCGTTCTGCCCGTGGCCAGACCCCTGCGCCGGGTTGCCCGGAACAGTGGCC
GGCTCTGCAGGCGGGCTCTGCAGCTGGTCACCTGTCCCTGACCGTTCACCGGTGAACTGCTGATCCTG
ATTGGCGCGGCAGTGAACGACGAAGCATGGGATGCGCTGACGCACTGTCCTGGTGAACTGCTGATCCTG
GAATTTGAACTGGAATCCGCACCGAACCTGCTGCTCTGCGGAGGTTGCTACTCAGACGCCGTTCGCG
TGCACTGGAATCCGCACCGAACCTGCTGCTCTGCGGAGGTTGCTACTCAGACGCCGTTCGCG
AACTGACTGGTTTGATCGCGTTAATGCTGTCTGCAAGTTCGCACCGGTCACCGTTCCCGGCTAGCCA
ATCGCGGAAGCTCGCGCAGGCTCGCGCACTGTACACTGTCTTTTCTGACCGTGCTGTGCTGACCGTCTGCTGACTGCGGACACCC
CATCCCGCCGCAGCTCGCGCACTGTACACCCGGTCTGCTTGCTGACCGTCTGCTGACTGCGGACACCC
GCGCAGCTGCCGGTTCTGCGGTTCTGCGTGCGGACCAGCCGAACGCCGACCAAGCCCGACCCCGCTG
GGCGGCGGTGGGCGGTCTGCGTGTGCGACCAGCCGCGGTAGTGTGCAGTCTGATCGGTGT
TGGCAGCTCCCTGTCTGTCGAGCGTGGTAGTTGGCCGCCGGATCTGCGCCACCCTGCGCACCCTGTCGTGCTTGTC
ACCACCAGACTCCGTACGTTCTGCGCCGCGGATCTGCGCCACCCTGGAGTACCTGATCGTCGTC
CTGCTGAGCCTGCAGGTACAGGTTAAAGAGGCGAATTCCATCATCACCATCACCAT

*Fig. 8A (Sheet 2)*

2. cDNA of DrCBD/D207H/I208T/A288V (codon optimized in *E. coli*) (SEQ ID NO:6)

ATGTCTCGTGATCCGCTGCCGTTTTTCCCGCCGCTGTATCTGGGTGGTCCGGAGATCACCAC
TGAAAACTGTGAGCGTGAACCGATTCATATCCCGGGTTCCATCCAGCCGCACGGTGCACTGC
TGACCGCAGATGGCCACTCTGGCGAAGTGCTGCAGATGTCTCTGAACGCTGCAACTTTCCTG
GGTCAGGAGCCGACCGTTCTGCGTGGCCAGACCCTGGCGGCTCTGCTGCCGGAACAGTGGCC
GGCTCTGCAGGCGGCTCTGCCGCCGGGTTGCCCGGATGCGCTGCAGTACCGCGCTACCCTGG
ATTGGCCGGCAGCTGGTCACCTGTCCCTGACCGTTCACCGTGTGGGTGAACTGCTGATCCTG
GAATTTGAACCGACCGAAGCATGGGATTCCACCGGCCCGCACGCACTGCGTAACGCTATGTT
TGCACTGGAATCCGCACCGAACCTGCGTGCTCTGGCGGAGGTTGCTACTCAGACCGTTCGCG
AACTGACTGGTTTTGATCGCGTAATGCTGTACAAGTTCGCACCGGATGCGACTGGTGAAGTG
ATCGCGGAAGCTCGTCGCGAAGGTCTGCATGCTTTTCTGGGTCACCGTTTCCCGGCTAGCCA
CACCCCGGCGCAGGCTCGCGCACTGTACACTCGTCACCTGCTGCGTCTGACTGCGGACACCC
GCGCAGCTGCGGTTCCGCTGGACCCGGTTCTGAACCCGCAGACCAACGCGCCGACCCCGCTG
GGCGGCGCGGTTCTGCGTGCGACCAGCCCGATGCATATGCAGTACCTGCGTAACATGGGTGT
TGGCAGCTCCCTGTCTGTGAGCGTGGTAGTTGGCGGTCAGCTGTGGGGTCTGATCGTGTGTC
ACCACCAGACTCCGTACGTTCTGCCGCCGGATCTGCGCACCACCCTGGAGTACCTGGGTCGT
CTGCTGAGCCTGCAGGTACAGGTTAAAGAGGCGGAATTCCATCATCACCATCACCAT

Fig. 8B (Sheet 1)

I. cDNA Sequences for Example 1

3. cDNA of DrCBD/G119A/V186M/D207H/I208T/A288V (codon optimized in *E. coli*) (SEQ ID NO:7)

ATGTCTCGTGATCCGCTGCCGTTTTTCCCGCCGCTGTATCTGGGTGGTCCGGAGATCACCAC
TGAAAACTGTGAGCGTGAACCGATTCATATCCCGGGTTCCATCCAGCCGCACGGTGCACTGC
TGACCGCAGATGGCCACTCTGGCGAAGTGCTGCAGATGTCTCTGAACGCTGCAACTTTCCTG
GGTCAGGAGCCGACCGTTCTGCGTGGCCAGACCCTGGCGGCTCTGCTGCCGGAACAGTGGCC
GGCTCTGCAGGCGGCTCTGCCGCCGGGTTGCCCGGATGCGCTGCAGTACCGCGCTACCCTGG
ATTGGCCGGCAGCTGGTCACCTGTCCCTGACCGTTCACCGTGTGGCTGAACTGCTGATCCTG
GAATTTGAACCGACCGAAGCATGGGATTCCACCGGCCCGCACGCACTGCGTAACGCTATGTT
TGCACTGGAATCCGCACCGAACCTGCGTGCTCTGGCGGAGGTTGCTACTCAGACCGTTCGCG
AACTGACTGGTTTTGATCGCGTAATGCTGTACAAGTTCGCACCGGATGCGACTGGTGAAATG
ATCGCGGAAGCTCGTCGCGAAGGTCTGCATGCTTTTCTGGGTCACCGTTTCCCGGCTAGCCA
CACCCCGGCGCAGGCTCGCGCACTGTACACTCGTCACCTGCTGCGTCTGACTGCGGACACCC
GCGCAGCTGCGGTTCCGCTGGACCCGGTTCTGAACCCGCAGACCAACGCGCCGACCCCGCTG
GGCGGCGCGGTTCTGCGTGCGACCAGCCCGATGCATATGCAGTACCTGCGTAACATGGGTGT
TGGCAGCTCCCTGTCTGTGAGCGTGGTAGTTGGCGGTCAGCTGTGGGGTCTGATCGTGTGTC
ACCACCAGACTCCGTACGTTCTGCCGCCGGATCTGCGCACCACCCTGGAGTACCTGGGTCGT
CTGCTGAGCCTGCAGGTACAGGTTAAAGAGGCGGAATTCCATCATCACCATCACCAT

Fig. 8B (Sheet 2)

4. cDNA of DrCBD/D207H (codon optimized for mammals) (SEQ ID NO:8)
ATGAGCCGGGACCCTCTGCCATTCTTTCCACCTCTGTACCTGGGCGGCCTGAGATTACAAC
CGAGAACTGCGAGAGAGAGCCTATCCACATTCCTGGGTCCATCCAGCCACACGGGGCTCTGC
TCACAGCTGACGCTGACGGCCACTCCGGAGAGGTGCTCCAAATGTCCCTGGCTACCTTCCTG
GGCCAGGAGCCTACTGTGCTGCGGGGCCCCCAGGATGTCCAGAGCAGTGGCC
AGCCCTGCAGGCAGCCCTGCCCCCAGGATGTCCAGATGCCCCTCCAATACAGGCCACCCTCG
ACTGGCCAGCTGCTGGGCACCTCAGCTGTGACCTGACTGTGCATCGGGTGGGGAACTCCTGATCCTG
GAGTTCGAACTACCGAGGCCTGGGACAGAGCCCTACGCTGGCCTGAGGAACGCCATGTT
TGCTCTGGAAAGCGCTCCAAACTGCGGGCTCTGGCCGAAGTCGCAACACAAAACTGTGAGAG
AACTGACTGGCTTCGATCGGGTGATGCTGTACAAATTGCCCCTGACGCCACTGGAGAGGTG
ATTGGTGAGGCCAGACGGGAGAGGCCCTTTCTGGGGCCACAGGTTTCCCGCATCCCA
CATCCCTGCACACAAGTAGGCCCCCTTCCACACAAGACACCTGTCCGGCTGACCGCAGACACCA
GGGCTGCAGCAGTGCCCCTGACCCGTGCTGAATCCCCAGACAAATGCTCCTACACCTCTG
GGCGGAGCTGTGTCCTCAGAGCTACATCCGCCAGATCAGTACCTGAGGAATATGGGAGT
GGGCTCCTCCCTGAGCGTCAGCGTCGTGGCCACCAGAGCTGTGGGGACTGATTGCCTGCC
ACCATCAGACACCCTACGTGCTGCCACCAGATCTGCGGACCACCCTGGAGTATCTGGGGAGG
CTCGTGTCCCTGAGCCATGCATCTAGAGGCCAGGTGCAGGTGAAAGAGCCGAATTCTGCAGATATCCATCACACTGGCG
GCCGCTCGAGCTCGAGCATGCATCTAGAGGCCCTATTCTTTATAGTGTCACCTAAATGC

*Fig. 8C (Sheet 1)*

I. cDNA Sequences for Example 1

5. cDNA of DrCBD/D207H/I208T/A288V (codon optimized for mammals) (SEQ ID NO:9)

ATGAGCCGGGACCCTCTGCCATTCTTTCCACCTCTGTACCTGGGCGGCCCTGAGATTACAAC
CGAGAACTGCGAGAGAGAGCCTATCCACATTCCTGGGTCCATCCAGCCACACGGGGCTCTGC
TCACAGCTGACGGCCACTCCGGAGAGGTGCTCCAAATGTCCCTGAATGCCGCTACCTTCCTG
GGCCAGGAGCCTACTGTGCTGCGGGGGCAGACCCTGGCTGCCCTGCTCCCCGAGCAGTGGCC
AGCCCTGCAGGCAGCCCTGCCCCCAGGATGTCCAGATGCCCTCCAATACAGGGCCACCCTCG
ACTGGCCAGCTGCTGGGCACCTCAGCCTGACTGTGCATCGGGTGGGGGAACTCCTGATCCTG
GAGTTCGAACCTACCGAGGCCTGGGACAGCACTGGCCCTCACGCCCTGAGGAACGCCATGTT
TGCTCTGGAAAGCGCTCCAAACCTGCGGGCTCTGGCCGAAGTCGCAACACAAACTGTGAGAG
AACTGACTGGCTTCGATCGGGTGATGCTGTACAAATTTGCCCCTGACGCCACTGGAGAGGTG
ATTGCTGAGGCCAGACGGGAGGGCCTCCACGCTTTTCTGGGCCACAGGTTTCCCGCATCCCA
CACCCCTGCACAAGCTAGGGCCCTCTACACAAGACACCTGCTCCGGCTGACCGCAGACACCA
GGGCTGCAGCAGTGCCCCTCGACCCCGTGCTGAATCCCCAGACAAATGCTCCTACACCTCTG
GGCGGAGCTGTCCTCAGAGCTACATCCCCAATGCACATGCAGTACCTGAGGAATATGGGAGT
GGGCTCCTCCCTGAGCGTCAGCGTCGTGGTCGGCGGCCAGCTGTGGGGACTGATTGTCTGCC
ACCATCAGACACCCTACGTGCTGCCACCAGATCTGCGGACCACCCTGGAGTATCTGGGGAGG
CTCCTGTCCCTGCAGGTGCAGGTGAAAGAAGCC

*Fig. 8C (Sheet 2)*

6. cDNA of DrCBD/G119A/V186M/D207H/I208T/A288V (codon optimized for mammals) (SEQ ID NO:10)

ATGAGCCGGGACCCTCTGCCATTCTTTCCACCTCTGTACCTGGGCGGCCCTGAGATTACAAC
CGAGAACTGCGAGAGAGAGCCTATCCACATTCCTGGGTCCATCCAGCCACACGGGGCTCTGC
TCACAGCTGACGGCCACTCCGGAGAGGTGCTCCAAATGTCCCTGAATGCCGCTACCTTCCTG
GGCCAGGAGCCTACTGTGCTGCGGGGGCAGACCCTGGCTGCCCTGCTCCCCGAGCAGTGGCC
AGCCCTGCAGGCAGCCCTGCCCCCAGGATGTCCAGATGCCCTCCAATACAGGGCCACCCTCG
ACTGGCCAGCTGCTGGGCACCTCAGCCTGACTGTGCATCGGGTGGCGGAACTCCTGATCCTG
GAGTTCGAACCTACCGAGGCCTGGGACAGCACTGGCCCTCACGCCCTGAGGAACGCCATGTT
TGCTCTGGAAAGCGCTCCAAACCTGCGGGCTCTGGCCGAAGTCGCAACACAAACTGTGAGAG
AACTGACTGGCTTCGATCGGGTGATGCTGTACAAATTTGCCCCTGACGCCACTGGAGAGATG
ATTGCTGAGGCCAGACGGGAGGGCCTCCACGCTTTTCTGGGCCACAGGTTTCCCGCATCCCA
CACCCCTGCACAAGCTAGGGCCCTCTACACAAGACACCTGCTCCGGCTGACCGCAGACACCA
GGGCTGCAGCAGTGCCCCTCGACCCCGTGCTGAATCCCCAGACAAATGCTCCTACACCTCTG
GGCGGAGCTGTCCTCAGAGCTACATCCCCAATGCACATGCAGTACCTGAGGAATATGGGAGT
GGGCTCCTCCCTGAGCGTCAGCGTCGTGGTCGGCGGCCAGCTGTGGGGACTGATTGTCTGCC
ACCATCAGACACCCTACGTGCTGCCACCAGATCTGCGGACCACCCTGGAGTATCTGGGGAGG
CTCCTGTCCCTGCAGGTGCAGGTGAAAGAAGCC

Fig. 9A (Sheet 1)

II. Protein Sequences for Example 1

1. DrCBD/D207H (with hexahistidine tag for purification)(SEQ ID NO:2)

MSRDPLPFFPPLYLGGPEITTENCEREPIHIPGSIQPHGALLTADGHSGEVLQMSLNAATFL
GQEPTVLRGQTLAALLPEQWPALQAALPPGCPDALQYRATLDWPAAGHLSLTVHRVGELLIL
EFEPTEAWDSTGPHALRNAMFALESAPNLRALAEVATQTVRELTGFDRVMLYKFAPDATGEV
IAEARREGLHAFLGHRFPASHIPAQARALYTRHLLRLTADTRAAAVPLDPVLNPQTNAPTPL
GGAVLRATSPMHMQYLRNMGVGSSLSVSVVVGGQLWGLIACHHQTPYVLPPDLRTTLEYLGR
LLSLQVQVKEAEFHHHHHH

2. DrCBD/D207H/I208T/A288V (with hexahistidine tag for purification) (SEQ ID No:3)

MSRDPLPFFPPLYLGGPEITTENCEREPIHIPGSIQPHGALLTADGHSGEVLQMSLNAATFL
GQEPTVLRGQTLAALLPEQWPALQAALPPGCPDALQYRATLDWPAAGHLSLTVHRVGELLIL
EFEPTEAWDSTGPHALRNAMFALESAPNLRALAEVATQTVRELTGFDRVMLYKFAPDATGEV
IAEARREGLHAFLGHRFPASHTPAQARALYTRHLLRLTADTRAAAVPLDPVLNPQTNAPTPL
GGAVLRATSPMHMQYLRNMGVGSSLSVSVVVGGQLWGLIVCHHQTPYVLPPDLRTTLEYLGR
LLSLQVQVKEAEFHHHHHH

Fig. 9A (Sheet 2)

3. DrCBD/G119A/V186M/D207H/I208T/A288V (with hexahistidine tag for purification) (SEQ ID NO:4)

MSRDPLPFFPPLYLGGPEITTENCEREPIHIPGSIQPHGALLTADGHSGEVLQMSLNAATFL
GQEPTVLRGQTLAALLPEQWPALQAALPPGCPDALQYRATLDWPAAGHLSLTVHRVAELLIL
EFEPTEAWDSTGPHALRNAMFALESAPNLRALAEVATQTVRELTGFDRVMLYKFAPDATGEM
IAEARREGLHAFLGHRFPASHTPAQARALYTRHLLRLTADTRAAAVPLDPVLNPQTNAPTPL
GGAVLRATSPMHMQYLRNMGVGSSLSVSVVVGGQLWGLIVCHHQTPYVLPPDLRTTLEYLGR
LLSLQVQVKEAEFHHHHHH

4. DrCBD/D207H (with C-terminal extension from pcDNA3 vector) (SEQ ID NO:11)

MSRDPLPFFPPLYLGGPEITTENCEREPIHIPGSIQPHGALLTADGHSGEVLQMSLNAATFL
GQEPTVLRGQTLAALLPEQWPALQAALPPGCPDALQYRATLDWPAAGHLSLTVHRVGELLIL
EFEPTEAWDSTGPHALRNAMFALESAPNLRALAEVATQTVRELTGFDRVMLYKFAPDATGEV
IAEARREGLHAFLGHRFPASHIPAQARALYTRHLLRLTADTRAAAVPLDPVLNPQTNAPTPL
GGAVLRATSPMHMQYLRNMGVGSSLSVSVVVGGQLWGLIACHHQTPYVLPPDLRTTLEYLGR
LLSLQVQVKEAEFCRYPSHWRPLEHASRGPYSIVSPKC

Fig. 9B

II. Protein Sequences for Example 1

5. DrCBD/D207H/I208T/A288V (SEQ ID NO:12)

MSRDPLPFFPPLYLGGPEITTENCEREPIHIPGSIQPHGALLTADGHSGEVLQMSLNAATFL
GQEPTVLRGQTLAALLPEQWPALQAALPPGCPDALQYRATLDWPAAGHLSLTVHRVGELLIL
EFEPTEAWDSTGPHALRNAMFALESAPNLRALAEVATQTVRELTGFDRVMLYKFAPDATGEV
IAEARREGLHAFLGHRFPASHTPAQARALYTRHLLRLTADTRAAAVPLDPVLNPQTNAPTPL
GGAVLRATSPMHMQYLRNMGVGSSLSVSVVVGGQLWGLIVCHHQTPYVLPPDLRTTLEYLGR
LLSLQVQVKEA

6. DrCBD/G119A/V186M/D207H/I208T/A288V (SEQ ID NO:13)

MSRDPLPFFPPLYLGGPEITTENCEREPIHIPGSIQPHGALLTADGHSGEVLQMSLNAATFL
GQEPTVLRGQTLAALLPEQWPALQAALPPGCPDALQYRATLDWPAAGHLSLTVHRVAELLIL
EFEPTEAWDSTGPHALRNAMFALESAPNLRALAEVATQTVRELTGFDRVMLYKFAPDATGEM
IAEARREGLHAFLGHRFPASHTPAQARALYTRHLLRLTADTRAAAVPLDPVLNPQTNAPTPL
GGAVLRATSPMHMQYLRNMGVGSSLSVSVVVGGQLWGLIVCHHQTPYVLPPDLRTTLEYLGR
LLSLQVQVKEA

Dark and light adapted behavior of IFP1.0 and IFP1.4. Absorbance spectra at different time points were taken in the dark (0 - 30 min.), upon 615 nm light illumination by solar simulator (30 - 40 min.), and then in the dark again (40 - 70 min.).

Size exclusion chromatography of IFP1.0 and 1.4. Three standards are also shown: γ-globulin (158 kDa), ovalbumin (44 kDa) and myoglobin (17 kDa). Absorbance was measured at 280 nm.

IFP monomerization by L311K mutation. (A) The dimer interface in DrCBD is formed from 4 residues (Y307/L311/L314/V318). (B) Size exclusion chromatography of IFP1.2, 1.3, 1.4 and a mixture of IFP1.2 and 1.3.

Fig. 13

Sequence Alignment of IFP1.4_S2A_his6 with DrCBD

```
DrCBD  (SEQ ID NO:14)
       MSRDPLPFFPPLYLGGPETTTENCEREPIHIPGSIQPHGALLTADGHSGEVLQMSLNAAT  60
IFP1.4 (SEQ ID NO:15)
       MARDPLPFFPPLYLGGPETTTENCEREPIHIPGSIQPHGALLTADGHSGEVLQVSLNAAT  60
DrCBD  FLGQEPTVLRGQTLAALLPEQWPALQAALPPGCPDALQYRATLDWPAAGHLSLTVHRVGE  120
IFP1.4 FLGQEPTVLRGQTLAALLPEQWPALQAALPPGCPDALQYRATLDWPAAGHLSLTVHRVAE  120
DrCBD  LLILEFEPTEAWDSTGPHALRNAMFALESAPNLRALAEVATQTVRELTGFDRVMLYKFAP  180
IFP1.4 LLILEFEPTEAWDSIGPHALRNAMFALESAPNLRALAEVATQTVRELTGFDRVMLYKFAP  180
DrCBD  DATGEVIAEARREGLHAFLGHRFPASDIPAQARALYTRHLLRLTADTRAAAVPLDPVLNP  240
IFP1.4 DATGEMIAEARREGMQAFLGHRFPASHTPAQARALYTRHLLRLTADTRAAAVPLDPVLNP  240
DrCBD  QTNAPTPLGGAVLRATSPMHMQYLRNMGVGSSLSVSVVVGGQLWGLIACHHQTPYVLPPD  300
IFP1.4 QTNAPTPLGGAVLRATSPMHMQYLRNMGVGSSLSVSVVVGGQLWGLIVCHHQTPYVLPPD  300
DrCBD  LRTTLEYLGRLLSLQVQVKEA                                         321
IFP1.4 LRTTLEELGRKLSGQVQRKEAEFHHHHHH                                 329
```

A sequence alignment of IFP1.4_S2A_His6 with DrCBD is shown with internal mutations. The S2A mutation is to optimize the Kozak sequence when expressed in mammalian cells, and the C-terminal hexahistidine motif is to enable immobilized metal ion affinity chromatography.

pH dependence of IFP1.4 fluorescence. IFP1.4 was excited at 640 nm and its emission at 700 - 800 nm was integrated, normalized and plotted against pH.

Fig. 15

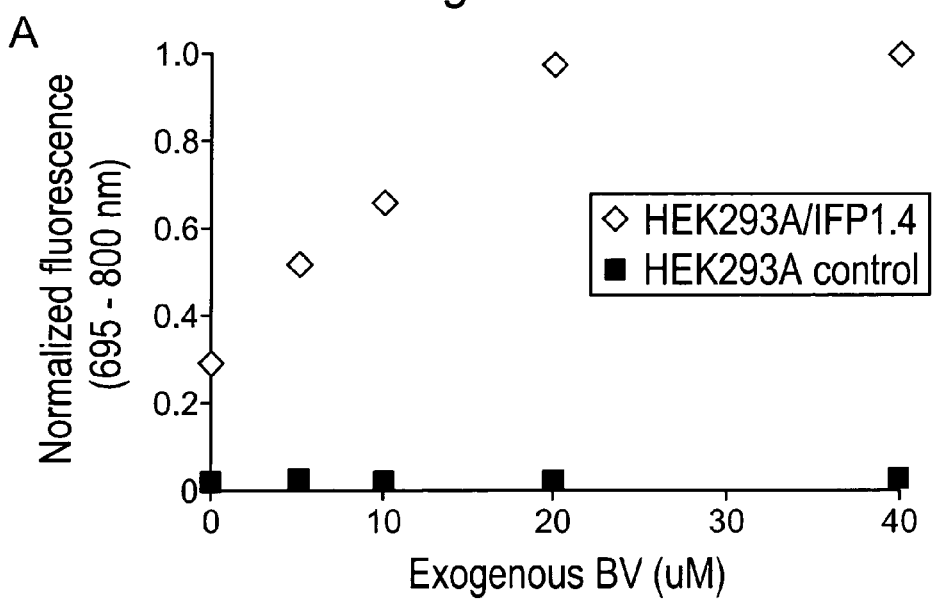

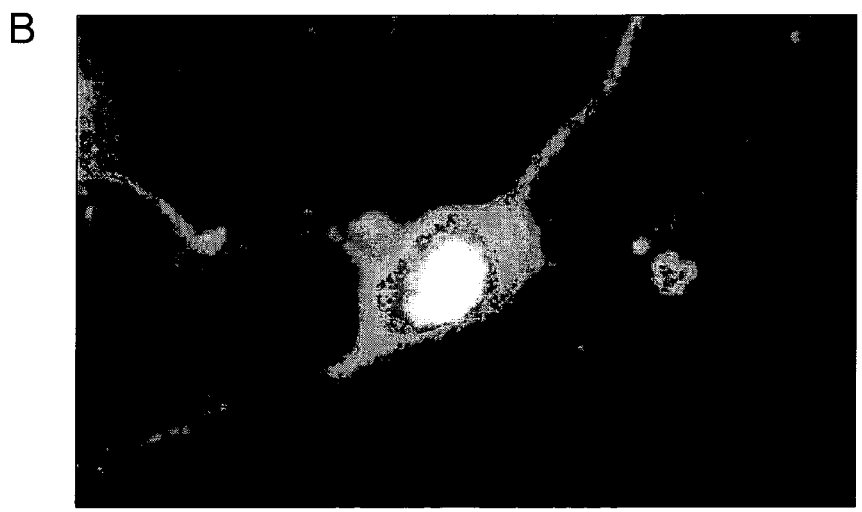

Increase of IFP fluorescence by addition of exogenous BV. (A) IFP1.4-transfected HEK293A cells indicated increase of fluorescence upon addition of exogenous BV, with untransfected cells as the control. IFP fluorescence was integrated from 695 to 800 nm upon excitation at 660 nm. (B) Fluorescence image of a P2 cultured cortical neuron 2 weeks after transfection of IFP1.1, 10 minutes after addition of 25 uM BV.

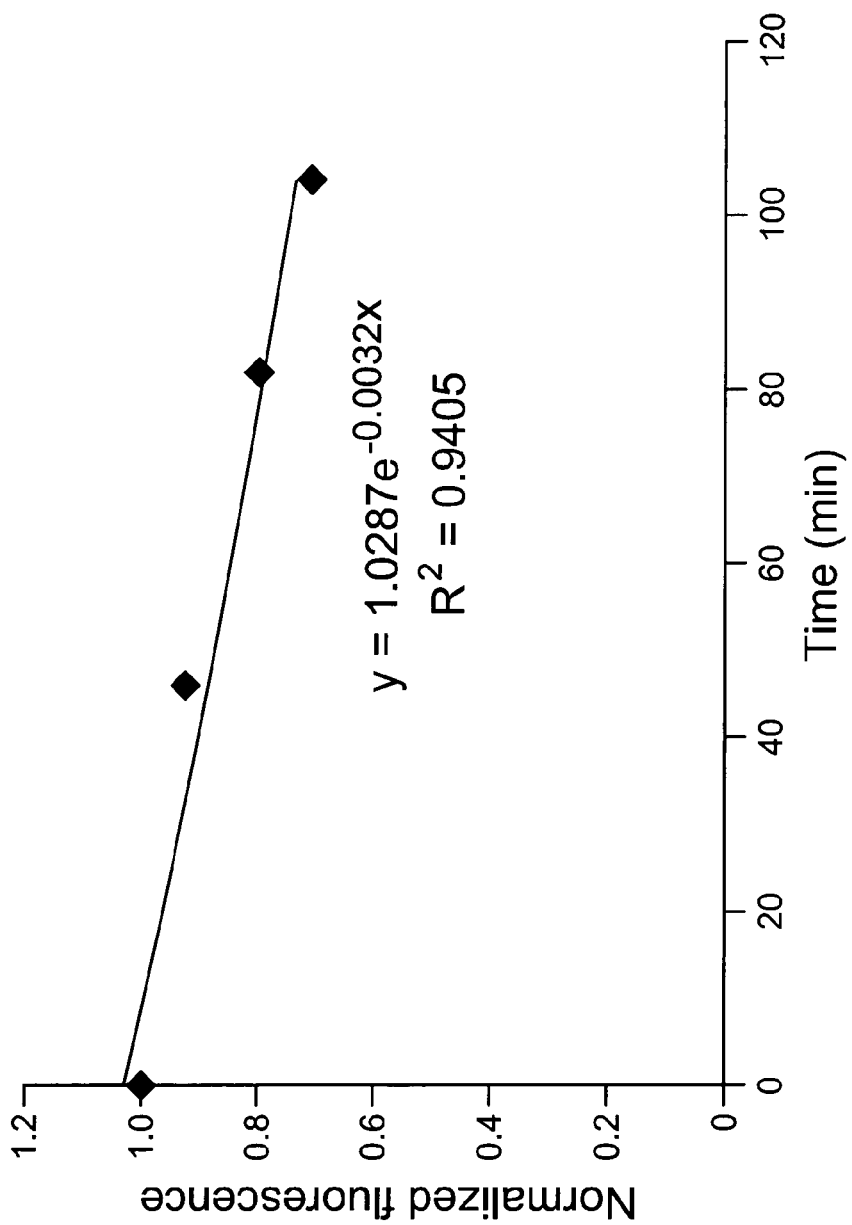

Fig. 18 (Sheet 1)

>SEQ ID NO:14 - DrCDB
MSRDPLPFFPPLYLGGPEITTENCEREPIHIPGSIQPHGALLTADGHSGEVLQMSLNAATFLGQEPTVLRGQTLA
ALLPEQWPALQAALPPGCPDALQYRATLDWPAAGHLSLTVHRVGELLILEFEPTEAWDSTGPHALRNAMFALESA
PNLRALAEVATQTVRELTGFDRVMLYKFAPDATGEVIAEARREGLHAFLGHRFPASDIPAQARALYTRHLLRLTA
DTRAAAVPLDPVLNPQTNAPTPLGGAVLRATSPMHMQYLRNMGVGSSLSVSVVGGQLWGLIACHHQTPYVLPPD
LRTTLEYLGRLLSLQVQVKEA

>SEQ ID NO:16 - IFP1.0
MSRDPLPFFPPLYLGGPEITTENCEREPIHIPGSIQPHGALLTADGHSGEVLQMSLNAATFLGQEPTVLRGQTLA
ALLPEQWPALQAALPPGCPDALQYRATLDWPAAGHLSLTVHRVGELLILEFEPTEAWDSTGPHALRNAMFALESA
PNLRALAEVATQTVRELTGFDRVMLYKFAPDATGEVIAEARREGLHAFLGHRFPASHIPAQARALYTRHLLRLTA
DTRAAAVPLDPVLNPQTNAPTPLGGAVLRATSPMHMQYLRNMGVGSSLSVSVVGGQLWGLIACHHQTPYVLPPD
LRTTLEYLGRLLSLQVQVKEA

>SEQ ID NO:17 - IFP1.1
MSRDPLPFFPPLYLGGPEITTENCEREPIHIPGSIQPHGALLTADGHSGEVLQMSLNAATFLGQEPTVLRGQTLA
ALLPEQWPALQAALPPGCPDALQYRATLDWPAAGHLSLTVHRVGELLILEFEPTEAWDSTGPHALRNAMFALESA
PNLRALAEVATQTVRELTGFDRVMLYKFAPDATGEMIAEARREGLHAFLGHRFPASHTPAQARALYTRHLLRLTA
DTRAAAVPLDPVLNPQTNAPTPLGAVLRATSPMHMQYLRNMGVGSSLSVSVVGGQLWGLIVCHHQTPYVLPPD
LRTTLEYLGRLLSLQVQVKEA

Fig. 18 (Sheet 2)

>SEQ ID NO:18 - IFP1.2
MSRDPLPFFPPLYLGGPEITTENCEREPIHIPGSIQPHGALLTADGHSGEVLQVSLNAATFLGQEPTVLRGQTLA
ALLPEQWPALQAALPPGCPDALQYRATLDWPAAGHLSLTVHRVGELLILEFEPTEAWDSTGPHALRNAMFALESA
PNLRALAEVATQTVRELTGFDRVMLYKFAPDATGEMIAEARREGLHAFLGHRFPASHTPAQARALYTRHLLRLTA
DTRAAAVPLDPVLNPQTNAPTPLGGAVLRATSPMHMQYLRNMGVGSSLSVSVVGGQLWGLIVCHHQTPYVLPPD
LRTTLEYLGRLLSLQVQVKEA

>SEQ ID NO:19 - IFP1.3
MSRDPLPFFPPLYLGGPEITTENCEREPIHIPGSIQPHGALLTADGHSGEVLQVSLNAATFLGQEPTVLRGQTLA
ALLPEQWPALQAALPPGCPDALQYRATLDWPAAGHLSLTVHRVGELLILEFEPTEAWDSTGPHALRNAMFALESA
PNLRALAEVATQTVRELTGFDRVMLYKFAPDATGEMIAEARREGLHAFLGHRFPASHTPAQARALYTRHLLRLTA
DTRAAAVPLDPVLNPQTNAPTPLGGAVLRATSPMHMQYLRNMGVGSSLSVSVVGGQLWGLIVCHHQTPYVLPPD
LRTTLEYLGRKLSLQVQVKEA

>SEQ ID NO:20 - IFP1.4
MSRDPLPFFPPLYLGGPEITTENCEREPIHIPGSIQPHGALLTADGHSGEVLQVSLNAATFLGQEPTVLRGQTLA
ALLPEQWPALQAALPPGCPDALQYRATLDWPAAGHLSLTVHRVAELLILEFEPTEAWDSIGPHALRNAMFALESA
PNLRALAEVATQTVRELTGFDRVMLYKFAPDATGEMIAEARREGMQAFLGHRFPASHTPAQARALYTRHLLRLTA
DTRAAAVPLDPVLNPQTNAPTPLGGAVLRATSPMHMQYLRNMGVGSSLSVSVVGGQLWGLIVCHHQTPYVLPPD
LRTTLEELGRKLSGQVQRKEA

Imaging of IFP1.4 and IFP1.4-PHAKT1 in HEK293A cells.
(A) Fluorescence image of IFP1.4 taken with Cy5.5 filter
set (665 T 22.5 nm excitation, 725 T 25 nm emission)
with and without differential interference contrast (DIC).
(B) confocal laser-scanning microscopy of
IFP1.4-PHAKT1 before and after insulin stimulation
(excitation by 635-nm laser, emission by 650-nm
long-pass filter).

Fig. 20 (Sheet 1)

Imaging of GFP, mKate, and IFP1.1 in living mice.

(A) Liver fluorescence of living mice injected with Ad5I (top row) and Ad5K (bottom row), imaged in the IFP excitation and emission channel before and after BV administration, mKate channel before and after BV, and GFP channel. Images through the mKate channel have been 5°- brightened in software to render them visible, so the relative gains of the IFP channel, mKate channel, and GFP channel were 1, 5, and 1, respectively. Arrows point to the liver. Note that the GFP images are dominated by autofluorescence, which renders the livers invisible.

(B) Time course of averaged and normalized Ad5I liver fluorescence before and after BV injection.

(C) Images of IFP-expressing mouse showing spectrally deconvoluted liver fluorescence (left) and its overlay (right) with autofluorescence.

Fig. 20 (Sheet 2)
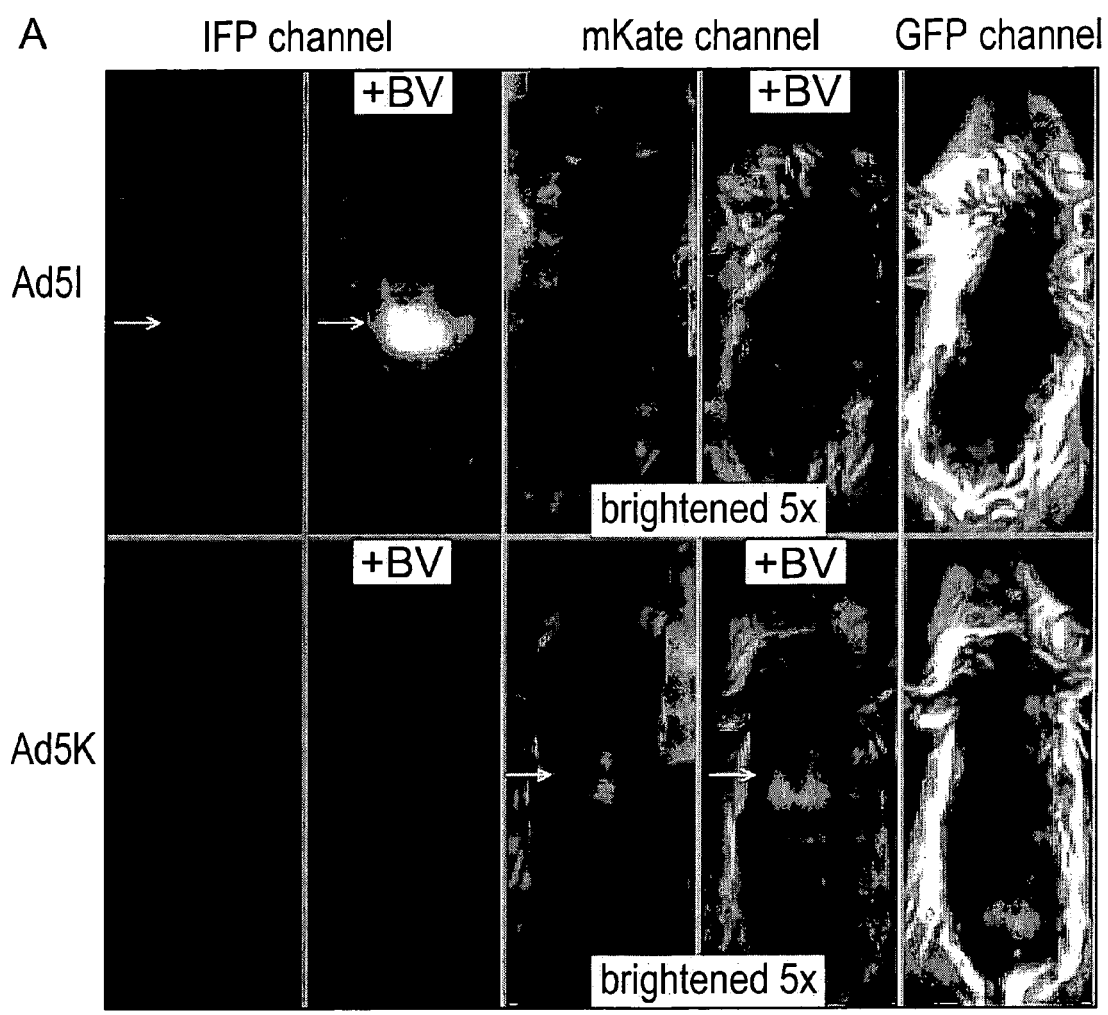

Fig. 20 (Sheet 3)
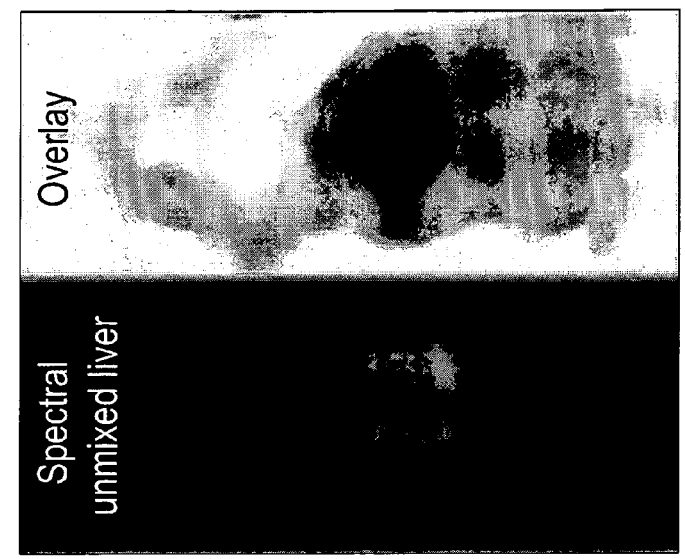
C
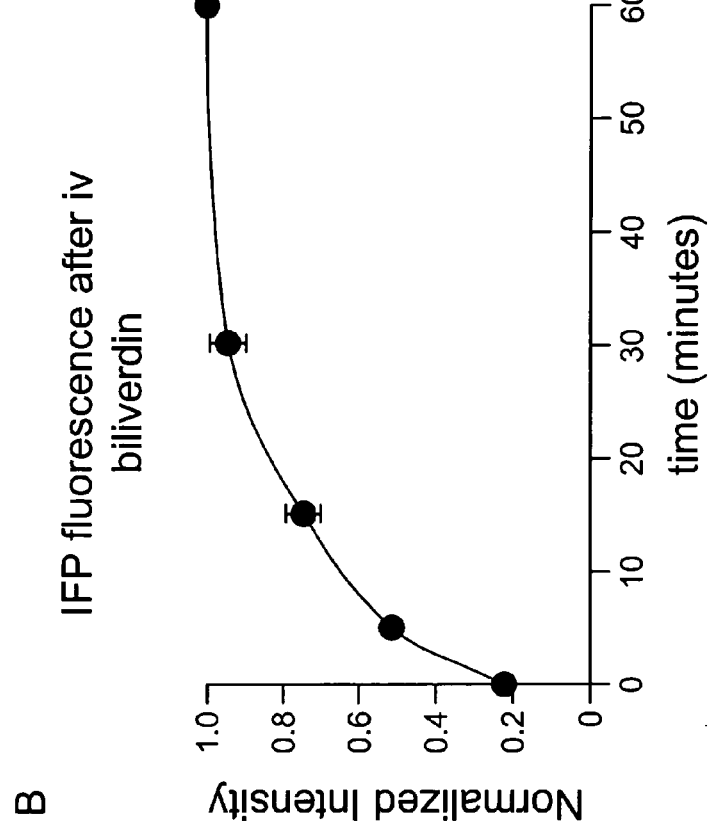
B

Noninvasive fluorescence molecular tomographic (FMT) imaging of IFP-expressing mouse liver.
Arrows indicate rostral-caudal, left-right, and dorsoventral axes respectively. Left: top view. Right: tilted view to show the 3D localization of fluorescence within the mouse.

*Fig. 22 (Sheet 1)*

Analysis of mKate and IFP1.1 visibility and expression levels in livers of mice infected with Ad5I and Ad5K.

(A) IFP and mKate fluorescence images before dissection (skin on), after removal of skin (skin off), and after removal of overlying peritoneum and rib cage (liver exposed). mKate images were 2.5°- brightened relative to IFP images. Note that the Ad5I-infected mouse was imaged after 250 nmol intravenous injection of BV. See bright-field images in fig. S9.

(B) Fluorescence intensity (signal-to-noise ratio) analysis of livers from (A). Average of 80 pixels in the horizontal x axis divided by the average of the 30 most rostral horizontal lines from each of the images starting below the liver (i.e., signal-to-noise ratio), moving rostrally for 300 lines.

(C) Frozen sections were imaged to show IFP, mKate, and GFP expression with a fluorescence stereomicroscope (Lumar, Zeiss), displayed with relative intensity gains of 10, 5, and 1, respectively. Scale bar, 200 mm.

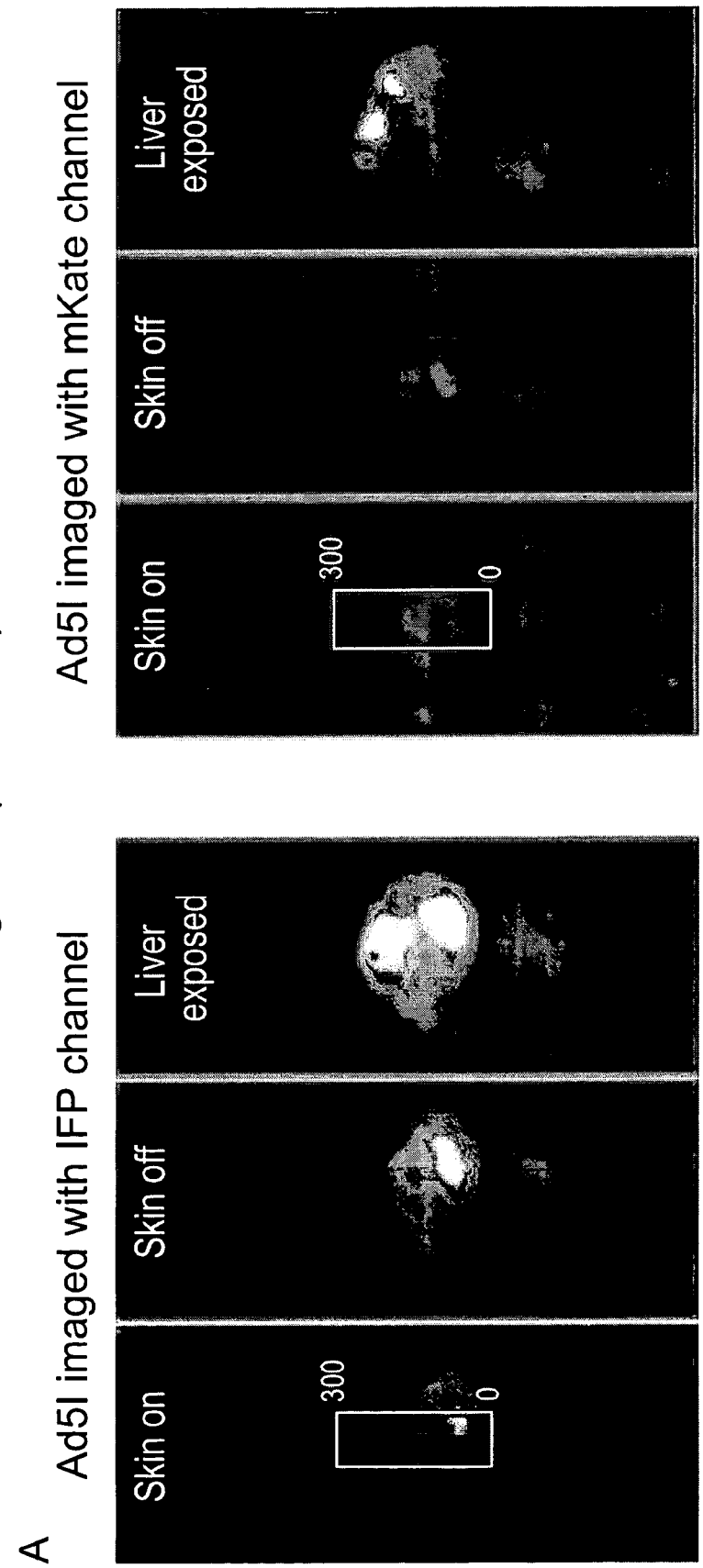
Fig. 22 (Sheet 2)

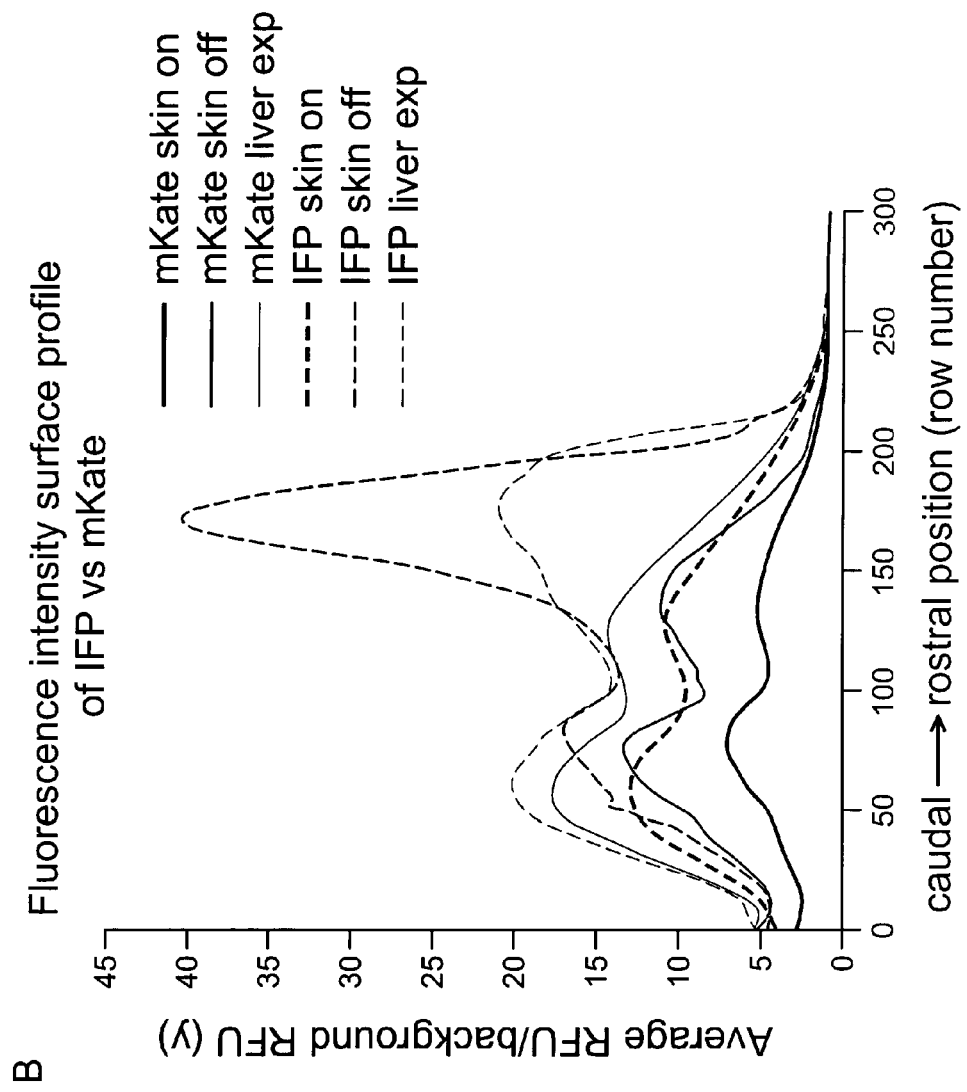
Fig. 22 (Sheet 3)

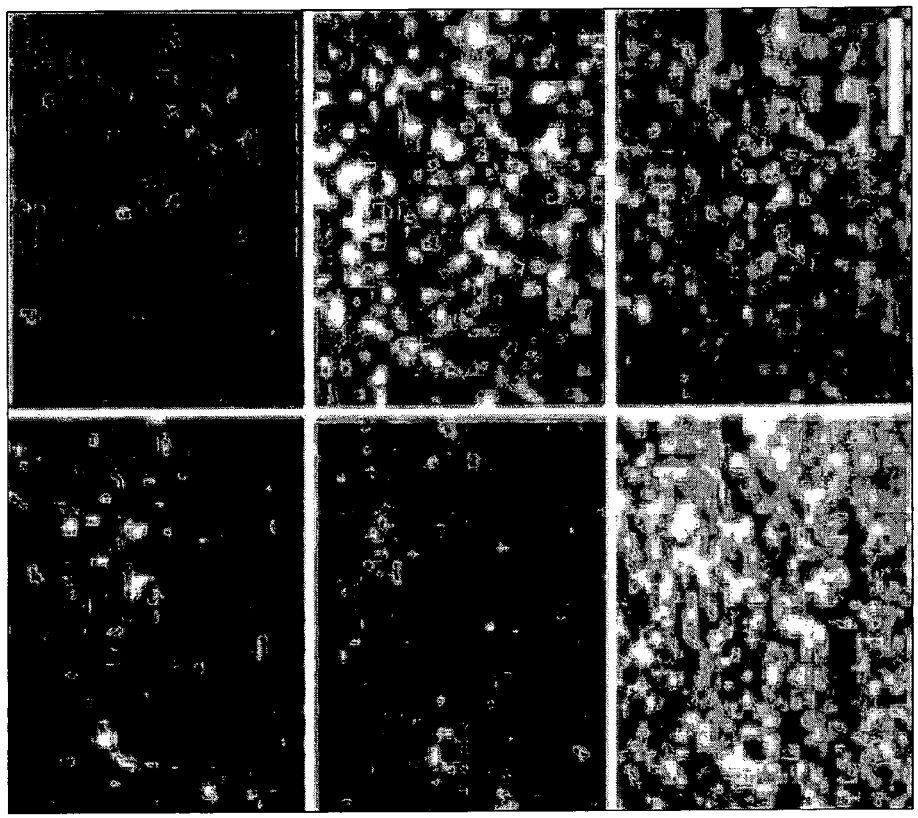

IFP/mKate fluorescence images before dissection (skin on), after removal of skin (skin off), and after removal of overlying peritoneum and ribcage (liver exposed). mKate images were 2.5X brightened relative to IFP images. Note that Ad5I infected mouse was imaged after 250 nmol IV injection of BV.

Imaging of extracted livers
infected with Ad5I and Ad5K.

PROTEINS THAT FLUORESCE AT INFRARED WAVELENGTHS OR GENERATE SINGLET OXYGEN UPON ILLUMINATION

CROSS-REFERENCES TO RELATED APPLICATIONS

This application is a continuation-in-part of U.S. provisional application Ser. Nos. 60/131,751, filed Jun. 11, 2008, and 61/176,062, filed May 6, 2009, and claims priority to both of these applications, the disclosure of which is hereby expressly incorporated by reference in its entirety.

STATEMENT AS TO RIGHTS TO INVENTIONS MADE UNDER FEDERALLY SPONSORED RESEARCH AND DEVELOPMENT

This invention was made with Government support under Grant Nos. GM072033, NS027177, and GM086197, awarded by the National Institutes of Health. The U.S. Government has certain rights in this invention. This invention was also made with Governmental support awarded by the French Government. The French Government may have certain rights in this invention.

REFERENCE TO A "SEQUENCE LISTING," A TABLE, OR A COMPUTER PROGRAM LISTING APPENDIX SUBMITTED ON A COMPACT DISK

NOT APPLICABLE

FIELD OF THE INVENTION

The invention relates to fluorescent proteins and protein variants, and more specifically to mutants of a phytochrome from the bacterium *Deinococcus radiodurans*. In one aspect, the invention provides protein variants that fluoresce at infrared wavelengths. In another aspect, the invention provides protein variants that photogenerate singlet oxygen. The invention also relates to methods of making and using such proteins and protein variants.

Visibly fluorescent proteins (FPs) from jellyfish and corals have revolutionized many areas of molecular and cell biology, but the use of FPs in intact animals such as mice has been handicapped by poor penetration of excitation light. In vivo optical imaging of deep tissues in animals is most feasible between 650 and 900 nm because such wavelengths minimize the absorbance by hemoglobin, water and lipids as well as light scattering (F. F. Jöbsis, *Science* 198. 1264 (1977); R. Weissleder, V. Ntziachristos, *Nat. Med.* 9, 123 (2003)). Thus, genetically encoded, infrared FPs (IFPs) would be particularly valuable for whole-body imaging in cancer diagnosis and treatment, stem cell biology, gene therapy, and other areas of medical research and treatment (T. Schroeder, *Nature* 453, 345 (2008); R. Weissleder, M. J. Pittet, *Nature* 452, 580 (2008)).

However, excitation and emission maxima of FPs in vivo have not exceeded 598 and 655 nm respectively (D. Shcherbo et al., *Nat. Methods* 4, 741 (2007); M. A. Shkrob et al., *Biochem. J.* 392, 649 (2005); L. Wang, W. C. Jackson, P. A. Steinbach, R. Y. Tsien, *Proc. Natl. Acad. Sci. U.S.A.* 101, 16745 (2004)). Somewhat longer wavelengths (644 nm excitation, 672 nm emission) have been observed in a phytochrome-based FP that incorporates phycocyanobilin (PCB) as the chromophore (A. J. Fischer, J. C. Lagarias, *Proc. Natl. Acad. Sci. U.S.A.* 101, 17334 (2004)). Neither incorporation of exogenous PCB nor transfer of its biosynthetic pathway into animal cells has yet been demonstrated.

Bacterial phytochromes are more promising because they incorporate biliverdin IXa (BV) instead of PCB (S. J. Davis, A. V. Vener, R. D. Vierstra, *Science* 286, 2517 (1999)), and BV is the initial intermediate in heme catabolism by heme oxygenase in all aerobic organisms including animals. For example, normal adult humans endogenously generate and metabolize 300-500 mg BV each day simply from routine heme breakdown (J. W. Harris, R. W. Kellermeyer. *The Red Cell,* (Harvard Univ. Press, Cambridge, Mass., 1970)).

Recently, a full-length bacteriophytochrome (DrBphP) from *Deinococcus radiodurans* with a single mutation (D207H) was reported to be red fluorescent at 622 nm upon excitation of the Soret band near 416 nm (J. R. Wagner et al., *J. Biol. Chem.* 283, 12212 (2008)). Excitation of the Q band absorbing at 699 nm gave no fluorescence (Wagner 2008), contradicting Kasha's rule that fluorescence occurs from the lowest excited state. Emission peaks at 710-725 nm have been observed from various forms of *Rhodopseudomonav palustris* (E. Giraud et al., *J. Biol. Chem.* 280, 32389 (2005)) and *Pseudomonas aeruginosa* bacteriophytochromes expressed in *E. coli* (X. Yang, J. Kuk, K. Moffat, *Proc. Natl. Acad. Sci. U.S.A.* 105, 14715 (2008)), but fluorescence efficiencies have not been quantified and reconstitution in nonbacterial systems has not yet been demonstrated.

BRIEF SUMMARY OF THE INVENTION

This invention provides novel truncation mutants of a phytochrome from the bacterium *Deinococcus radiodurans*. When expressed either in bacteria or mammalian cells, these mutant phytochromes spontaneously incorporate biliverdin, a ubiquitous intermediate in heme catabolism, and become fluorescent in the infrared (IR) region. These phytochromes are the first genetically encoded labels that can be excited by far-red light and fluoresce in the true IR (>700 nm). If this protein instead incorporates protoporphyrin IX, an intermediate in heme biosynthesis, illumination now generates significant amounts of singlet oxygen. Singlet oxygen is useful because it can be used to kill individual proteins or cells, detect long-range protein-protein interactions, or generate electron-microscopic contrast.

In one embodiment, the invention provides an isolated polynucleotide encoding a protein, wherein the polynucleotide encodes a protein comprising at least 90% identity to an amino acid sequence of IFP1.4 (SEQ ID NO:20). Preferably, the protein comprises at least 95% identity to the amino acid sequence of IFP1.4 (SEQ ID NO:20). More preferably, the protein comprises the amino acid sequence of IFP1.4 (SEQ ID NO:20). Alternatively, the protein comprises at least 80%, 85%, 90%, 95%, or 100% identity to the amino acid sequence of any one of DrCBD/D207H (SEQ ID NO:2), IFP1.0 (SEQ ID NO: 16), IFP1.1 (SEQ ID NO:17), IFP1.2 (SEQ ID NO:18), and IFP1.3 (SEQ ID NO: 19).

In an alternative embodiment, the polynucleotide encodes a protein comprising at least 90% identity to the amino acid sequence selected from the group consisting of IFP1.4 (SEQ ID NO:20), DrCBD/D207H (SEQ ID NO:2), IFP1.0 (SEQ ID NO: 16), IFP1.01 (SEQ ID NO:3), IFP1.02 (SEQ ID NO:4), IFP1.1 (SEQ ID NO:17). IFP1.2 (SEQ ID NO:18), and IFP1.3 (SEQ ID NO:19). Preferably, the protein comprises at least 95% identity to the amino acid sequence selected from the group consisting of IFP1.4 (SEQ ID NO:20), DrCBD/D207H (SEQ ID NO:2), IFP1.0 (SEQ ID NO:16), IFP1.01 (SEQ ID NO:3), IFP1.02 (SEQ ID NO:4), IFP1.1 (SEQ ID NO:17), IFP1.2 (SEQ ID NO: 18), and IFP1.3 (SEQ ID NO:

19). More preferably, the protein comprises the amino acid sequence selected from the group consisting of IFP1.4 (SEQ ID NO:20), DrCBD/D207H (SEQ ID NO:2), IFP1.0 (SEQ ID NO:16), IFP1.01 (SEQ ID NO:3), IFP1.02 (SEQ ID NO:4), IFP1.1 (SEQ ID NO:17), IFP1.2 (SEQ ID NO:18), and IFP1.3 (SEQ ID NO:19).

In another embodiment, the invention provides an isolated polynucleotide encoding a protein, wherein the protein comprises at least one amino acid residue selected from the group consisting of V54, A119, 1135, M186, M195, Q196, H207, T208, V288, E307, K311, G314, and R318. Preferably, the protein comprises at least four amino acid residues selected from said group. More preferably, the protein comprises at least seven amino acid residues selected from said group. Still more preferably, the protein comprises at least ten amino acid residues selected from said group. Yet still more preferably, the protein comprises all the amino acids residues from said group.

In another aspect, the invention provides a vector comprising a polynucleotide sequence encoding a protein as described by any of said embodiments.

In still another aspect, the invention provides a host cell comprising a vector, said vector comprising a polynucleotide sequence encoding a protein as described by any of said embodiments.

In yet another aspect, the invention provides a polypeptide as described by any of said embodiments.

In still yet another aspect, the invention provides a kit, said kit comprising a polypeptide as described by any of said embodiments.

In an additional aspect, the invention provides a fusion protein, said fusion protein comprising a protein as described by any of said embodiments.

In another embodiment, the invention provides a method of in vivo optical imaging, the method comprising the step of expressing in a cell a polynucleotide encoding a protein as described by any of said embodiments. Preferably, the invention provides a method wherein the cell is a bacterial or mammalian cell. Preferably, the invention provides a method wherein exogenous biliverdin is administered to the cell. Preferably, the invention provides a method wherein a mammal comprises the mammalian cell (i.e., in vivo).

In still another embodiment, the invention provides a method of generating singlet oxygen in a cell, the method comprising the step of: expressing in a cell a polynucleotide encoding a first protein, the first protein comprising a protein encoded by a polynucleotide of any of said embodiments. Preferably, the cell is a bacterial or mammalian cell. Preferably, the singlet oxygen is used to determine protein-protein proximity or interaction or controlled photoablation of the protein or host cell.

DEFINITIONS

Unless specifically indicated otherwise, all technical and scientific terms used herein have the same meaning as commonly understood by those of ordinary skill in the art to which this invention belongs. In addition, method or materials that are substantially equivalent to a method or material described herein can be used in the practice of the present invention. For purposes of the present invention, the following terms are defined.

"A" or "the" as used herein not only includes aspects with one member, but also includes aspects with more than one member. For example, an embodiment including "an IFP and a cofactor" should be understood to present certain aspects with two or more IFPs, two or more cofactors, or both.

"Or" as used herein should in general be construed non-exclusively. For example, an embodiment of "a variant phytochrome comprising the mutations D207H, 1208T, or A288V" would typically present aspects with any two or the three mutations or all three of the mutations. "Or" should, however, be construed to exclude those aspects presented that cannot be combined without contradiction (e.g., "a variant phytochrome comprising the mutations D207H, 1208T, or 1208V" excludes the phytochrome 1208T/I208V).

The term "phytochrome" refers to a class of plant- and bacteria-derived fluorescent proteins. Naturally occurring, non-mutant phytochromes generally fluoresce in the red portion of the visible spectrum. "Bacteriophytochrome" refers to a phytochrome derived from bacteria.

The term "nucleic acid molecule" or "polynucleotide" refers to a deoxyribonucleotide or ribonucleotide polymer in either single-stranded or double-stranded form, and, unless specifically indicated otherwise, encompasses polynucleotides containing known analogs of naturally occurring nucleotides that can function in a similar manner as naturally occurring nucleotides. It will be understood that when a nucleic acid molecule is represented by a DNA sequence, this also includes RNA molecules having the corresponding RNA sequence in which "U" (uridine) replaces "T" (thymidine).

The term "recombinant nucleic acid molecule" refers to a non-naturally occurring nucleic acid molecule containing two or more linked polynucleotide sequences. A recombinant nucleic acid molecule can be produced by recombination methods, particularly genetic engineering techniques, or can be produced by a chemical synthesis method. A recombinant nucleic acid molecule can encode a fusion protein, for example, a fluorescent protein variant of the invention linked to a polypeptide of interest. The term "recombinant host cell" refers to a cell that contains a recombinant nucleic acid molecule. As such, a recombinant host cell can express a polypeptide from a "gene" that is not found within the native (non-recombinant) form of the cell.

Reference to a polynucleotide "encoding" a polypeptide means that, upon transcription of the polynucleotide and translation of the mRNA produced there from, a polypeptide is produced. The encoding polynucleotide is considered to include both the coding strand, whose nucleotide sequence is identical to an mRNA, as well as its complementary strand. It will be recognized that such an encoding polynucleotide is considered to include degenerate nucleotide sequences, which encode the same amino acid residues. Nucleotide sequences encoding a polypeptide can include polynucleotides containing introns as well as the encoding exons.

The term "expression control sequence" refers to a nucleotide sequence that regulates the transcription or translation of a polynucleotide or the localization of a polypeptide to which it is operatively linked. Expression control sequences are "operatively linked" when the expression control sequence controls or regulates the transcription and, as appropriate, translation of the nucleotide sequence (i.e., a transcription or translation regulatory element, respectively), or localization of an encoded polypeptide to a specific compartment of a cell. Thus, an expression control sequence can be a promoter, enhancer, transcription terminator, a start codon (ATG), a splicing signal for intron excision and maintenance of the correct reading frame, a STOP codon, a ribosome binding site, or a sequence that targets a polypeptide to a particular location, for example, a cell compartmentalization signal, which can target a polypeptide to the cytosol, nucleus, plasma membrane, endoplasmic reticulum, mitochondrial membrane or matrix, chloroplast membrane or lumen, medial trans-Golgi cisternae, or a lysosome or endosome. Cell compartmentalization domains are well known in the art and include, for example, a peptide containing amino acid residues 1 to 81 of human type II membrane-anchored protein galactosyltransferase, or amino acid residues 1 to 12 of the presequence of subunit IV of cytochrome c oxidase (see, also, Hancock et al, *EMBO J.* 10:4033-4039, 1991; Buss et al., Mal. Cell. Biol. 8:3960-3963, 1988; and U.S. Pat. No. 5,776, 689; each of which is incorporated herein by reference).

The term "operatively linked" or "operably linked" or "operatively joined" or the like, when used to describe chimeric (i.e., fusion) proteins, refer to polypeptide sequences that are placed in a physical and functional relationship to each other. In a most preferred embodiment, the functions of the polypeptide components of the chimeric protein are unchanged compared to the functional activities of the parts in isolation. For example, a fluorescent protein of the present invention can be fused to a polypeptide of interest. In this case, it is preferable that the fusion molecule retains its fluorescence, and the polypeptide of interest retains its original biological activity. In some embodiments of the present invention, the activities of either the fluorescent protein or the protein of interest can be reduced relative to their activities in isolation. Such fusions can also find use with the present invention. As used herein, the fusion proteins of the invention can be in a monomeric state, or in a multimeric state (e.g., dimeric).

In another example, a dimer fluorescent protein variant of the invention (e.g., IFP1.1 (SEQ ID NO: 17) or IFP1.2 (SEQ ID NO: 18)) comprises two "operatively linked" fluorescent protein units. The two units are linked in such a way that each maintains its fluorescence activity. The first and second units in the tandem dimer need not be identical. In another embodiment, a third polypeptide of interest can be operatively linked to the tandem dimer, thereby forming a three-part fusion protein.

As used herein, the term "brightness," with reference to a fluorescent protein, is measured as the product of the extinction coefficient (EC) at a given wavelength and the fluorescence quantum yield (QY).

The term "probe" refers to a substance that specifically binds to another substance (a "target"). Probes include, for example, antibodies, polynucleotides, receptors and their ligands, and generally can be labeled so as to provide a means to identify or isolate a molecule to which the probe has specifically bound.

The term "label" refers to a composition that is detectable with or without instrumentation, for example, by visual inspection, spectroscopy, or a photochemical, biochemical, immunochemical, or chemical reaction. Useful labels include, for example, phosphorus-32, a fluorescent dye, a fluorescent protein, an electron-dense reagent, an enzyme such as is commonly used in an ELISA, or a small molecule (such as biotin, digoxigenin, or other haptens or peptides) for which an antiserum or antibody, which can be a monoclonal antibody, is available. It will be recognized that a fluorescent protein variant of the invention, which is itself a detectable protein, can nevertheless be labeled so as to be detectable by a means other than its own fluorescence, for example, by incorporating a radionuclide label or a peptide tag into the protein so as to facilitate, for example, identification of the protein during its expression and the isolation of the expressed protein, respectively. A label useful for purposes of the present invention generally generates a measurable signal such as a radioactive signal, fluorescent light, enzyme activity, and the like, either of which can be used, for example, to quantitate the amount of the fluorescent protein variant in a sample.

The term "polypeptide" or "protein" refers to a polymer of two or more amino acid residues. The terms apply to amino acid polymers in which one or more amino acid residue is an artificial, chemical analogue of a corresponding naturally occurring amino acid, as well as to polymers of naturally occurring amino acids. The term "recombinant protein" refers to a protein that is produced by expression of a nucleotide sequence encoding the amino acid sequence of the protein from a recombinant DNA molecule.

The term "isolated" or "purified" refers to a material that is substantially or essentially free from other components that normally accompany the material in its native state in nature. Purity or homogeneity generally are determined using analytical chemistry techniques such as polyacrylamide gel electrophoresis, high-performance liquid chromatography (HPLC), and the like. A polynucleotide or a polypeptide is considered to be isolated when it is the predominant species present in a preparation. Generally, an isolated protein or nucleic acid molecule represents greater than 50% of the macromolecular species present in a preparation, usually represents greater than 80% or 90% of all macromolecular species present, often represents greater than 95%, of the macromolecular species, and, in particular, may be a polypeptide or polynucleotide that purified to essential homogeneity such that it is the only species detected when it is examined using conventional methods for determining the purity of such a molecule.

The term "naturally occurring" is used to refer to a protein, nucleic acid molecule, cell, or other material that exists in the natural world, for example, a polypeptide or polynucleotide sequence that is present in an organism, including in a virus. In general, at least one instance of a naturally occurring material existed in the world prior to its creation, duplication, or identification by a human. A naturally occurring material can be in its form as it exists in the natural world, or can be modified by the hand of man such that, for example, it is in an isolated form.

The term "antibody" refers to a polypeptide substantially encoded by an immunoglobulin gene or immunoglobulin genes, or antigen-binding fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Antibodies exist as intact immunoglobulins or as well-characterized antigen-binding fragments of an antibody, which can be produced by the modification of whole antibodies (e.g., digestion with a peptidase) or can be synthesized de novo using recombinant DNA methods. Such antigen-binding fragments of an antibody include, for example, Fv, Fab' and F(ab)'.sub.2 fragments.

The term "immunoassay" refers to an assay that utilizes an antibody to specifically bind an analyte. An immunoassay is characterized by the use of specific binding properties of a particular antibody to isolate, to target, or to quantify the analyte.

The term "identical," when used in reference to two or more polynucleotide sequences or two or more polypeptide sequences, refers to the residues in the sequences that are the same when aligned for maximum correspondence. When percentage of sequence identity is used in reference to a polypeptide, it is recognized that one or more residue positions that are not otherwise identical can differ by a conservative amino acid substitution, in which a first amino acid residue is substituted for another amino acid residue having similar chemical properties such as a similar charge or hydrophobic or hydrophilic character and, therefore, does not change the functional properties of the polypeptide. Where polypeptide sequences differ in conservative substitutions, the percent sequence identity can be adjusted upwards to correct for the conservative nature of the substitution. Such an adjustment can be made using well-known methods, for example, scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions can be calculated using any well-known algorithm (see, for example, Meyers and Miller, *Comp. Appl. Biol. Sci.* 4:11-17, 1988; Smith and Waterman, *Adv. Appl. Math.* 2:482, 1981; Needleman and Wunsch, *J. Mol. Biol.* 48:443, 1970; Pearson and Lipman, *Proc. Natl. Acad. Sci., USA* 85:2444 (1988); Higgins and Sharp, *Gene* 73:237-244, 1988; Higgins and Sharp, *CABIOS* 5:151-153; 1989; Corpet et al., *Nuci. Acids Res.* 16:10881-10890, 1988; Huang, et al., *Comp. Appl. Biol. Sci.* 8:155-165, 1992; Pearson et al., *Meth. Mol. Biol.* 24:307-331, 1994). Alignment also can be performed by simple visual inspection and manual alignment of sequences.

The term "conservatively modified variation," when used in reference to a particular polynucleotide sequence, refers to different polynucleotide sequences that encode identical or essentially identical amino acid sequences, or where the polynucleotide does not encode an amino acid sequence, to essentially identical sequences. Because of the degeneracy of the genetic code, a large number of functionally identical polynucleotides encode any given polypeptide. For instance, the codons CGU, CGC, CGA, CGG, AGA, and AGG all encode the amino acid argininc. Thus, at every position where an argininc is specified by a codon, the codon can be altered to any of the corresponding codons described without altering the encoded polypeptide. Such nucleotide sequence variations are "silent variations," which can be considered a species of "conservatively modified variations." As such, it will be recognized that each polynucleotide sequence disclosed herein as encoding a fluorescent protein variant also describes every possible silent variation. It will also be recognized that each codon in a polynucleotide, except AUG, which is ordinarily the only codon for methionine, and UUG, which is ordinarily the only codon for tryptophan, can be modified to yield a functionally identical molecule by standard techniques. Accordingly, each silent variation of a polynucleotide that does not change the sequence of the encoded polypeptide is implicitly described herein.

Furthermore, it will be recognized that individual substitutions, deletions or additions that alter, add or delete a single amino acid or a small percentage of amino acids (typically less than 5%, and generally less than 1%) in an encoded sequence can be considered conservatively modified variations, provided alteration results in the substitution of an amino acid with a chemically similar amino acid. Conservative amino acid substitutions providing functionally similar amino acids are well known in the art, including the following six groups, each of which contains amino acids that are considered conservative substitutes for each another:

1) Alanine (Ala, A), Serine (Ser, S), Threonine (Thr, T);
2) Aspartic acid (Asp, D), Glutamic acid (Glu, E);
3) Asparagine (Asn, N), Glutamine (Gln, Q);
4) Arginine (Arg, R), Lysine (Lys, K)
5) Isoleucine (Ile, I), Leucine (Leu, L), Methionine (Met, M), Valine (Val, V); and
6) Phenylalanine (Phe, F), Tyrosine (Tyr, Y). Tryptophan (Trp, W).

Two or more amino acid sequences or two or more nucleotide sequences are considered to be "substantially identical" or "substantially similar" if the amino acid sequences or the nucleotide sequences share at least 90% sequence identity with each other, or with a reference sequence over a given comparison window. Thus, substantially similar sequences include those having, for example, at least 90% sequence identity, at least 95% sequence identity, at least 97% sequence identity, or at least 99% sequence identity.

A subject nucleotide sequence is considered "substantially complementary" to a reference nucleotide sequence if the complement of the subject nucleotide sequence is substantially identical to the reference nucleotide sequence. The term "stringent conditions" refers to a temperature and ionic conditions used in a nucleic acid hybridization reaction. Stringent conditions are sequence dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature, under defined ionic strength and pH, at which 50% of the target sequence hybridizes to a perfectly matched probe.

The term "allelic variants" refers to polymorphic forms of a gene at a particular genetic locus, as well as cDNAs derived from mRNA transcripts of the genes, and the polypeptides encoded by them. The term "preferred mammalian codon" refers to the subset of codons from among the set of codons encoding an amino acid that are most frequently used in proteins expressed in mammalian cells as chosen from the following list:

```
Gly (GGC, GGG);
Glu (GAG);
Asp (GAC);
Val (GUG, GUC);
Ala (GCC, GCU);
Ser (AGC, UCC);
Lys (AAG);
Asn (AAC);
Met (AUG);
Ile (AUC);
Thr (ACC);
Trp (UGG);
Cys (UGC);
Tyr (UAU, UAC);
Leu (CUG);
Phe (UUC);
Arg (CGC, AGG, AGA);
Gln (CAG);
His (CAC);
and
Pro (CCC).
```

Fluorescent molecules are useful in fluorescence resonance energy transfer (FRET), which involves a donor molecule and an acceptor molecule. To optimize the efficiency and detectability of FRET between a donor and acceptor molecule, several factors need to be balanced. The emission spectrum of the donor should overlap as much as possible with the excitation spectrum of the acceptor to maximize the overlap integral. Also, the quantum yield of the donor moiety and the extinction coefficient of the acceptor should be as high as possible to maximize Ro, which represents the distance at which energy transfer efficiency is 50%. However, the excitation spectra of the donor and acceptor should overlap as little as possible so that a wavelength region can be found at which the donor can be excited efficiently without directly exciting the acceptor: Fluorescence arising from direct excitation of the acceptor can be difficult to distinguish from fluorescence arising from FRET. Similarly, the emission spectra of the donor and acceptor should overlap as little as possible so that the two emissions can be clearly distinguished. High-fluorescence quantum yield of the acceptor moiety is desirable if the emission from the acceptor is to be measured either as the sole readout or as part of an emission ratio. One factor to be considered in choosing the donor and acceptor pair is the efficiency of FRET between them. Preferably, the efficiency of FRET between the donor and acceptor is at least 10%, more preferably at least 50% and even more preferably at least 80%.

The term "fluorescent property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between wild-type *Deinococcus radiodurans* FP and a spectral variant, or a mutant thereof, is useful. A measurable difference can be determined by determining the amount of any quantitative fluorescent property, e.g., the amount of fluorescence at a particular wavelength, or the integral of fluorescence over the emission spectrum. Determining ratios of excitation amplitude or emission amplitude at two different wavelengths ("excitation amplitude ratioing" and "emission amplitude ratioing", respectively) are particularly advantageous because the ratioing process provides an internal reference and cancels out variations in the absolute brightness of the excitation source, the sensitivity of the detector, and light scattering or quenching by the sample.

As used herein, the term "fluorescent protein" refers to any protein that can fluoresce when excited with an appropriate electromagnetic radiation, except that chemically tagged proteins, wherein the fluorescence is due to the chemical tag, and polypeptides that fluoresce only due to the presence of certain amino acids such as tryptophan or tyrosine, whose emission peaks at ultraviolet wavelengths (i.e., less that about 400 nm) are not considered fluorescent proteins for purposes of the present invention. In general, a fluorescent protein useful for preparing a composition of the invention or for use in a method of the invention is a protein that derives its fluorescence from autocatalytically forming a chromophore. A fluorescent protein can contain amino acid sequences that are naturally occurring or that have been engineered (i.e., variants or mutants). When used in reference to a fluorescent protein, the term "mutant" or "variant" refers to a protein that is different from a reference protein. For example, a spectral variant of the *Deinococcus radiodurans* phytochrome can be derived from the naturally occurring phytochrome by engineering mutations such as amino acid substitutions into the reference protein. For example, IFP 1.4 (SEQ ID NO:20) is such a spectral variant.

The term "infrared fluorescent protein," or "IFP" is used in the broadest sense. Although it specifically covers the *Deinococcus radiodurans* phytochrome, it also refers to fluorescent proteins from any other species and variant proteins thereof as long as they retain the ability to fluoresce infrared light.

As used herein, reference to a "related fluorescent protein" refers to a fluorescent protein that has a substantially identical amino acid sequence when compared to a reference fluorescent protein. In general, a related fluorescent protein, when compared to the reference fluorescent protein sequence, has a contiguous sequence of at least about 150 amino acids that shares at least about 80%, or at least about 85%, 86%, 87%, 88%, 89%, 90%, 91%, 92%, 93%, 94%, 95%, 96%, 97%, 98%, 99%, or more sequence identity with the reference fluorescent protein, and particularly has a contiguous sequence of at least about 200 amino acids that shares at least about 95% sequence identity with the reference fluorescent protein. In yet other embodiments, the related fluorescent protein may be compared over a region of about 50, or about 75, 100, 125, 150, 200, 250, 300, 350, or the full-length of the protein.

The term "mutant" or "variant" also is used herein in reference to a fluorescent protein that contains a mutation with respect to a corresponding wild type fluorescent protein. In addition, reference is made herein to a "spectral variant" or "spectral mutant" of a fluorescent protein to indicate a mutant fluorescent protein that has a different fluorescence characteristic with respect to the corresponding wild type fluorescent protein.

BRIEF DESCRIPTION OF THE DRAWINGS

FIG. 2 describes the properties of variant IFPs IFP1.0 (SEQ ID NO: 16), IFP1.1 (SEQ ID NO:17), IFP1.2 (SEQ ID NO:18), IFP1.3 (SEQ ID NO:19), and IFP1.4 (SEQ ID NO:20).

FIG. 4 describes the protein sequences of his-tagged IFP1.0 (SEQ ID NO:16), IFP1.01 (SEQ ID NO:3), and IFP1.02 (SEQ ID NO:4).

FIG. 5 describes the absorbance and fluorescence of IFP1.0 (SEQ ID NO: 16), IFP1.01 (SEQ ID NO:3), and IFP1.02 (SEQ ID NO:4).

FIG. 6 illustrates the fluorescence excitation and emission spectra of free protoporphyrin IXa (PPIXa) and PPIXa-bound IFR1.0 (SEQ ID NO: 16) (i.e., "drCBD1").

FIG. 7 illustrates the results of anthracene-9,10-dipropionic acid (ADPA) as a probe for singlet oxygen generated by KillerRed, ReAsH, and DrCBD1+PPIXa.

FIG. 8 describes the cDNA sequences encoding the variant phytochromes of Example 1.

FIG. 9 describes the protein sequences for the variant phytochromes of Example 1.

FIG. 13 describes a sequence alignment of IFP1.4 S2A (SEQ ID NO:15) with DrCBD (SEQ ID NO: 14).

FIG. 15 illustrates the increase of IFP fluorescence by addition of exogenous BV.

FIG. 17 illustrates the rate of IFP1.4 (SEQ ID NO:20) degradation in HEK293A cells without exogenous BV.

FIG. 18 describes the protein sequences for DrCBD (SEQ ID NO:14), IFP1.0 (SEQ ID NO:16), IFP1.1 (SEQ ID NO:14), IFP1.2 (SEQ ID NO:18), IFP1.3 (SEQ ID NO:19), and IFP1.4 (SEQ ID NO:20).

FIG. 20 illustrates the results of imaging of GFP, mKate, and IFP1.1 (SEQ ID NO: 14) in living mice.

FIG. 22 illustrates the results of analysis of mKate and IFP1.1 (SEQ ID NO: 14) visibility and expression levels in livers of mice infected with Ad5I and Ad5K.

DETAILED DESCRIPTION

Figure 1:
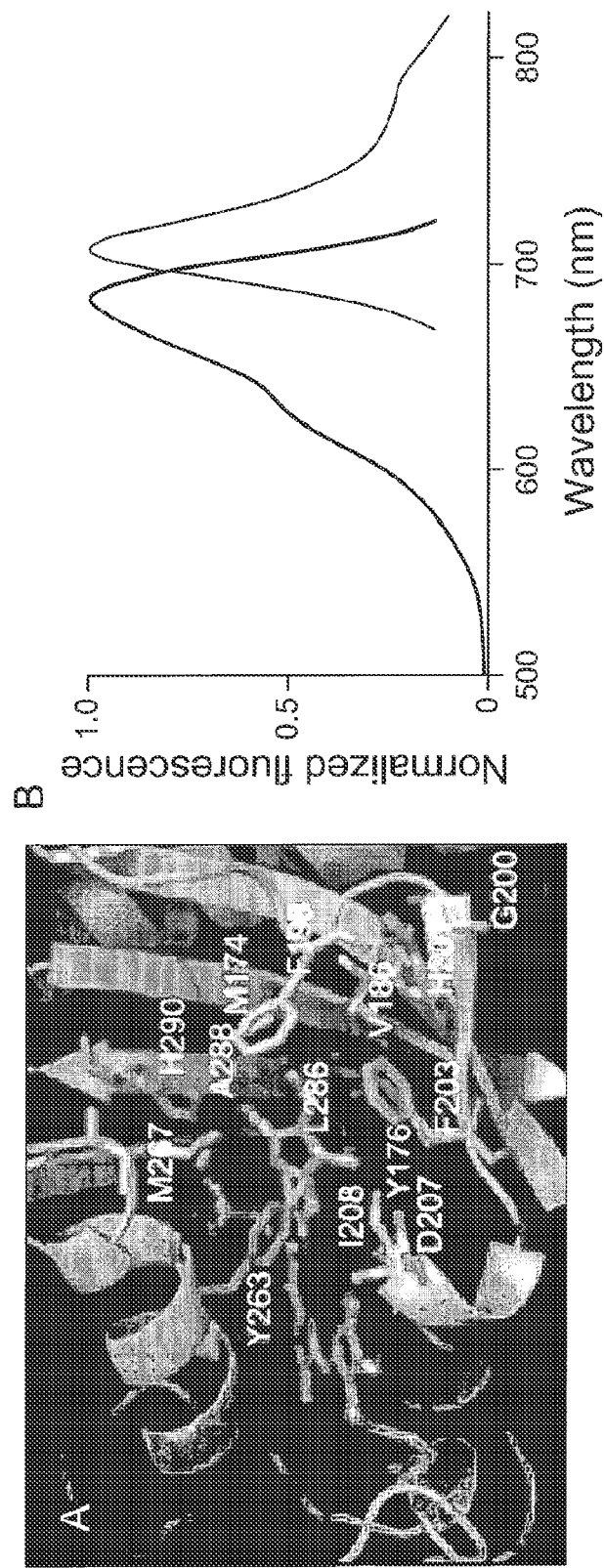
FIG. 1 illustrates the areas targeted for mutagenesis in the preparation of mutant bacteriophytochromes and excitation/emission spectra of the variant bacteriophytochrome IFP1.4 (SEQ ID NO:20).

This invention provides novel mutants of a phytochrome from the bacterium *Deinococcus radiodurans*. When expressed either in bacteria or mammalian cells, these mutant phytochromes spontaneously incorporate biliverdin, a ubiquitous intermediate in heme catabolism, and become fluorescent. If this protein instead incorporates protoporphyrin IX, an intermediate in heme biosynthesis, illumination now generates significant amounts of singlet oxygen. Singlet oxygen is useful because it can be used to kill individual proteins or cells, detect long-range protein-protein interactions, or generate electron-microscopic contrast.

These phytochromes are the first genetically encoded labels that can be excited by far-red light and fluoresce in the true IR (>700 nm). When loaded with a different cofactor, they are also the first proteins that can photogenerate singlet oxygen (SO) without exogenous small molecules. Previous attempts to express bacterial or plant phytochromes and biliproteins in mammalian cells have been unsuccessful. The cofactors necessary for IR emission or SO generation are available in almost all cells and spontaneously bind the apoprotein, whereas previous applications of plant or cyanobacterial phytochromes have required unusual cofactors specific to those organisms, and in some cases additional enzymes to correctly ligate those cofactors into the apoproteins.

The truncated mutants contain three domains P1, P2 and P3. These mutants were created by mutagenesis and DNA shuffling. The apoproteins of these truncated mutants bind biliverdin spontaneously. The generated holoproteins are infrared fluorescent. When the apoprotein binds protoporphyrin, the holoprotein generates singlet oxygen under illumination with a high quantum yield.

The existing techniques are a fluorescent phytochrome variant from cyanobacteria, a fluorescent bacteriophytochrome variant from *Deinococcus radiodurans*, green and red fluorescent proteins homologous to *Aequorea victoria* GFP, and tetracysteines labeled with ReAsH to generate singlet oxygen. The phytochrome variant from cyanobacteria (Fischer & Lagarias 2004) cannot bind to biliverdin and has not been successfully used in mammalian cells. The bacteriophytochrome variant shows an excitation peak at 416 nm and emits at 622 nm (Wagner et al 2008). Fluorescent proteins homologous to *A. victoria* GFP generate undetectably low amounts of SO under normal conditions (Jimenez-Banzo A. et al, 2008). The ReAsH/tetracysteine system is only partially genetically encoded because it still requires addition of a totally synthetic small molecule, which also suffers from nonspecific binding to other cellular proteins. It generates SO with a QY of only 0.05 (Martin et al 2005; Meijer et al 2007).

The IFPs may replace or supplement existing GFP and RFP variants in many applications because the near-infrared wavelengths of fluorescence with biliverdin as cofactor penetrate thick and pigmented tissue much better, have less background due to cellular autofluorescence, are more easily excited by cheap and versatile semiconductor light sources such as laser diodes, and can be detected with no interference from most standard fluorophores. The ability to load the same protein with protoporphyrin IX adds the possibility of correlated electron-microscopic visualization (e.g., usage as a contrast agent), detection and measurement of long-range protein-protein interactions, and controlled photoablation of the host cell or protein. Because the IFPs are genetically and structurally unrelated to existing GFPs and RFPs, they are not encumbered by the extensive intellectual property surrounding the latter. A great many different phytochromes exist in bacteria and plants, so there is abundant raw material from which to evolve other TFPs.

Figure 3:
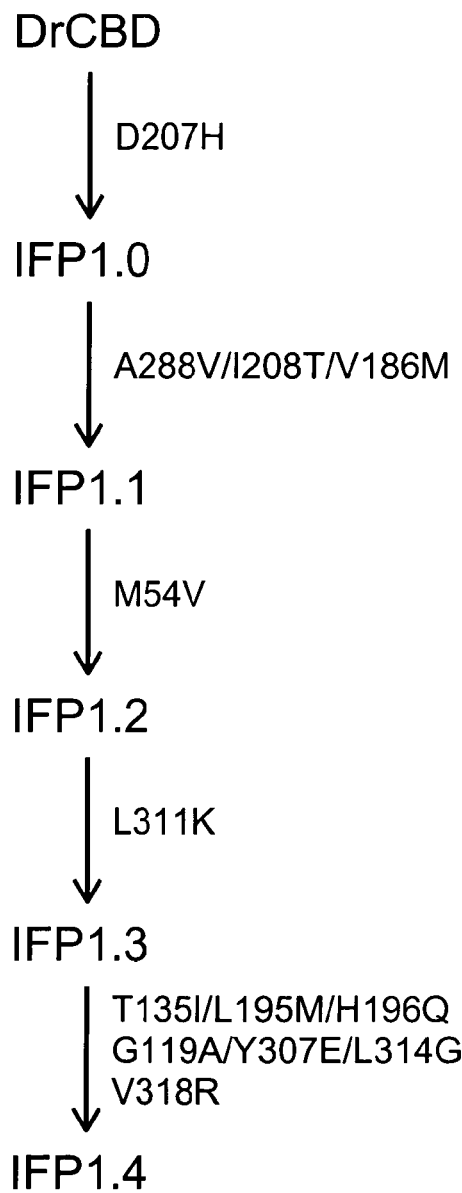
FIG. 3 describes the evolution of IFPs showing the mutations introduced at each stage.

Based on the crystal structure of DrCBD (SEQ ID NO:14) (J. R. Wagner, J. S. Brunelle, K. T. Forest, R. D. Vierstra, *Nature* 438, 325 (2005)), nonradiative decay of the excited chromophore is probably promoted by rotation of the D pyrrole ring due to relatively sparse packing of surrounding residues. Multiple sequence alignment of >100 phytochromes revealed conserved residues, some of which may contribute to photoisomerization. In order to increase the brightness of IFP1.0 (SEQ ID NO: 16), 14 residues near the D ring were chosen and divided into 7 groups for saturation mutagenesis (FIG. 1A), followed by DNA shuffling, which generated IFP1.1 (SEQ ID NO: 14), with excitation and emission maxima of 686 and 713 nm, respectively, and about 2.6 fold greater brightness than IFP1.0 (SEQ ID NO: 16) (FIG. 2). Several more rounds of directed evolution of IFP1.1 (SEQ ID NO:14) led to IFP1.4 (SEQ ID NO:20) (FIG. 3).

Expression of IFP1.4 (SEQ ID NO:20) alone without exogenous BV leads to bright and homogeneous infrared fluorescence in human embryonic kidney cells (HEK293A) (Example 2). Furthermore, exogenously added BV further increases infrared fluorescence of transfected cells including neurons (Example 2), proving that BV is membrane-permeant and adds rapidly to fill IFP1.4 (SEQ ID NO:20) when endogenous BV had not saturated the protein. The half-life of IFP1.4 (SEQ ID NO:20) is about 4 hours in HEK293A cells (Example 2).

TFPs can be imaged over spatial scales from subcellular resolution up to strongly pigmented organs within intact whole mammals, whereas luciferase-based bioluminescence is useful mainly for whole-body imaging (C. H. Contag, M. H. Bachmann, *Annu. Rev. Biomed. Eng.* 4, 235 (2002)). The wavelengths of IFPs are particularly well-suited to optical tomographic reconstruction (V. Ntziachristos et al., *Proc. Natl. Acad. Sci. U.S.A.* 101, 12294 (2004)). Even for microscopic imaging where existing FPs are highly effective, IFPs should reduce the contribution of cellular autofluorescence, enable excitation by cheap laser diodes, add new wavelengths for multicolor labeling, and accept resonance energy transfer from other dyes, FPs, or bioluminescent proteins.

The usefulness of IFPs in protein localization and trafficking may enable new medical, surgical, or diagnostic uses for in vivo imaging. For example, IFPs that are localized in cancer cells could be used to guide excision of tumor bodies and margins during surgery, as the resulting fluorescence would indicate the boundaries of the tumor's infiltration into healthy tissue.

BV is uniquely advantageous as a cofactor because it is spontaneously and irreversibly incorporated into bacteriophytochromes, nontoxic at appropriate doses (R. Ollinger et al., *Antioxid. Redox. Signal* 9, 2175 (2007); N. Atsunori et al., *Gastroenterology* 127, 595 (2004)), nonfluorescent by itself, endogenously produced, and can be further supplemented either by expression of heme oxygenase or by direct administration of commercially available material. Heme oxygenase is an important enzyme in its own right and is involved in various diseases (N. G. Abraham, A. Kappas, *Pharmacol. Rev.* 60, 79 (2008)). Its cumulative activity could be monitored by IFP fluorescence if apoprotein expression were in excess over BV.

More than 1500 bacteriophytochrome-like sequences are already available in the NCBI and CAMERA databases (D. B. Rusch et al., *PLoS Biol.* 5, e77 (2007)). These genes should provide raw material for selection and directed evolution of photochemical transducers based on a scaffold completely independent of the 11-stranded beta-barrel of coelenterate FPs.

Preparation of Recombinant Nucleic Acids

General Recombinant DNA Methods.

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (Kb) or base pairs (bp). These are estimates derived from agarose or acrylamide gel electrophoresis, from sequenced nucleic acids, or from published DNA sequences. For proteins, sizes are given in kilodaltons (kD) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et al., *Nucleic Acids Res.* 12:6159-6168 (1984). Purification of oligonucleotides is by either native acrylamide gel electrophoresis or by anion-exchange HPLC as described in Pearson & Reanier, *J. Chronz.* 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981).

Expression in Prokaryotes and Eukaryotes.

To obtain high level expression of a cloned gene, such as those cDNAs encoding IFP, one typically would subclone IFP into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al, supra. Bacterial expression systems for expressing proteins are available in, e.g., *E. coli*, *Bacillus* sp., and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the IFP-encoding nucleic acid in host cells. A typical expression cassette thus contains a promoter operably linked to the nucleic acid sequence encoding IFP and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, CST, and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can also be regulated using inducible promoters. With inducible promoters, expression levels are tied to the concentration of inducing agents, such as tetracycline or ecdysone, by the incorporation of response elements for these agents into the promoter. Generally, high-level expression is obtained from inducible promoters only in the presence of the inducing agent; basal expression levels are minimal. Inducible expression vectors are often chosen if expression of the protein of interest is detrimental to eukaryotic cells.

Some expression systems have markers that provide gene amplification such as thymidine kinase and dihydrofolate reductase. Alternatively, high-yield expression systems not involving gene amplification are also suitable, such as using a baculovirus vector in insect cells, with an IFP-encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable.

The prokaryotic sequences are preferably chosen such that they do not interfere with the replication of the DNA in eukaryotic cells, if necessary.

Standard transfection methods can be used to produce bacterial, mammalian, yeast or insect cell lines that express large quantities of IFP, which then are purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison. J. Bact. 132:349-351 (1977); Clark-Curtiss & Curtiss, Methods in Enzymology 101:347-362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing IFP.

After the expression vector is introduced into the cells, the transfected cells are cultured under conditions favoring expression of IFP, which is recovered from the culture using standard techniques identified below.

Purification of IFPs

Recombinant IFP can be purified for use in functional assays from any suitable expression system. The IFP monomers may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant IFP is being purified. For example, proteins having established molecular adhesion properties can be reversible fused to the IFPs. With the appropriate ligand, the IFPs can be selectively adsorbed to a purification column and then freed from the column in a relatively pure form. The fused protein is then removed by enzymatic activity. Finally the IFPs could be purified using immunoaffinity columns.

Purification of IFPs from Recombinant Bacteria.

Recombinant proteins are expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of the IFPs inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$. 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human Slo monomers are separated from other bacterial proteins by standard separation techniques, e.g., with Ni-NTA agarose resin.

Alternatively, it is possible to purify the IFPs from bacteria periplasm. After lysis of the bacteria, when the IFPs are exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

Standard Protein Separation Techniques for Purifying IFPs
Solubility Fractionation.

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration.

The molecular weight of the IFPs could be used to isolate it from proteins of greater and lesser size using ultrafiltration through membranes of different pore size (e.g., Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut-off greater than the molecular weight of the protein of interest. The recombinant protein will pass through the membrane into the filtrate. The filtrate can then be chromatographed as described below.

Column Chromatography.

The IFPs can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

EXAMPLES

The following examples are offered to illustrate, but not to limit the claimed invention.

Example 1

Novel Truncation Mutants of a *Deinococcus radiodurans* Phytochrome

Fluorescence of IFP1.0 (SEQ ID NO: 16).

Novel truncation mutants of a phytochrome from the bacterium *Deinococcus radiodurans* were prepared. When expressed either in bacteria or mammalian cells, these mutant phytochromes spontaneously incorporate biliverdin, a ubiquitous intermediate in heme catabolism, and become fluorescent. The initial mutant, drCBD/D207H (SEQ ID NO:2), has excitation and emission maxima at 700 and 713 nm respectively, with quantum yield (QY)>0.03. If this protein instead incorporates protoporphyrin IX, an intermediate in heme biosynthesis, its excitation maxima are 401/501/537/567 nm and emission maxima 622/648/684 nm, and illumination now generates significant amounts of singlet oxygen, with a QY of singlet oxygen generation of 0.15. A second mutant, drCBD/D207H/I208T/A288V (SEQ ID NO:3), tentatively abbreviated IFP1.01 (SEQ ID NO:3), has excitation and emission maxima at 686 and 713 nm respectively, with QY>0.06 (FIGS. 4 and 5).

Generation of Singlet Oxygen by IFP1.0.

The faster the decrease of the ADPA peaks (390-460 nm) as a function of illumination time, the more singlet oxygen was generated. Both the ADPA alone and KillerRed (the FP that was previously most prominently advocated as a generator of singlet oxygen) generated negligible singlet oxygen (FIG. 6). ReAsH was bound to the optimized tetracysteine sequence FLNCCPGCCMEP (SEQ ID NO:1) and clearly generated significant amounts of singlet oxygen (FIG. 7). IFP1.0 (SEQ ID NO:16)+PPIXa was purified away from free PPIXa by affinity chromatography on a nickel-NTA column, and its excitation and emission spectra verified that the PPIXa was bound to a phytochrome, not free (FIG. 4). This complex generated yet more singlet oxygen than the ReAsH-peptide complex did.

Structure of Selected Mutants.

The oligonucleotide and protein sequences of several truncation mutants are as described (FIGS. 8, 9).

Example 2

Mammalian Expression of IFP Engineered from a Bacterial Phytochrome

Gene synthesis, mutagenesis and screening. A gene encoding IFP1.0 (SEQ ID NO:16) with codons optimized for *Escherichia coli* was synthesized by overlap extension PCR (W. P. C. Stemmer, A. Crameri, K. D. Ha, T. M. Brennan, H. L. Heyneker, Gene 164, 49 (1995)). Genetic libraries were constructed by saturation and random mutagenesis as described (N. C. Shaner et al., Nat. Biotechnol. 22, 1567 (2004)) and DNA shuffling (W. P. C. Stemmer, Nature 370, 389 (1994)). IFP1.0 (SEQ ID NO: 16) and mutants were cloned into a modified pBAD vector containing the heme oxygenase-1 gene from cyanobacteria. Libraries were expressed and screened as described (Shaner 2004). A 676 nm laser was used for FRCS screening of large libraries, with 710-900 nm emission filter.

Protein Expression and Characterization.

IFPs in the modified pBAD vector were expressed in *E. coli* strain TOP10. Protein purification, fluorescence characterization and photobleaching experiments were done as described (Shaner 2004). For quantum yield determinations, the integral of the emission spectrum (corrected for the wavelength-dependence of detection sensitivity) of a solution of IFP in PBS was compared with the analogous integral for an equally absorbing solution of Cy5 in PBS, whose quantum yield was assumed to be 0.27 (R. B. Mujumdar, L. A. Ernst, S. R. Mujumdar. C. J. Lewis, A. S. Waggoner, Bioconjug. Chem. 4, 105 (1993)). For extinction coefficient determination, the holoprotein concentration was calculated based on the assumption that the extinction coefficient of holoprotein at 388 nm was equal to that of free BV, which was measured to be 39,900 $M^{-1}$ $cm^{-1}$ in PBS. This is based on the result that the absorbance by the Q band (670-700 nm) decreased by approximately ten-fold after denaturation while the absorbance at 388 nm did not change.

Chimera Construction and Imaging.

DNA encoding IFP1.0 (SEQ ID NO:16) with codons optimized for mammals was synthesized by overlap extension PCR (Stemmer 1995). Other IFPs were created by Quick-Change Multi site-directed mutagenesis. AKT1's PH domain was fused to the c-terminus of IFP1.4 (SEQ ID NO:20) to generate chimeras IFP1.4 (SEQ ID NO:20)-PH$^{AKT1}$. All the IFPs and chimera were cloned into pcDNA3.1 vector. HEK293A cells were transfected with IFP cDNAs using Fugene, then imaged 24-48 hr later on a Zeiss Axiovert microscope with red shifted Cy5.5 filter set (Chroma) and a cooled CCD camera (Photometrics, Tucson, Ariz.), controlled by MetaFluor 2.75 software (Universal Imaging, West Chester, Pa.).

Adenovirus Construction.

To create adenoviruses expressing IFP1.1 (SEQ ID NO: 14) or mKate and GFP, a transcription unit comprising the IFP1.1 (SEQ ID NO: 14) or mKate coding sequence, the poliovirus IRES, and GFP was constructed by assembly PCR, cloned into pENTR1a (Invitrogen), and transferred into pAd-CMV-DEST (Invitrogen) by Gateway recombinase (Invitrogen). Viruses were produced in HEK293 cells by transfection followed by one round of amplification, purified by anion exchange chromatography (FastTrap purification kit, Millipore), resuspended in HBSS+10% glycerol, and stored in aliquots at −80° C. Titers as assessed on HEK293 cells by GFP fluorescence were 5×1010 infectious units (IU) per mL for each virus.

Mouse Imaging.

The University of California San Diego Institutional Animal Care and Use Committee approved the protocol. Albino C57BL/6 mice (Jackson Labs) were injected with 2×109 infectious units of adenovirus via tail vein. After 5 days, belly fur was removed using a depilatory cream. Mice were imaged on a spectral imager (Maestro, Cambridge Research Instruments). The IFP channel was excited with a 650/50 nm (center wavelength/full width at half maximum) bandpass filter with a 700 nm long pass filter in series with the imager's tunable emission filter at 710/40 nm. The mKate channel was 590/24 nm bandpass for excitation and 620/20 in series with 630/40 nm for emission. Imaging of GFP, mKate, and IFP1.1 (SEQ ID NO:14) in living mice were acquired with 467/45 nm excitation and a 515 nm long pass filter in series with the imager's 530/40 nm for emission. Images were taken with 3 seconds exposure. Images were acquired before BV and 1 hr after injection of 250 nanomoles of BV, then scaled so that the brightest pixels after BV administration would display at maximum intensity. mKate and GFP images were first scaled with the same parameters as the IFP images, then the mKate images were further brightened five-fold to make them visible. For fluorescence time course measurement, background-subtracted images of averaged liver intensity of the same region over liver at different time points after 250 nmol biliverdin injection was divided by the fluorescence intensity after 1 hour (Image J, NIH).

For spectral deconvolution, an image cube was collected on the Maestro with excitation at 620/20 nm and emission at 650-800 nm taking an image every 10 nm. Fluorescence region and autofluorescence regions were identified and spectrally unmixed using the instrument's software, revealing true fluorescent protein signal and autofluorescence.

For fluorescence molecular tomographic imaging (FMT), an Ad5I infected mouse was anesthetized with ketamine and midazolam, then injected IV with 250 nmol biliverdin in 10% DMSO. One hour later, the mouse was placed in a FMT 2500 imaging system (VisEn Medical, Bedford Mass.) and imaged in channel 1 with Prosense 680 settings. Images were reconstructed and windowed to show the 3D distribution of fluorescence viewed from two different angles.

After sacrifice, the mice were dissected and imaged using both TFP and mKate filter sets at 3 levels during dissection: with the skin on, with the skin removed, and then with the peritoneum and rib cage removed. Using Image J software, regions of 80×300 pixels were selected from below the liver up to the mid thorax. These regions were analyzed by plotting the profile. The values were normalized by dividing each pixel by the average of the last 30 vertical pixels over the thorax. These data represent contrast of liver to adjacent thoracic background.

Liver Histology.

Livers were frozen for cryohistology to compare fluorescence protein signal strength and relative expression. Sections were cut at 10 tm and then imaged on a fluorescence stereomicroscope (Lumar, Zeiss). Filter sets used were ex 470/40 nm and em 525/50 nm for GFP, ex 560/25 nm and em 607/36 for mKate, and ex 665/45 and em 725/50 for IFP. Images were acquired at 15 s exposures for IFP and mKate channels and 3 s exposure for the GFP channel, then displayed with intensity enhancements of 2, 1, and 1 respectively. Therefore the relative gains for the IFP, mKate, and GFP channels were 10, 5, and 1 respectively.

Preparation of IFP1.0 (SEQ ID NO:16).

Figure 10:
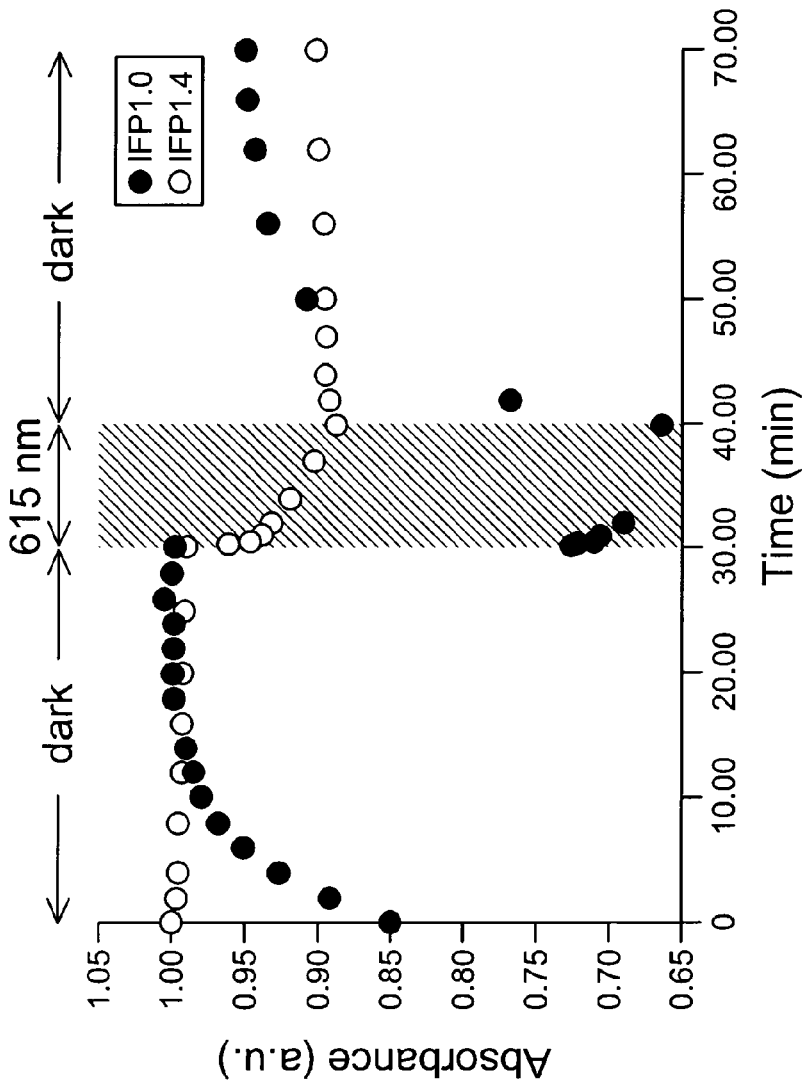
FIG. 10 illustrates the dark and light adapted behavior of IFP1.0 (SEQ ID NO: 16) and IFP1.4 (SEQ ID NO:20)
Figure 11:
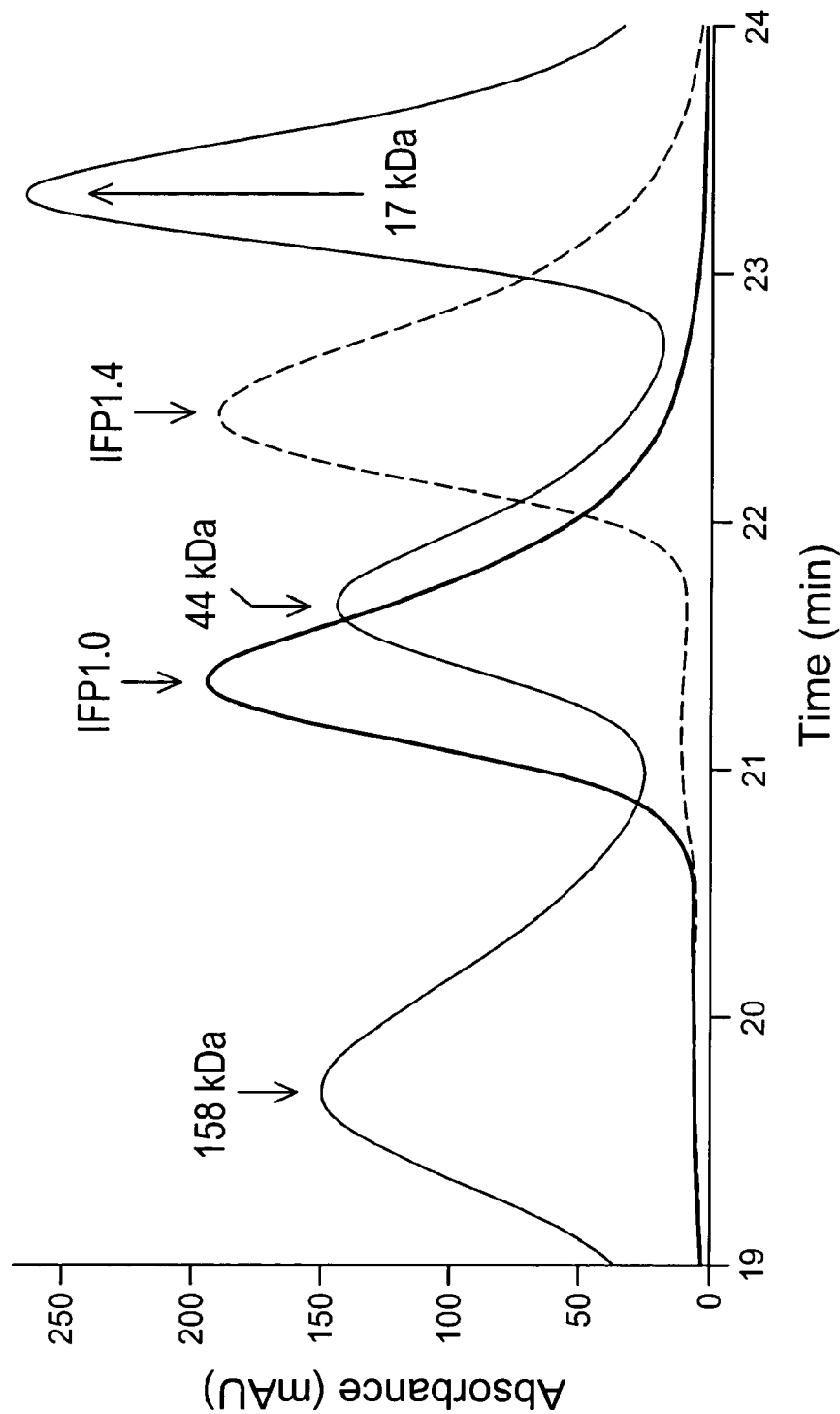
FIG. 11 illustrates the results of size exclusion chromatography for IFP1.0 (SEQ ID NO:16) and IFP1.4 (SEQ ID NO:20).

To minimize the probability of nonradiative decay, DrBphP (NP_285374) was truncated at amino acid 321 to limit the protein to its chromophore-binding domain (DrCBD; SEQ ID NO: 14), consisting of the PAS and GAF domains, which are necessary and sufficient for covalent incorporation of BV (N. C. Rockwell, Y. S. Su, J. C. Lagarias, *Annu. Rev. Plant Biol.* 57, 837 (2006); J. R. Wagner, J. S. Brunelle, K. T. Forest, R. D. Vierstra, *Nature* 438, 325 (2005)). We discarded the PHY domain and the C-terminal histidine kinase related domain (HKRD) (S. J. Davis, A. V. Vener, R. D. Vierstra, *Science* 286, 2517 (1999)), which transduce excited state energy into conformational change and biochemical signaling (Wagner 2005). A gene encoding DrCBD (SEQ ID NO: 14) (321 amino acids) with the D207H mutation was synthesized with codons optimized for *Escherichia coli* by the method previously described (IFP1.0; SEQ ID NO: 16). When coexpressed with cyanobacterial heme oxygenase (HO-1) in *E. coli* and excited near 700 nm, the truncated mutant fluoresced in the infrared with emission maximum of 722 nm. However, this mutant, dubbed IFP1.0 (SEQ ID NO: 16), is weakly fluorescent (FIG. 2), reversibly photofatiguable (FIG. 10), and dimeric (FIG. 11). The dimerization of IFP1.0 (SEQ ID NO: 16) is due to at least 4 residues (Y307/L311/L314/V318) through hydrophobic interactions (FIG. 12A).

Evolution of IFP1.4 (SEQ ID NO:20).

Figure 12:
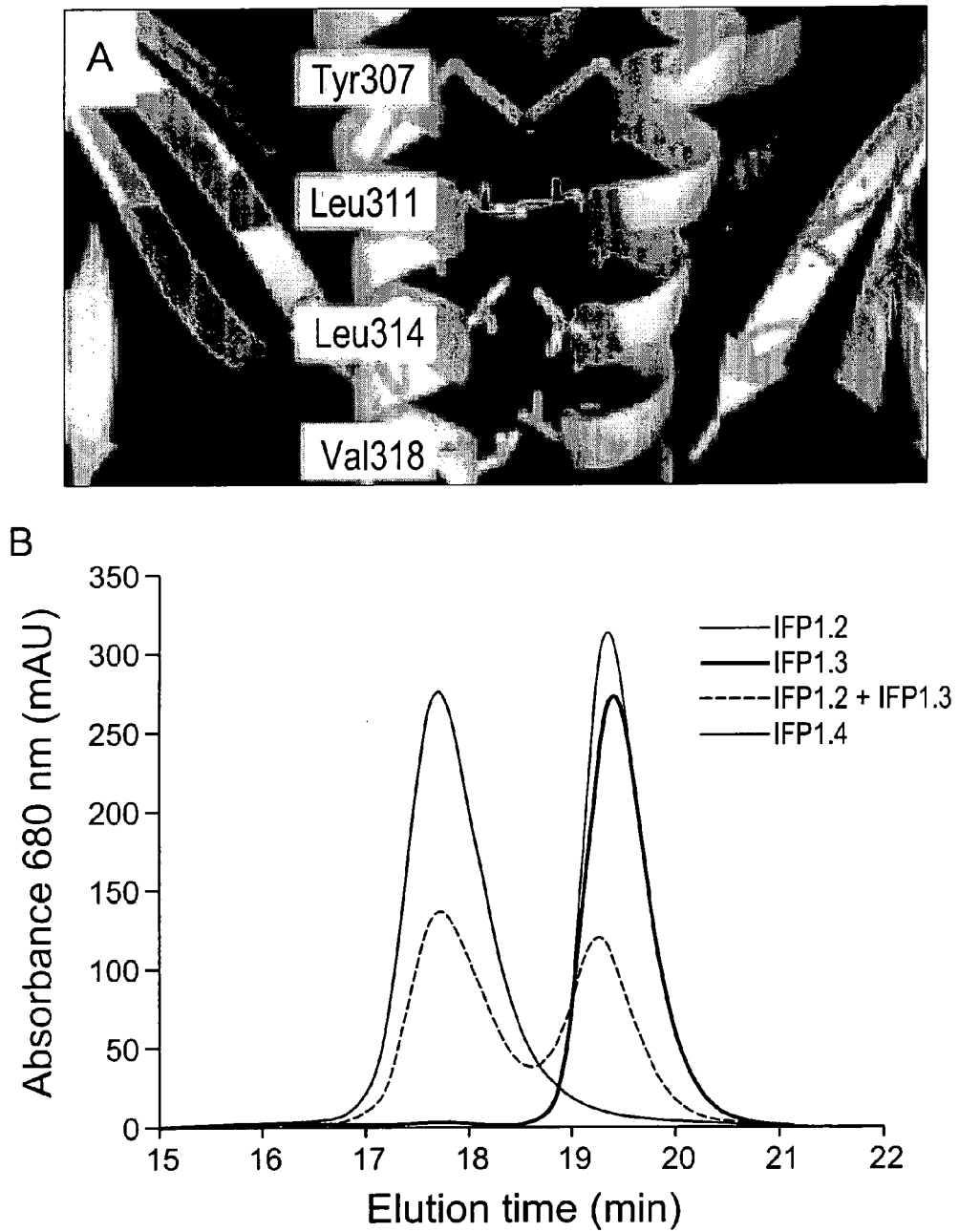
FIG. 12 illustrates the effects of L311K mutation on 1FP monomerization.

Random mutagenesis of IFP1.1 (SEQ ID NO:14) with fluorescence activated cell sorting using a 676 nm laser resulted in IFP1.2 (SEQ ID NO: 18) with 32% increase in quantum yield (QY), due to an additional M54V mutation. However, the parent of IFP1.2 (SEQ ID NO:18), DrCBD (SEQ ID NO:14), was previously shown to be a dimer. Multiple angle light scattering at 785 nm (Dawn 8+, Wyatt Technology, Santa Barbara Calif.) of IFP1.2 (SEQ ID NO: 18) gave an apparent molecular weight 80 kDa, about twice the predicted monomeric size of 36.5 kDa, suggesting that IFP1.2 (SEQ ID NO:18) was also a dimer. To monomerize IFP1.2 (SEQ ID NO:18), Leu311 was rationally mutated to a lysine since it is in the hydrophobic dimer interface based on the crystal structure of DrCBD (SEQ ID NO: 14) (FIG. 12). Size exclusion chromatography (SEC) showed that the resulted mutant (named as IFP1.3 (SEQ ID NO: 19)) was eluted later than IFP1.2 (SEQ ID NO:18) (FIG. 12B), suggesting that IFP1.3 (SEQ ID NO:19) is possibly a monomer. SEC of IFP1.2 (SEQ ID NO: 18)/IFP1.3 (SEQ ID NO: 19) mixture confirmed the result (FIG. 12B). However, the QY of IFP1.3 (SEQ ID NO: 19) was slightly decreased (8%). Another round of random mutagenesis and screening generated IFP1.4 (SEQ ID NO:20) with increased brightness (FIGS. 12, 13). SEC (FIG. 11) and multiple angle light scattering at 12 μM concentration (apparent molecular weight 41.5 kDa±10%) confirmed that IFP1.4 (SEQ ID NO:20) is monomeric.

Properties of IFP1.4 (SEQ ID NO:20).

Figure 14:
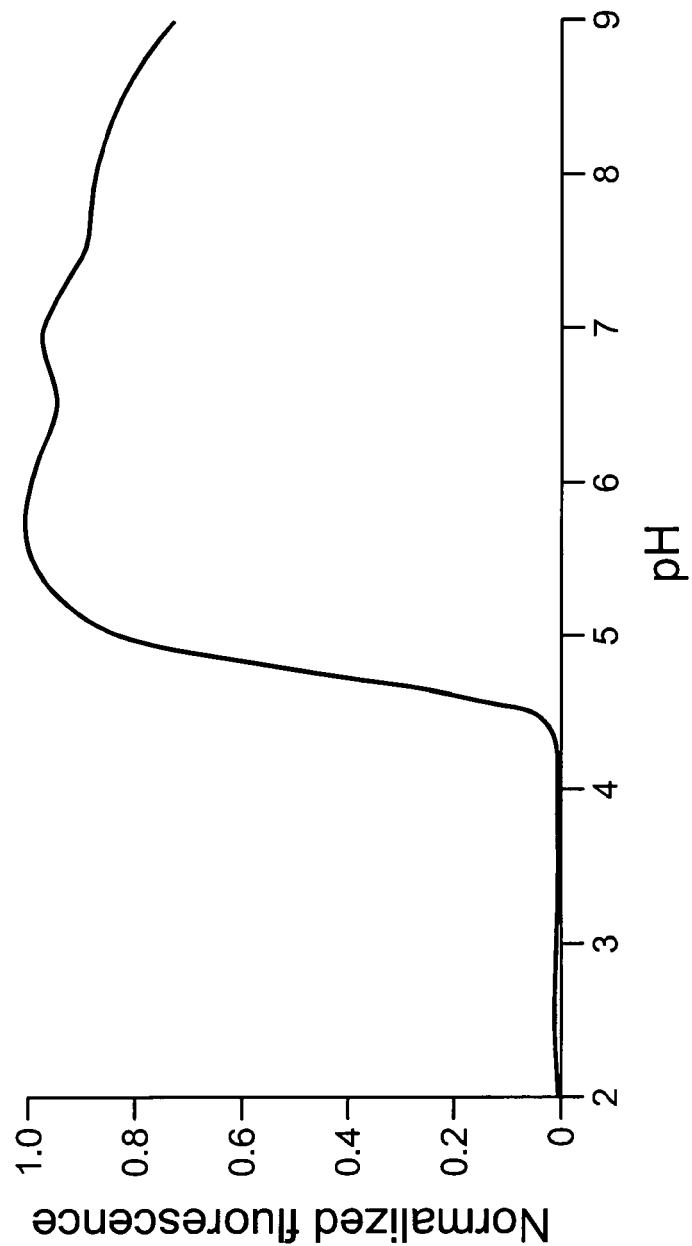
FIG. 14 illustrates the pH dependence of IFP1.4 (SEQ ID NO:20) fluorescence.

IFP1.4 (SEQ ID NO:20) is −4 times brighter than IFP1.0 (SEQ ID NO:16) (FIG. 7) and its fluorescence is stable over a wide pH range from 5 to 9 (FIG. 14). IFP1.4 (SEQ ID NO:20) is monomeric (FIG. 9) and no longer shows significant reversible photofatigue (FIG. 10). At an excitation rate that initially produces 1000 emitted photons/s per molecule of IFP1.1

(SEQ ID NO: 14) or IFP1.4 (SEQ ID NO:20), the time to photobleach by 50% ($t_{1/2}$) is 8.5 or 8.4 s respectively. For comparison, $t_{1/2}$ of the popular yellow fluorescent protein "Venus" is 15 s (N. C. Shaner, P. A. Steinbach, R. Y. Tsien, *Nat. Methods* 2, 905 (2005)). A rationally introduced mutation L311K replaced a hydrophobic group by a charged amino acid and disrupted the dimer interface in IFP 1.2 (SEQ ID NO: 18) (FIG. 12B). Mutation A288V likely eliminated the residual photoconversion of IFP1.0 (SEQ ID NO: 16) since two additional methyl groups of Val288 may limit the D ring rotation. However, the excitation and emission maxima of IFP1.4 (SEQ ID NO:20), 684 and 708 nm respectively, are slightly blue-shifted compared to IFP1.0 (SEQ ID NO: 16) (FIG. 10B). The blue shift may have resulted from using 676 nm excitation, the longest-wavelength laser line available to us, to select for higher brightness during fluorescence activated cell sorting (FRCS).

Increase of Cellular IFP Fluorescence by Exogenous BV.

HEK293A cells were transiently transfected with IFP1.4 (SEQ ID NO:20) in one 10-cm dish and incubated for 24 hours, trypsinized and replated into 5 wells of 6-well plate with ~400,000 cells per well. After another 24 hours incubation, different amounts of BV (final concentrations 5, 10, 20, 40 μM) were added, followed by 90 minutes incubation. Then cells were trypsinized and washed with PBS and resuspended for fluorescence measurement by a 96-well plate reader with monochromators (Safire, TECAN). Untransfected HEK293A cells with additions of exogenous BV were used as controls (FIG. 15). Infrared fluorescence of transfected HEK293A cells increased upon the increase of added exogenous BV concentration and was saturated at 20 μM, while the untransfected cells did not show infrared fluorescence either with or without BV (FIG. 15A). Addition of exogenous BV rapidly (within 10 minutes) led to infrared fluorescence of matured P2 cortical neurons, two weeks after transfection of IFP1.1 (SEQ ID NO: 14) (FIG. 15B), which were practically non-fluorescent before addition of BV.

Half-Life of IFP1.4 (SEQ ID NO:20).

Figure 16:
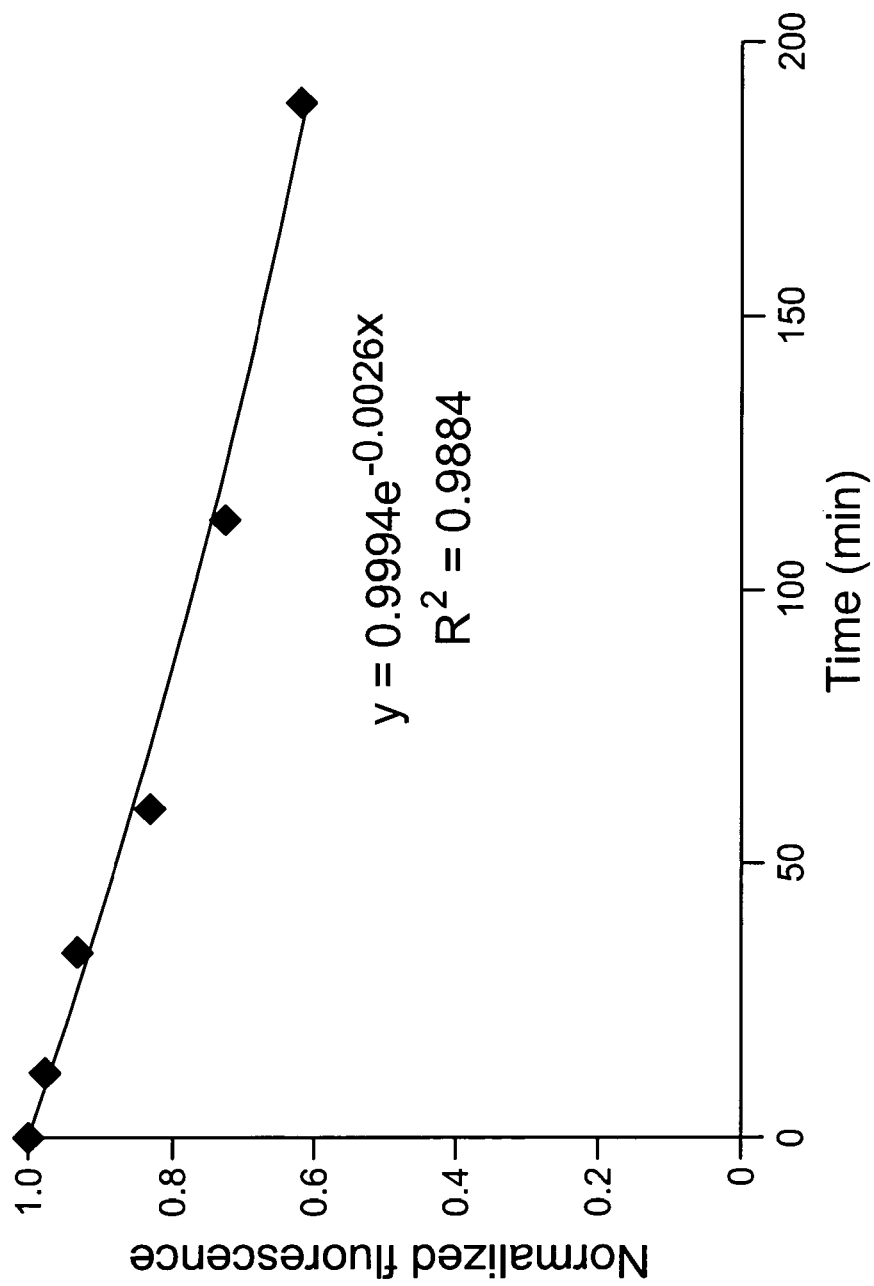
FIG. 16 illustrates the rate of IFP1.4 (SEQ ID NO:20) degradation in HEK293A cells with 20 µM BV added.

Cycloheximide (30 μg/ml final concentration) was added to HEK293A cells 24 hours after transfection of IFP1.4 (SEQ ID NO:20). Infrared fluorescence was fitted with single exponential decay assuming first-order decay kinetics of protein degradation (A. Belle, A. Tanay, L. Bitincka, R. Shamir, E. K. O'Shea, *Proc. Natl. Acad. Sci. U.S.A.* 103, 13004 (2006)) (FIGS. 16 and 17). The half-life of IFP1.4 (SEQ ID NO:20) in HEK293A cells with or without exogenous BV was calculated to be 4.44 and 3.61 hours, whose average is 4.03±0.41 hours.

Multiple Sequence Alignment.

130 bacteriophytochrome-like sequences from NCBI database are aligned using DrCBD as the query (S. F. Altschul et al., *Nucleic Acids Res.* 25, 3389 (1997)).

Preparation of IFP1.4 (SEQ ID NO:20) Fusion Protein.

Figure 19:
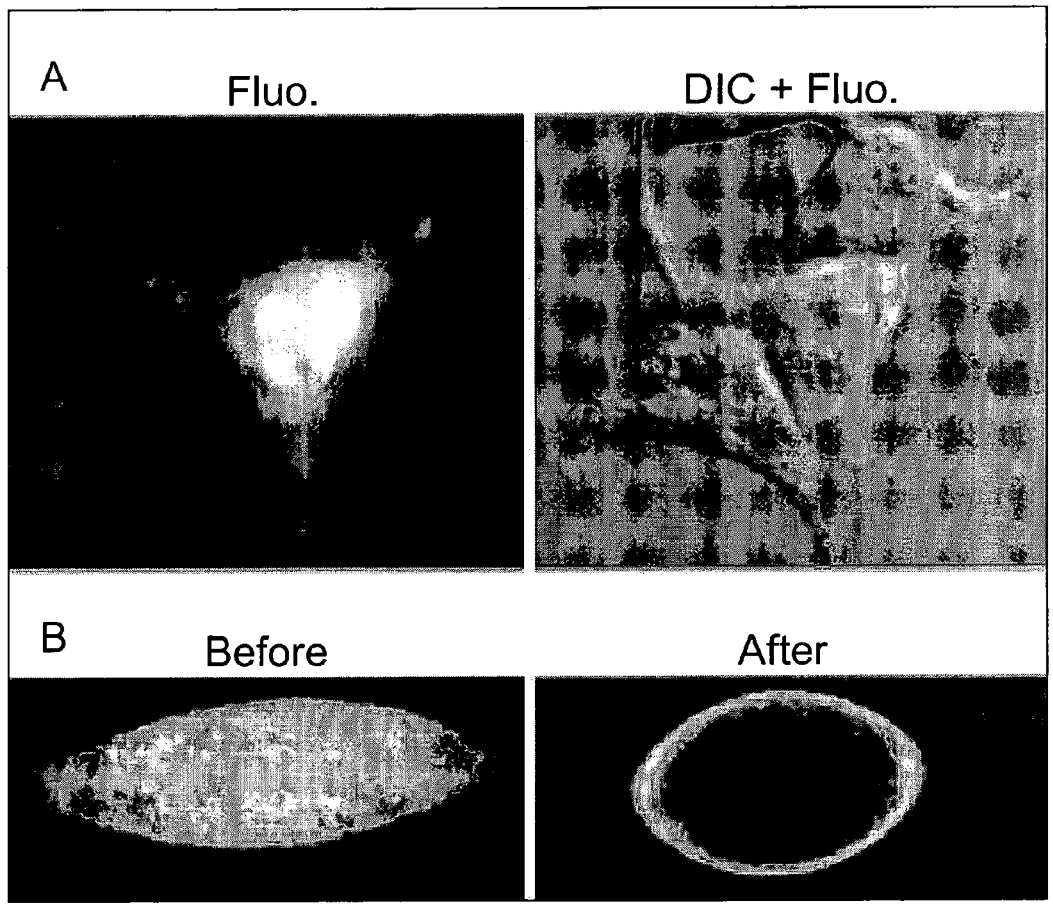
FIG. 19 illustrates the results of imaging of IFP1.4 (SEQ ID NO:20) and IFP1.4 (SEQ ID NO:20)-PHAKT1 in HEK293A cells.

As a simple demonstration that IFP1.4 (SEQ ID NO:20) fusions can be functional, IFP1.4 (SEQ ID NO:20) was fused to the pleckstrin homology (PH) domain of human AKT1 (A. Bellacosa, J. R. Testa, S. P. Staal. P. N. Tsichlis, *Science* 254, 274 (1991)). This PH domain is known to bind to phosphatidylinositol-3,4,5-trisphosphate formed at the plasma membrane after growth factor stimulation. Serum-starved HEK293 cells expressing the IFP1.4 (SEQ ID NO:20)-PHAKT1 fusion showed IR fluorescence diffusely distributed in the cytosol, but this signal translocated to the plasma membrane within 10 min after insulin stimulation (FIG. 19B), illustrating that IFP1.4 (SEQ ID NO:20) can image the trafficking of fusion proteins.

Expression of IFPs in Intact Mice Via Adenovirus Serotype 5.

Figure 21:
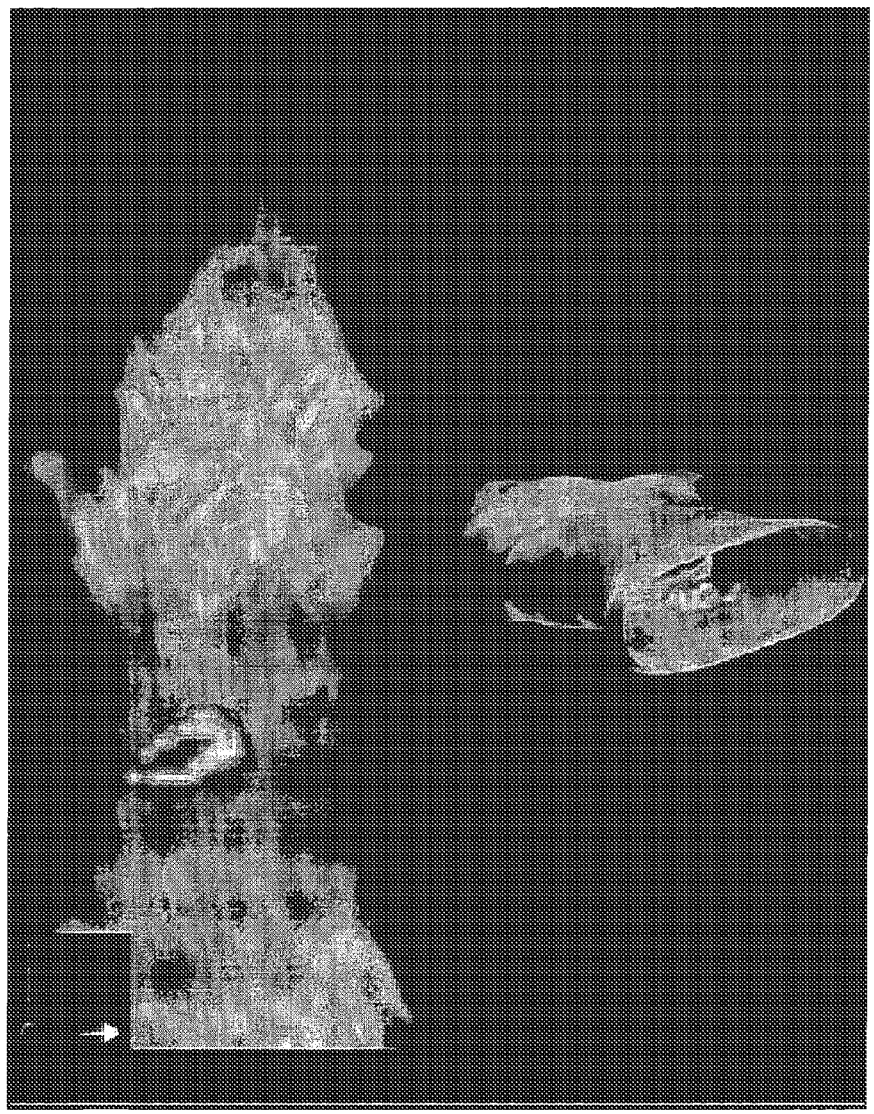
FIG. 21 illustrates the results of non-invasive fluorescence molecular tomographic (FMT) imaging of IFP-expressing mouse liver.

Expression of IFPs in intact mice via adenovirus serotype 5 (Ad5) also produced infrared fluorescence. Ad5 is well known to infect mouse liver specifically (S. N. Waddington et al., *Cell* 132, 397 (2008)). Two modified Ad5 were generated: Ad5I and Ad5K. Ad5I contains the genes for IFP1.1 (SEQ ID NO:14) and GFP, the latter controlled by an internal ribosome entry sequence (IRES). Ad5K encodes mKate, a red fluorescent protein advocated for in vivo imaging (D. Shcherbo et al., *Nat. Methods* 4, 741 (2007)), and IRES-GFP. Weak infrared fluorescence of liver was detected 5 days after intravenous (IV) injection of Ad5I through tail vein (FIG. 20A). The whole liver was easily detected after IV injection of 250 nmol (~7 mg/kg) BV (FIG. 20A). The increase in liver fluorescence was half-maximal in ~10 min and maximal (~5-fold) 1 hour after BV injection (FIG. 20B). Resolution of IFP fluorescence from background autofluorescence can be enhanced by spectral deconvolution (FIG. 20C). The three-dimensional distribution of IFP fluorescence in the mouse liver can be reconstructed tomographically (FIG. 21).

BV injection did not cause observable toxicity in mice: Six mice after BV injection were observed for 3 days, the maximum time that we could hold mice for imaging according to our university approved animal protocol. Higher doses of BV (35-50 mg/kg) have been reported to give beneficial protection in vivo against reactive oxygen species (R. Ollinger et al., *Antioxid. Redox. Signal* 9, 2175 (2007)) and transplantation-induced injury (N. Atsunori et al., *Gastroenterology* 127, 595 (2004)).

Figure 23:
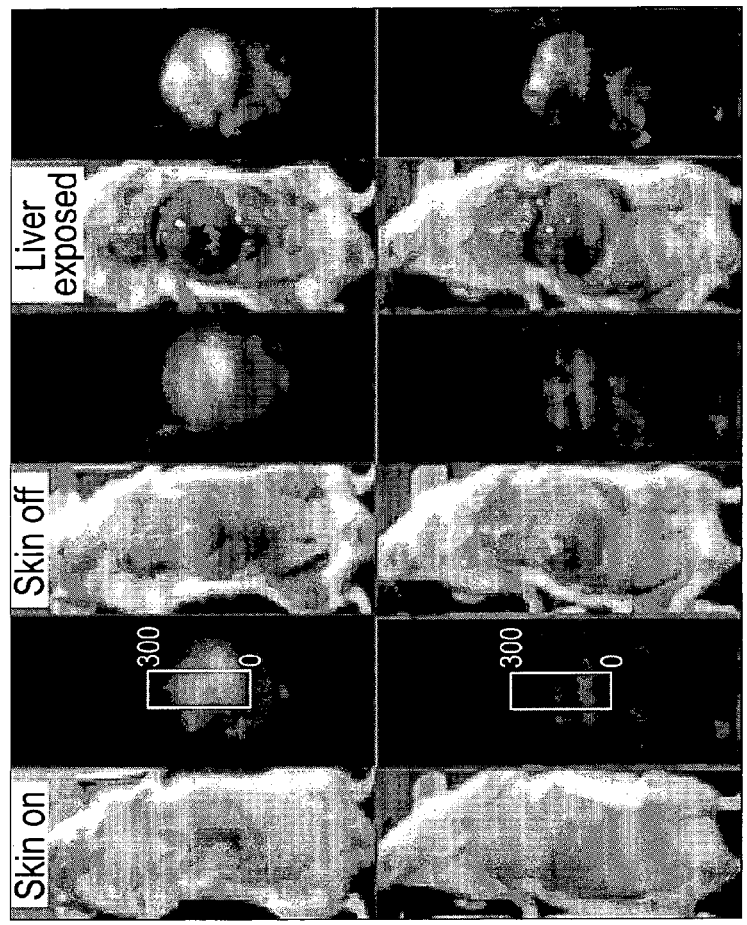
FIG. 23 illustrates the results of IFP/mKate fluorescence images before dissection, after removal of skin, and after removal of overlying peritoneum and ribcage.

As a control, IV injection of 250 nmol BV did not generate infrared fluorescence in either Ad5K infected (FIG. 19A) or non-virus infected mice (data not shown). The far-red fluorescence of mKate was observed in Ad5K infected liver, and was unaffected by BV. Neither Ad5I nor Ad5K infected mice displayed GFP fluorescence in the liver of intact mice (FIG. 20A). Removal of the overlying skin, followed by complete exposure of the liver, increased the mKate fluorescence by a much greater factor than for the IFP signal (FIG. 22 and FIG. 23), illustrating how overlying tissues attenuate mKate's excitation and emission wavelengths to a greater extent than those for IFP.

Figure 24:
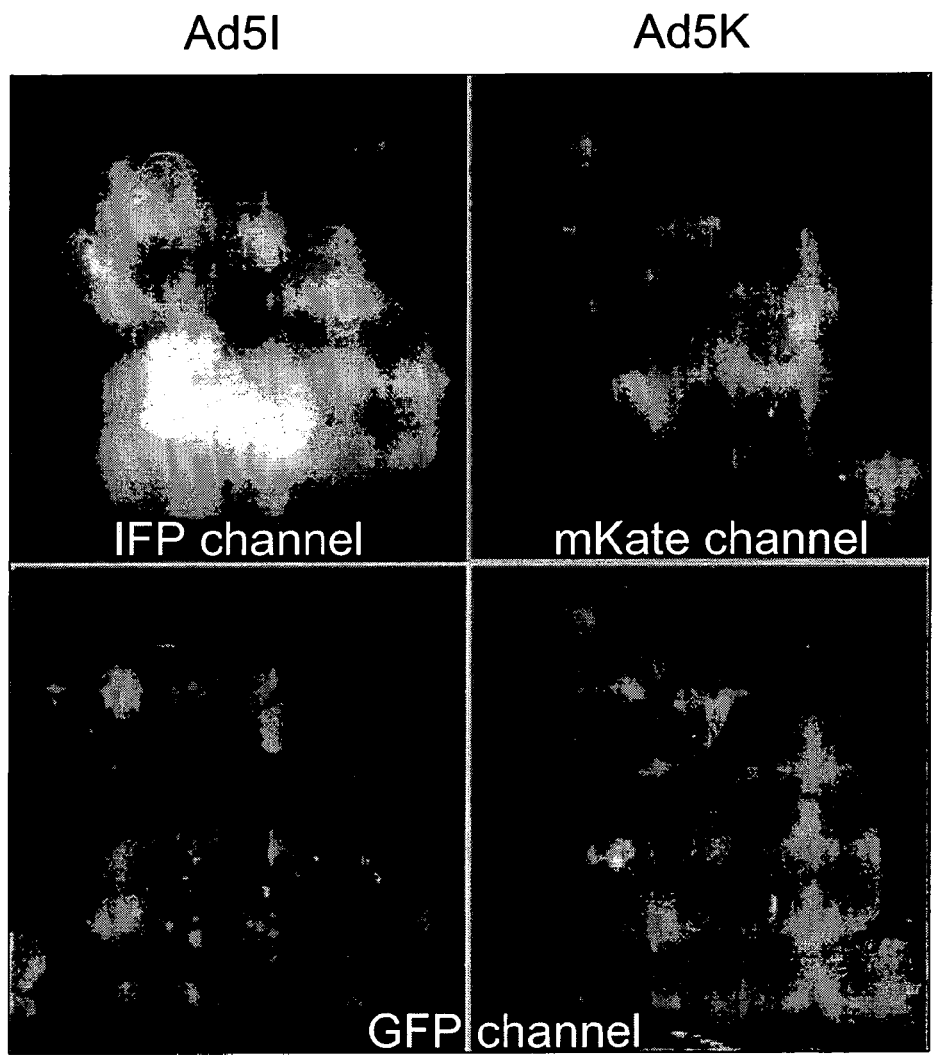
FIG. 24 illustrates the results of imaging extracted livers infected with Ad5I and Ad5K.

The entire dissected liver was fluorescent for mice expressing IFP and mKate (FIG. 23), suggesting virus infection of the whole liver. GFP fluorescence became visible only after complete extraction of the liver and was similar for Ad5I vs. Ad5K (FIG. 24), suggesting similar efficiencies of viral infection. Fluorescence microscopy of frozen sections showed fluorescence increasing in the order IFP1.1 (SEQ ID NO:14) <mKate<GFP fluorescence (FIG. 22C), confirming that IFP remains detectable in histology and that its improved visibility in vivo is due not to higher expression levels, but rather to superior penetration of longer excitation and emission wavelengths through bulk pigmented tissue.

It is understood that the examples and embodiments described herein are for illustrative purposes only. Various modifications or changes in view thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated polynucleotide encoding a protein, wherein the polynucleotide encodes a protein comprising at least 97% identity to an amino acid sequence comprising IFP 1.4 (SEQ ID NO:20).

2. The polynucleotide of claim 1, wherein the protein comprises at least 99% identity to an amino acid sequence selected from the group consisting of IFP1.4 (SEQ ID NO:20), IFP1.2 (SEQ ID NO:18), and IFP1.3 (SEQ ID NO:19).

3. The polynucleotide of claim 1, wherein the protein comprises an amino acid sequence selected from the group consisting of IFP 1.4 (SEQ ID NO:20), IFP1.1 (SEQ ID NO:17), IFP1.2 (SEQ ID NO:18), and IFP1.3 (SEQ ID NO:19).

4. The polynucleotide of claim 1, wherein the protein comprises at least one amino acid residue selected from the group consisting of V54, A119, I135, M186, M195, Q196, T208, V288, E307, K311, G314, and R318, and wherein the amino acid position corresponds to SEQ ID NO:20.

5. The polynucleotide of claim 4, wherein the protein comprises at least four amino acid residues selected from the group consisting of V54, A119, I135, M186, M195, Q196, T208, V288, E307, K311, G314, and R318, and wherein the amino acid position corresponds to SEQ ID NO: 20.

6. The polynucleotide of claim 5, wherein the protein comprises at least seven amino acid residues selected from the group consisting of V54, A 119, I135, M186, M195, Q196, T208, V288, E307, K311, G314, and R318, and wherein the amino acid position corresponds to SEQ ID NO: 20.

7. The polynucleotide of claim 6, wherein the protein comprises at least ten amino acid residues selected from the group consisting of V54, A119, I135, M186, M195, Q196, T208, V288, E307, K311, G314, and R318, and wherein the amino acid position corresponds to SEQ ID NO: 20.

8. The polynucleotide of claim 7, wherein the protein comprises the amino acid residues V54, A119, I135, M186, M195, Q196, T208, V288, E307, K311, G314, and R318, and wherein the amino acid position corresponds to SEQ ID NO: 20.

9. A vector comprising the polynucleotide sequence of claim 1.

10. A host cell comprising the vector of claim 9.

11. A kit comprising the polynucleotide of claim 1.

12. A method of in vivo optical imaging, the method comprising the step of: expressing in a cell a polynucleotide encoding a first protein, the first protein comprising a protein encoded by a polynucleotide of claim 1.

13. The method of claim 12, wherein the cell is a bacterial or mammalian cell.

14. The method of claim 12, wherein exogenous biliverdin is administered to the cell.

15. The method of claim 12, wherein a mammal comprises the mammalian cell.

16. A method of generating singlet oxygen in a cell, the method comprising the step of: expressing in a cell a polynucleotide encoding a first protein, the first protein comprising a protein encoded by a polynucleotide of claim 1.

17. The method of claim 16, wherein the cell is a bacterial or mammalian cell.

18. The method of claim 16, wherein the singlet oxygen is used to determine protein-protein proximity or interaction or controlled photoablation of the protein or host cell.

19. An isolated polynucleotide encoding a protein, wherein the polynucleotide encodes a protein comprising at least 90% identity to the amino acid sequence of IFP1.4 (SEQ ID NO:20), wherein the polynucleotide comprises at least one amino acid residue selected from the group consisting of V54, A119, I135, M186, M195, Q196, T208, V288, E307, K311, G314, and R318.

* * * * *

SEQUENCE LISTING

<160> NUMBER OF SEQ ID NOS: 21

<210> SEQ ID NO 1
<211> LENGTH: 12
<212> TYPE: PRT
<213> ORGANISM: Artificial Sequence
<220> FEATURE:
<223> OTHER INFORMATION: optimized tetracysteine sequence for ReAsH-
      peptide complex singlet oxygen generation

<400> SEQUENCE: 1

Phe Leu Asn Cys Cys Pro Gly Cys Cys Met Glu Pro
1               5                   10

<210> SEQ ID NO 2
<211> LENGTH: 329
<212> TYPE: PRT
<213> ORGANISM: Artificial Sequence
<220> FEATURE:
<223> OTHER INFORMATION: synthetic infrared fluorescent protein (IFP),
      truncated bacteriophytochrome chromophore-binding
      domain from Deinococcus radiodurans with a single
      mutation, DrCBD/D207H (IFP1.0 his6)

<400> SEQUENCE: 2

Met Ser Arg Asp Pro Leu Pro Phe Phe Pro Pro Leu Tyr Leu Gly Gly
1               5                   10                  15

Pro Glu Ile Thr Thr Glu Asn Cys Glu Arg Glu Pro Ile His Ile Pro
            20                  25                  30

Gly Ser Ile Gln Pro His Gly Ala Leu Leu Thr Ala Asp Gly His Ser
        35                  40                  45

Gly Glu Val Leu Gln Met Ser Leu Asn Ala Ala Thr Phe Leu Gly Gln
    50                  55                  60

Glu Pro Thr Val Leu Arg Gly Gln Thr Leu Ala Ala Leu Leu Pro Glu
65                  70                  75                  80

Gln Trp Pro Ala Leu Gln Ala Ala Leu Pro Pro Gly Cys Pro Asp Ala
                85                  90                  95

Leu Gln Tyr Arg Ala Thr Leu Asp Trp Pro Ala Ala Gly His Leu Ser
            100                 105                 110

Leu Thr Val His Arg Val Gly Glu Leu Leu Ile Leu Glu Phe Glu Pro
        115                 120                 125

Thr Glu Ala Trp Asp Ser Thr Gly Pro His Ala Leu Arg Asn Ala Met
130                 135                 140

Phe Ala Leu Glu Ser Ala Pro Asn Leu Arg Ala Leu Ala Glu Val Ala
145                 150                 155                 160

Thr Gln Thr Val Arg Glu Leu Thr Gly Phe Asp Arg Val Met Leu Tyr
                165                 170                 175

Lys Phe Ala Pro Asp Ala Thr Gly Glu Val Ile Ala Glu Ala Arg Arg
            180                 185                 190

Glu Gly Leu His Ala Phe Leu Gly His Arg Phe Pro Ala Ser His Ile
        195                 200                 205

Pro Ala Gln Ala Arg Ala Leu Tyr Thr Arg His Leu Leu Arg Leu Thr
    210                 215                 220

Ala Asp Thr Arg Ala Ala Ala Val Pro Leu Asp Pro Val Leu Asn Pro
225                 230                 235                 240

Gln Thr Asn Ala Pro Thr Pro Leu Gly Gly Ala Val Leu Arg Ala Thr
                245                 250                 255

Ser Pro Met His Met Gln Tyr Leu Arg Asn Met Gly Val Gly Ser Ser

```
                260                 265                 270
Leu Ser Val Ser Val Val Gly Gly Gln Leu Trp Gly Leu Ile Ala
        275                 280                 285

Cys His His Gln Thr Pro Tyr Val Leu Pro Pro Asp Leu Arg Thr Thr
        290                 295                 300

Leu Glu Tyr Leu Gly Arg Leu Leu Ser Leu Gln Val Gln Val Lys Glu
305                 310                 315                 320

Ala Glu Phe His His His His His His
                325

<210> SEQ ID NO 3
<211> LENGTH: 329
<212> TYPE: PRT
<213> ORGANISM: Artificial Sequence
<220> FEATURE:
<223> OTHER INFORMATION: synthetic infrared fluorescent protein (IFP),
      truncated bacteriophytochrome chromophore-binding
      domain from Deinococcus radiodurans with 3
      mutations, DrCBD/D207H/I208T/A288V (IFP1.01 his6)

<400> SEQUENCE: 3

Met Ser Arg Asp Pro Leu Pro Phe Phe Pro Pro Leu Tyr Leu Gly Gly
1               5                   10                  15

Pro Glu Ile Thr Thr Glu Asn Cys Glu Arg Glu Pro Ile His Ile Pro
                20                  25                  30

Gly Ser Ile Gln Pro His Gly Ala Leu Leu Thr Ala Asp Gly His Ser
        35                  40                  45

Gly Glu Val Leu Gln Met Ser Leu Asn Ala Ala Thr Phe Leu Gly Gln
    50                  55                  60

Glu Pro Thr Val Leu Arg Gly Gln Thr Leu Ala Ala Leu Leu Pro Glu
65                  70                  75                  80

Gln Trp Pro Ala Leu Gln Ala Ala Leu Pro Pro Gly Cys Pro Asp Ala
                85                  90                  95

Leu Gln Tyr Arg Ala Thr Leu Asp Trp Pro Ala Ala Gly His Leu Ser
            100                 105                 110

Leu Thr Val His Arg Val Gly Glu Leu Leu Ile Leu Glu Phe Glu Pro
        115                 120                 125

Thr Glu Ala Trp Asp Ser Thr Gly Pro His Ala Leu Arg Asn Ala Met
    130                 135                 140

Phe Ala Leu Glu Ser Ala Pro Asn Leu Arg Ala Leu Ala Glu Val Ala
145                 150                 155                 160

Thr Gln Thr Val Arg Glu Leu Thr Gly Phe Asp Arg Val Met Leu Tyr
                165                 170                 175

Lys Phe Ala Pro Asp Ala Thr Gly Glu Val Ile Ala Glu Ala Arg Arg
            180                 185                 190

Glu Gly Leu His Ala Phe Leu Gly His Arg Phe Pro Ala Ser His Thr
        195                 200                 205

Pro Ala Gln Ala Arg Ala Leu Tyr Thr Arg His Leu Leu Arg Leu Thr
    210                 215                 220

Ala Asp Thr Arg Ala Ala Ala Val Pro Leu Asp Pro Val Leu Asn Pro
225                 230                 235                 240

Gln Thr Asn Ala Pro Thr Pro Leu Gly Gly Ala Val Leu Arg Ala Thr
                245                 250                 255

Ser Pro Met His Met Gln Tyr Leu Arg Asn Met Gly Val Gly Ser Ser
            260                 265                 270

Leu Ser Val Ser Val Val Gly Gly Gln Leu Trp Gly Leu Ile Val
        275                 280                 285
```

```
Cys His His Gln Thr Pro Tyr Val Leu Pro Pro Asp Leu Arg Thr Thr
    290                 295                 300

Leu Glu Tyr Leu Gly Arg Leu Leu Ser Leu Gln Val Gln Val Lys Glu
305                 310                 315                 320

Ala Glu Phe His His His His His His
                325

<210> SEQ ID NO 4
<211> LENGTH: 329
<212> TYPE: PRT
<213> ORGANISM: Artificial Sequence
<220> FEATURE:
<223> OTHER INFORMATION: synthetic infrared fluorescent protein (IFP),
      truncated bacteriophytochrome chromophore-binding domain from
      Deinococcus radiodurans with 5 mutations,
      DrCBD/G119A/V186M/D207H/I208T/A288V (IFP1.02 his6)

<400> SEQUENCE: 4

Met Ser Arg Asp Pro Leu Pro Phe Phe Pro Leu Tyr Leu Gly Gly
1               5                   10                  15

Pro Glu Ile Thr Thr Glu Asn Cys Glu Arg Glu Pro Ile His Ile Pro
                20                  25                  30

Gly Ser Ile Gln Pro His Gly Ala Leu Leu Thr Ala Asp Gly His Ser
            35                  40                  45

Gly Glu Val Leu Gln Met Ser Leu Asn Ala Ala Thr Phe Leu Gly Gln
    50                  55                  60

Glu Pro Thr Val Leu Arg Gly Gln Thr Leu Ala Ala Leu Leu Pro Glu
65                  70                  75                  80

Gln Trp Pro Ala Leu Gln Ala Ala Leu Pro Pro Gly Cys Pro Asp Ala
                85                  90                  95

Leu Gln Tyr Arg Ala Thr Leu Asp Trp Pro Ala Ala Gly His Leu Ser
            100                 105                 110

Leu Thr Val His Arg Val Ala Glu Leu Leu Ile Leu Glu Phe Glu Pro
        115                 120                 125

Thr Glu Ala Trp Asp Ser Thr Gly Pro His Ala Leu Arg Asn Ala Met
130                 135                 140

Phe Ala Leu Glu Ser Ala Pro Asn Leu Arg Ala Leu Ala Glu Val Ala
145                 150                 155                 160

Thr Gln Thr Val Arg Glu Leu Thr Gly Phe Asp Arg Val Met Leu Tyr
                165                 170                 175

Lys Phe Ala Pro Asp Ala Thr Gly Glu Met Ile Ala Glu Ala Arg Arg
            180                 185                 190

Glu Gly Leu His Ala Phe Leu Gly His Arg Phe Pro Ala Ser His His Thr
        195                 200                 205

Pro Ala Gln Ala Arg Ala Leu Tyr Thr Arg His Leu Leu Arg Leu Thr
    210                 215                 220

Ala Asp Thr Arg Ala Ala Ala Val Pro Leu Asp Pro Val Leu Asn Pro
225                 230                 235                 240

Gln Thr Asn Ala Pro Thr Pro Leu Gly Gly Ala Val Leu Arg Ala Thr
                245                 250                 255

Ser Pro Met His Met Gln Tyr Leu Arg Asn Met Gly Val Gly Ser Ser
            260                 265                 270

Leu Ser Val Ser Val Val Val Gly Gly Gln Leu Trp Gly Leu Ile Val
        275                 280                 285

Cys His His Gln Thr Pro Tyr Val Leu Pro Pro Asp Leu Arg Thr Thr
    290                 295                 300
```

Leu Glu Tyr Leu Gly Arg Leu Leu Ser Leu Gln Val Gln Val Lys Glu
305                 310                 315                 320

Ala Glu Phe His His His His His His
            325

<210> SEQ ID NO 5
<211> LENGTH: 987
<212> TYPE: DNA
<213> ORGANISM: Artificial Sequence
<220> FEATURE:
<223> OTHER INFORMATION: synthetic infrared fluorescent protein (IFP),
      truncated bacteriophytochrome chromophore-binding domain from
      Deinococcus radiodurans with a single mutation, DrCBD/D207H
      (IFP1.0 his6) cDNA codon optimized for E. coli

<400> SEQUENCE: 5
atgtctcgtg atccgctgcc gttttttccg ccgctgtatc tgggtggtcc ggagatcacc      60
actgaaaact gtgagcgtga accgattcat atcccgggtt ccatccagcc gcacggtgca     120
ctgctgaccg cagatggcca ctctggcgaa gtgctgcaga tgtctctgaa cgctgcaact     180
ttcctgggtc aggagccgac cgttctgcgt ggccagaccc tggcggctct gctgccggaa     240
cagtggccgg ctctgcaggc ggctctgccg ccgggttgcc ggatgcgct gcagtaccgc      300 gctaccctgg attggccggc agctggtcac ctgtccctga ccgttcaccg tgtgggtgaa     360
ctgctgatcc tggaatttga accgaccgaa gcatgggatt ccaccggccc gcacgcactg     420
cgtaacgcta tgtttgcact ggaatccgca ccgaacctgc gtgctctggc ggaggttgct     480
actcagaccg ttcgcgaact gactggtttt gatcgcgtaa tgctgtacaa gttcgcaccg     540
gatgcgactg gtgaagtgat cgcggaagct cgtcgcgaag gtctgcatgc ttttctgggt     600
caccgtttcc cggctagcca catcccggcg caggctcgcg cactgtacac tcgtcacctg     660
ctgcgtctga ctgcggacac ccgcgcagct gcggttccgc tggacccggt tctgaacccg     720
cagaccaacg cgccgacccc gctgggcggc gcggttctgc gtgcgaccag cccgatgcat     780
atgcagtacc tgcgtaacat gggtgttggc agctccctgt ctgtgagcgt ggtagttggc     840
ggtcagctgt ggggtctgat cgcttgtcac caccagactc cgtacgttct gccgccggat     900
ctgcgcacca ccctggagta cctgggtcgt ctgctgagcc tgcaggtaca ggttaaagag     960
gcggaattcc atcatcacca tcaccat                                         987

<210> SEQ ID NO 6
<211> LENGTH: 987
<212> TYPE: DNA
<213> ORGANISM: Artificial Sequence
<220> FEATURE:
<223> OTHER INFORMATION: synthetic infrared fluorescent protein (IFP),
      truncated bacteriophytochrome chromophore-binding domain from
      Deinococcus radiodurans with 3 mutations, DrCBD/D207H/I208T/A288V
      (IFP1.01 his6) cDNA codon optimized for E. coli

<400> SEQUENCE: 6
atgtctcgtg atccgctgcc gttttttccg ccgctgtatc tgggtggtcc ggagatcacc      60
actgaaaact gtgagcgtga accgattcat atcccgggtt ccatccagcc gcacggtgca     120
ctgctgaccg cagatggcca ctctggcgaa gtgctgcaga tgtctctgaa cgctgcaact     180
ttcctgggtc aggagccgac cgttctgcgt ggccagaccc tggcggctct gctgccggaa     240
cagtggccgg ctctgcaggc ggctctgccg ccgggttgcc ggatgcgct gcagtaccgc      300 gctaccctgg attggccggc agctggtcac ctgtccctga ccgttcaccg tgtgggtgaa     360
ctgctgatcc tggaatttga accgaccgaa gcatgggatt ccaccggccc gcacgcactg     420

```
cgtaacgcta tgtttgcact ggaatccgca ccgaacctgc gtgctctggc ggaggttgct      480
actcagaccg ttcgcgaact gactggtttt gatcgcgtaa tgctgtacaa gttcgcaccg      540
gatgcgactg gtgaagtgat cgcggaagct cgtcgcgaag gtctgcatgc ttttctgggt      600
caccgtttcc cggctagcca caccccggcg caggctcgcg cactgtacac tcgtcacctg      660
ctgcgtctga ctgcggacac ccgcgcagct gcggttccgc tggacccggt tctgaacccg      720
cagaccaacg cgccgacccc gctgggcggc gcggttctgc gtgcgaccag cccgatgcat      780
atgcagtacc tgcgtaacat gggtgttggc agctccctgt ctgtgagcgt ggtagttggc      840
ggtcagctgt ggggtctgat cgtgtgtcac caccagactc cgtacgttct gccgccggat      900
ctgcgcacca ccctggagta cctgggtcgt ctgctgagcc tgcaggtaca ggttaaagag      960
gcggaattcc atcatcacca tcaccat                                         987
```

<210> SEQ ID NO 7
<211> LENGTH: 987
<212> TYPE: DNA
<213> ORGANISM: Artificial Sequence
<220> FEATURE:
<223> OTHER INFORMATION: synthetic infrared fluorescent protein (IFP),
      truncated bacteriophytochrome chromophore-binding domain from
      Deinococcus radiodurans with 5 mutations, DrCBD/G119A/V186M/D207H/
      I208T/A288V (IFP1.0 his6) cDNA codon optimized for E. coli

<400> SEQUENCE: 7

```
atgtctcgtg atccgctgcc gttttttcccg ccgctgtatc tgggtggtcc ggagatcacc      60 actgaaaaact gtgagcgtga accgattcat atcccgggtt ccatccagcc gcacggtgca     120
ctgctgaccg cagatggcca ctctggcgaa gtgctgcaga tgtctctgaa cgctgcaact     180
ttcctgggtc aggagccgac cgttctgcgt ggccagaccc tggcggctct gctgccggaa     240
cagtggccgg ctctgcaggc ggctctgccg ccgggttgcc cggatgcgct gcagtaccgc     300
gctaccctgg attggccggc agctggtcac ctgtccctga ccgttcaccg tgtggctgaa     360
ctgctgatcc tggaatttga accgaccgaa gcatgggatt ccaccggccc gcacgcactg     420
cgtaacgcta tgtttgcact ggaatccgca ccgaacctgc gtgctctggc ggaggttgct     480
actcagaccg ttcgcgaact gactggtttt gatcgcgtaa tgctgtacaa gttcgcaccg     540
gatgcgactg gtgaaatgat cgcggaagct cgtcgcgaag gtctgcatgc ttttctgggt     600
caccgtttcc cggctagcca caccccggcg caggctcgcg cactgtacac tcgtcacctg     660
ctgcgtctga ctgcggacac ccgcgcagct gcggttccgc tggacccggt tctgaacccg     720
cagaccaacg cgccgacccc gctgggcggc gcggttctgc gtgcgaccag cccgatgcat     780
atgcagtacc tgcgtaacat gggtgttggc agctccctgt ctgtgagcgt ggtagttggc     840
ggtcagctgt ggggtctgat cgtgtgtcac caccagactc cgtacgttct gccgccggat     900
ctgcgcacca ccctggagta cctgggtcgt ctgctgagcc tgcaggtaca ggttaaagag     960
gcggaattcc atcatcacca tcaccat                                         987
```

<210> SEQ ID NO 8
<211> LENGTH: 1044
<212> TYPE: DNA
<213> ORGANISM: Artificial Sequence
<220> FEATURE:
<223> OTHER INFORMATION: synthetic infrared fluorescent protein (IFP),
      truncated bacteriophytochrome chromophore-binding domain from
      Deinococcus radiodurans with a single mutation, DrCBD/D207H
      (IFP1.0 his6) cDNA codon optimized for mammals

<400> SEQUENCE: 8

-continued

```
atgagccggg accctctgcc attctttcca cctctgtacc tgggcggccc tgagattaca    60
accgagaact gcgagagaga gcctatccac attcctgggt ccatccagcc acacggggct   120
ctgctcacag ctgacggcca ctccggagag gtgctccaaa tgtccctgaa tgccgctacc   180
ttcctgggcc aggagcctac tgtgctgcgg ggcagaccc tggctgccct gctccccgag    240
cagtggccag ccctgcaggc agccctgccc ccaggatgtc cagatgccct ccaatacagg   300
gccaccctcg actggccagc tgctgggcac ctcagcctga ctgtgcatcg ggtggggaa    360
ctcctgatcc tggagttcga acctaccgag gcctgggaca gcactggccc tcacgccctg   420
aggaacgcca tgtttgctct ggaaagcgct ccaaacctgc gggctctggc cgaagtcgca   480
acacaaactg tgagagaact gactggcttc gatcgggtga tgctgtacaa atttgcccct   540
gacgccactg gagaggtgat tgctgaggcc agacgggagg cctccacgc ttttctgggc    600
cacaggtttc ccgcatccca catccctgca caagctaggg ccctctacac aagacacctg   660
ctccggctga ccgcagacac cagggctgca gcagtgcccc tcgacccgt gctgaatccc    720
cagacaaatg ctcctacacc tctgggcgga gctgtcctca gagctacatc cccaatgcac   780
atgcagtacc tgaggaatat gggagtgggc tcctccctga cgtcagcgt cgtggtcggc    840
ggccagctgt ggggactgat tgcctgccac catcagacac cctacgtgct gccaccagat   900
ctgcggacca ccctggagta tctggggagg ctcctgtccc tgcaggtgca ggtgaaagaa   960
gccgaattct gcagatatcc atcacactgg cggccgctcg agcatgcatc tagagggccc  1020
tattctatag tgtcacctaa atgc                                         1044
```

<210> SEQ ID NO 9
<211> LENGTH: 963
<212> TYPE: DNA
<213> ORGANISM: Artificial Sequence
<220> FEATURE:
<223> OTHER INFORMATION: synthetic infrared fluorescent protein (IFP),
truncated bacteriophytochrome chromophore-binding domain from
Deinococcus radiodurans with 3 mutations, DrCBD/D207H/I208T/A288V
(IFP1.01 his6) cDNA codon optimized for mammals

<400> SEQUENCE: 9

```
atgagccggg accctctgcc attctttcca cctctgtacc tgggcggccc tgagattaca    60
accgagaact gcgagagaga gcctatccac attcctgggt ccatccagcc acacggggct   120
ctgctcacag ctgacggcca ctccggagag gtgctccaaa tgtccctgaa tgccgctacc   180
ttcctgggcc aggagcctac tgtgctgcgg ggcagaccc tggctgccct gctccccgag    240
cagtggccag ccctgcaggc agccctgccc ccaggatgtc cagatgccct ccaatacagg   300
gccaccctcg actggccagc tgctgggcac ctcagcctga ctgtgcatcg ggtggggaa    360
ctcctgatcc tggagttcga acctaccgag gcctgggaca gcactggccc tcacgccctg   420
aggaacgcca tgtttgctct ggaaagcgct ccaaacctgc gggctctggc cgaagtcgca   480
acacaaactg tgagagaact gactggcttc gatcgggtga tgctgtacaa atttgcccct   540
gacgccactg gagaggtgat tgctgaggcc agacgggagg cctccacgc ttttctgggc    600
cacaggtttc ccgcatccca caccctgca caagctaggg ccctctacac aagacacctg    660
ctccggctga ccgcagacac cagggctgca gcagtgcccc tcgacccgt gctgaatccc    720
cagacaaatg ctcctacacc tctgggcgga gctgtcctca gagctacatc cccaatgcac   780
atgcagtacc tgaggaatat gggagtgggc tcctccctga cgtcagcgt cgtggtcggc    840
ggccagctgt ggggactgat tgcctgccac catcagacac cctacgtgct gccaccagat   900
ctgcggacca ccctggagta tctggggagg ctcctgtccc tgcaggtgca ggtgaaagaa   960
```

-continued

```
gcc                                                             963
```

<210> SEQ ID NO 10
<211> LENGTH: 963
<212> TYPE: DNA
<213> ORGANISM: Artificial Sequence
<220> FEATURE:
<223> OTHER INFORMATION: synthetic infrared fluorescent protein (IFP),
      truncated bacteriophytochrome chromophore-binding domain from
      Deinococcus radiodurans with 5 mutations, DrCBD/G119A/V186M/D207H/
      I208T/A288V (IFP1.02 his6) cDNA codon optimized for mammals

<400> SEQUENCE: 10

```
atgagccggg accctctgcc attctttcca cctctgtacc tgggcggccc tgagattaca      60
accgagaact gcgagagaga gcctatccac attcctgggt ccatccagcc acacggggct    120
ctgctcacag ctgacggcca ctccggagag gtgctccaaa tgtccctgaa tgccgctacc    180
ttcctgggcc aggagcctac tgtgctgcgg gggcagaccc tggctgccct gctccccgag    240
cagtggccag ccctgcaggc agccctgccc ccaggatgtc cagatgccct ccaatacagg    300
gccaccctcg actggccagc tgctgggcac ctcagcctga ctgtgcatcg ggtggcggaa    360
ctcctgatcc tggagttcga acctaccgag gcctgggaca gcactggccc tcacgccctg    420
aggaacgcca tgtttgctct ggaaagcgct ccaaacctgc gggctctggc cgaagtcgca    480
acacaaactg tgagagaact gactggcttc gatcgggtga tgctgtacaa atttgcccct    540
gacgccactg agagatgat tgctgaggcc agacgggagg cctccacgc ttttctgggc     600
cacaggtttc ccgcatccca caccctgca caagctaggg ccctctacac aagacacctg    660
ctccggctga ccgcagacac cagggctgca gcagtgcccc tcgacccgt gctgaatccc    720
cagacaaatg ctcctacacc tctgggcgga gctgtcctca gagctacatc cccaatgcac    780
atgcagtacc tgaggaatat gggagtgggc tcctccctga gcgtcagcgt cgtggtcggc    840
ggccagctgt ggggactgat tgtctgccac catcagacac cctacgtgct gccaccagat    900
ctgcggacca ccctggagta tctggggagg ctcctgtccc tgcaggtgca ggtgaaagaa    960
gcc                                                                  963
```

<210> SEQ ID NO 11
<211> LENGTH: 348
<212> TYPE: PRT
<213> ORGANISM: Artificial Sequence
<220> FEATURE:
<223> OTHER INFORMATION: synthetic infrared fluorescent protein (IFP),
      truncated bacteriophytochrome chromophore-binding domain from
      Deinococcus radiodurans with a single mutation, DrCBD/D207H
      (IFP1.0 his6) with C-terminal extension from pcDNA3 vector

<400> SEQUENCE: 11

```
Met Ser Arg Asp Pro Leu Pro Phe Phe Pro Pro Leu Tyr Leu Gly Gly
1               5                   10                  15

Pro Glu Ile Thr Thr Glu Asn Cys Glu Arg Glu Pro Ile His Ile Pro
            20                  25                  30

Gly Ser Ile Gln Pro His Gly Ala Leu Leu Thr Ala Asp Gly His Ser
        35                  40                  45

Gly Glu Val Leu Gln Met Ser Leu Asn Ala Ala Thr Phe Leu Gly Gln
    50                  55                  60

Glu Pro Thr Val Leu Arg Gly Gln Thr Leu Ala Ala Leu Leu Pro Glu
65                  70                  75                  80

Gln Trp Pro Ala Leu Gln Ala Ala Leu Pro Pro Gly Cys Pro Asp Ala
                85                  90                  95
```

```
Leu Gln Tyr Arg Ala Thr Leu Asp Trp Pro Ala Ala Gly His Leu Ser
                100                 105                 110

Leu Thr Val His Arg Val Gly Glu Leu Ile Leu Glu Phe Glu Pro
        115                 120                 125

Thr Glu Ala Trp Asp Ser Thr Gly Pro His Ala Leu Arg Asn Ala Met
130                 135                 140

Phe Ala Leu Glu Ser Ala Pro Asn Leu Arg Ala Leu Ala Glu Val Ala
145                 150                 155                 160

Thr Gln Thr Val Arg Glu Leu Thr Gly Phe Asp Arg Val Met Leu Tyr
                165                 170                 175

Lys Phe Ala Pro Asp Ala Thr Gly Glu Val Ile Ala Glu Ala Arg Arg
                180                 185                 190

Glu Gly Leu His Ala Phe Leu Gly His Arg Phe Pro Ala Ser His Ile
                195                 200                 205

Pro Ala Gln Ala Arg Ala Leu Tyr Thr Arg His Leu Leu Arg Leu Thr
            210                 215                 220

Ala Asp Thr Arg Ala Ala Val Pro Leu Asp Pro Val Leu Asn Pro
225                 230                 235                 240

Gln Thr Asn Ala Pro Thr Pro Leu Gly Gly Ala Val Leu Arg Ala Thr
                245                 250                 255

Ser Pro Met His Met Gln Tyr Leu Arg Asn Met Gly Val Gly Ser Ser
            260                 265                 270

Leu Ser Val Ser Val Val Gly Gly Gln Leu Trp Gly Leu Ile Ala
            275                 280                 285

Cys His His Gln Thr Pro Tyr Val Leu Pro Pro Asp Leu Arg Thr Thr
        290                 295                 300

Leu Glu Tyr Leu Gly Arg Leu Leu Ser Leu Gln Val Gln Val Lys Glu
305                 310                 315                 320

Ala Glu Phe Cys Arg Tyr Pro Ser His Trp Arg Pro Leu Glu His Ala
                325                 330                 335

Ser Arg Gly Pro Tyr Ser Ile Val Ser Pro Lys Cys
            340                 345

<210> SEQ ID NO 12
<211> LENGTH: 321
<212> TYPE: PRT
<213> ORGANISM: Artificial Sequence
<220> FEATURE:
<223> OTHER INFORMATION: synthetic infrared fluorescent protein (IFP),
      truncated bacteriophytochrome chromophore-binding
      domain from Deinococcus radiodurans with 3
      mutations, DrCBD/D207H/I208T/A288V (IFP1.01 his6)

<400> SEQUENCE: 12

Met Ser Arg Asp Pro Leu Pro Phe Phe Pro Pro Leu Tyr Leu Gly Gly
1               5                   10                  15

Pro Glu Ile Thr Thr Glu Asn Cys Glu Arg Glu Pro Ile His Ile Pro
            20                  25                  30

Gly Ser Ile Gln Pro His Gly Ala Leu Leu Thr Ala Asp Gly His Ser
        35                  40                  45

Gly Glu Val Leu Gln Met Ser Leu Asn Ala Ala Thr Phe Leu Gly Gln
    50                  55                  60

Glu Pro Thr Val Leu Arg Gly Gln Thr Leu Ala Ala Leu Leu Pro Glu
65                  70                  75                  80

Gln Trp Pro Ala Leu Gln Ala Ala Leu Pro Pro Gly Cys Pro Asp Ala
                85                  90                  95
```

```
Leu Gln Tyr Arg Ala Thr Leu Asp Trp Pro Ala Ala Gly His Leu Ser
                100                 105                 110

Leu Thr Val His Arg Val Gly Glu Leu Leu Ile Leu Glu Phe Glu Pro
            115                 120                 125

Thr Glu Ala Trp Asp Ser Thr Gly Pro His Ala Leu Arg Asn Ala Met
130                 135                 140

Phe Ala Leu Glu Ser Ala Pro Asn Leu Arg Ala Leu Ala Glu Val Ala
145                 150                 155                 160

Thr Gln Thr Val Arg Glu Leu Thr Gly Phe Asp Arg Val Met Leu Tyr
                165                 170                 175

Lys Phe Ala Pro Asp Ala Thr Gly Glu Val Ile Ala Glu Ala Arg Arg
            180                 185                 190

Glu Gly Leu His Ala Phe Leu Gly His Arg Phe Pro Ala Ser His Thr
        195                 200                 205

Pro Ala Gln Ala Arg Ala Leu Tyr Thr Arg His Leu Arg Leu Thr
210                 215                 220

Ala Asp Thr Arg Ala Ala Val Pro Leu Asp Pro Val Leu Asn Pro
225                 230                 235                 240

Gln Thr Asn Ala Pro Thr Pro Leu Gly Gly Ala Val Leu Arg Ala Thr
                245                 250                 255

Ser Pro Met His Met Gln Tyr Leu Arg Asn Met Gly Val Gly Ser Ser
            260                 265                 270

Leu Ser Val Ser Val Val Gly Gln Leu Trp Gly Leu Ile Val
275                 280                 285

Cys His His Gln Thr Pro Tyr Val Leu Pro Pro Asp Leu Arg Thr Thr
    290                 295                 300

Leu Glu Tyr Leu Gly Arg Leu Leu Ser Leu Gln Val Gln Val Lys Glu
305                 310                 315                 320

Ala
```

<210> SEQ ID NO 13
<211> LENGTH: 321
<212> TYPE: PRT
<213> ORGANISM: Artificial Sequence
<220> FEATURE:
<223> OTHER INFORMATION: synthetic infrared fluorescent protein (IFP), truncated bacteriophytochrome chromophore-binding domain from Deinococcus radiodurans with 5 mutations, DrCBD/G119A/V186M/D207H/ I208T/A288V (IFP1.02 his6) with C-terminal extension from pcDNA3 vector

<400> SEQUENCE: 13

```
Met Ser Arg Asp Pro Leu Pro Phe Phe Pro Pro Leu Tyr Leu Gly Gly
1               5                   10                  15

Pro Glu Ile Thr Thr Glu Asn Cys Glu Arg Glu Pro Ile His Ile Pro
            20                  25                  30

Gly Ser Ile Gln Pro His Gly Ala Leu Leu Thr Ala Asp Gly His Ser
        35                  40                  45

Gly Glu Val Leu Gln Met Ser Leu Asn Ala Ala Thr Phe Leu Gly Gln
    50                  55                  60

Glu Pro Thr Val Leu Arg Gly Gln Thr Leu Ala Ala Leu Leu Pro Glu
65                  70                  75                  80

Gln Trp Pro Ala Leu Gln Ala Ala Leu Pro Pro Gly Cys Pro Asp Ala
                85                  90                  95

Leu Gln Tyr Arg Ala Thr Leu Asp Trp Pro Ala Ala Gly His Leu Ser
            100                 105                 110

Leu Thr Val His Arg Val Ala Glu Leu Leu Ile Leu Glu Phe Glu Pro
```

```
                    115                 120                 125
Thr Glu Ala Trp Asp Ser Thr Gly Pro His Ala Leu Arg Asn Ala Met
            130                 135                 140

Phe Ala Leu Glu Ser Ala Pro Asn Leu Arg Ala Leu Ala Glu Val Ala
145                 150                 155                 160

Thr Gln Thr Val Arg Glu Leu Thr Gly Phe Asp Arg Val Met Leu Tyr
                165                 170                 175

Lys Phe Ala Pro Asp Ala Thr Gly Glu Met Ile Ala Glu Ala Arg Arg
            180                 185                 190

Glu Gly Leu His Ala Phe Leu Gly His Arg Phe Pro Ala Ser His Thr
                195                 200                 205

Pro Ala Gln Ala Arg Ala Leu Tyr Thr Arg His Leu Leu Arg Leu Thr
            210                 215                 220

Ala Asp Thr Arg Ala Ala Val Pro Leu Asp Pro Val Leu Asn Pro
225                 230                 235                 240

Gln Thr Asn Ala Pro Thr Pro Leu Gly Gly Ala Val Leu Arg Ala Thr
                245                 250                 255

Ser Pro Met His Met Gln Tyr Leu Arg Asn Met Gly Val Gly Ser Ser
            260                 265                 270

Leu Ser Val Ser Val Val Gly Gly Gln Leu Trp Gly Leu Ile Val
            275                 280                 285

Cys His His Gln Thr Pro Tyr Val Leu Pro Pro Asp Leu Arg Thr Thr
            290                 295                 300

Leu Glu Tyr Leu Gly Arg Leu Leu Ser Leu Gln Val Gln Val Lys Glu
305                 310                 315                 320

Ala

<210> SEQ ID NO 14
<211> LENGTH: 321
<212> TYPE: PRT
<213> ORGANISM: Deinococcus radiodurans
<220> FEATURE:
<223> OTHER INFORMATION: infrared fluorescent protein (IFP), truncated
      bacteriophytochrome (DrBphP) chromophore-binding
      domain from Deinococcus radiodurans, DrCBD

<400> SEQUENCE: 14

Met Ser Arg Asp Pro Leu Pro Phe Phe Pro Pro Leu Tyr Leu Gly Gly
1               5                   10                  15

Pro Glu Ile Thr Thr Glu Asn Cys Glu Arg Glu Pro Ile His Ile Pro
            20                  25                  30

Gly Ser Ile Gln Pro His Gly Ala Leu Leu Thr Ala Asp Gly His Ser
        35                  40                  45

Gly Glu Val Leu Gln Met Ser Leu Asn Ala Ala Thr Phe Leu Gly Gln
    50                  55                  60

Glu Pro Thr Val Leu Arg Gly Gln Thr Leu Ala Ala Leu Leu Pro Glu
65                  70                  75                  80

Gln Trp Pro Ala Leu Gln Ala Ala Leu Pro Pro Gly Cys Pro Asp Ala
                85                  90                  95

Leu Gln Tyr Arg Ala Thr Leu Asp Trp Pro Ala Ala Gly His Leu Ser
            100                 105                 110

Leu Thr Val His Arg Val Gly Glu Leu Leu Ile Leu Glu Phe Glu Pro
        115                 120                 125

Thr Glu Ala Trp Asp Ser Thr Gly Pro His Ala Leu Arg Asn Ala Met
    130                 135                 140

Phe Ala Leu Glu Ser Ala Pro Asn Leu Arg Ala Leu Ala Glu Val Ala
```

```
            145                 150                 155                 160
Thr Gln Thr Val Arg Glu Leu Thr Gly Phe Asp Arg Val Met Leu Tyr
                165                 170                 175
Lys Phe Ala Pro Asp Ala Thr Gly Glu Val Ile Ala Glu Ala Arg Arg
            180                 185                 190
Glu Gly Leu His Ala Phe Leu Gly His Arg Phe Pro Ala Ser Asp Ile
            195                 200                 205
Pro Ala Gln Ala Arg Ala Leu Tyr Thr Arg His Leu Leu Arg Leu Thr
            210                 215                 220
Ala Asp Thr Arg Ala Ala Val Pro Leu Asp Pro Val Leu Asn Pro
225                 230                 235                 240
Gln Thr Asn Ala Pro Thr Pro Leu Gly Gly Ala Val Leu Arg Ala Thr
                245                 250                 255
Ser Pro Met His Met Gln Tyr Leu Arg Asn Met Gly Val Gly Ser Ser
            260                 265                 270
Leu Ser Val Ser Val Val Gly Gly Gln Leu Trp Gly Leu Ile Ala
            275                 280                 285
Cys His His Gln Thr Pro Tyr Val Leu Pro Pro Asp Leu Arg Thr Thr
            290                 295                 300
Leu Glu Tyr Leu Gly Arg Leu Leu Ser Leu Gln Val Gln Val Lys Glu
305                 310                 315                 320
Ala

<210> SEQ ID NO 15
<211> LENGTH: 329
<212> TYPE: PRT
<213> ORGANISM: Artificial Sequence
<220> FEATURE:
<223> OTHER INFORMATION: synthetic infrared fluorescent protein (IFP),
      truncated bacteriophytochrome chromophore-binding
      domain from Deinococcus radiodurans, IFP1.4 S2A
      his6

<400> SEQUENCE: 15

Met Ala Arg Asp Pro Leu Pro Phe Phe Pro Leu Tyr Leu Gly Gly
1               5                   10                  15
Pro Glu Ile Thr Thr Glu Asn Cys Glu Arg Glu Pro Ile His Ile Pro
            20                  25                  30
Gly Ser Ile Gln Pro His Gly Ala Leu Leu Thr Ala Asp Gly His Ser
            35                  40                  45
Gly Glu Val Leu Gln Val Ser Leu Asn Ala Ala Thr Phe Leu Gly Gln
            50                  55                  60
Glu Pro Thr Val Leu Arg Gly Gln Thr Leu Ala Ala Leu Leu Pro Glu
65                  70                  75                  80
Gln Trp Pro Ala Leu Gln Ala Ala Leu Pro Pro Gly Cys Pro Asp Ala
                85                  90                  95
Leu Gln Tyr Arg Ala Thr Leu Asp Trp Pro Ala Ala Gly His Leu Ser
            100                 105                 110
Leu Thr Val His Arg Val Ala Glu Leu Leu Ile Leu Glu Phe Glu Pro
            115                 120                 125
Thr Glu Ala Trp Asp Ser Ile Gly Pro His Ala Leu Arg Asn Ala Met
            130                 135                 140
Phe Ala Leu Glu Ser Ala Pro Asn Leu Arg Ala Leu Ala Glu Val Ala
145                 150                 155                 160
Thr Gln Thr Val Arg Glu Leu Thr Gly Phe Asp Arg Val Met Leu Tyr
                165                 170                 175
```

```
Lys Phe Ala Pro Asp Ala Thr Gly Glu Met Ile Ala Glu Ala Arg Arg
            180                 185                 190

Glu Gly Met Gln Ala Phe Leu Gly His Arg Phe Pro Ala Ser His Thr
        195                 200                 205

Pro Ala Gln Ala Arg Ala Leu Tyr Thr Arg His Leu Leu Arg Leu Thr
    210                 215                 220

Ala Asp Thr Arg Ala Ala Val Pro Leu Asp Pro Val Leu Asn Pro
225                 230                 235                 240

Gln Thr Asn Ala Pro Thr Pro Leu Gly Gly Ala Val Leu Arg Ala Thr
                245                 250                 255

Ser Pro Met His Met Gln Tyr Leu Arg Asn Met Gly Val Gly Ser Ser
            260                 265                 270

Leu Ser Val Ser Val Val Gly Gly Gln Leu Trp Gly Leu Ile Val
        275                 280                 285

Cys His His Gln Thr Pro Tyr Val Leu Pro Pro Asp Leu Arg Thr Thr
    290                 295                 300

Leu Glu Glu Leu Gly Arg Lys Leu Ser Gly Gln Val Gln Arg Lys Glu
305                 310                 315                 320

Ala Glu Phe His His His His His His
                325

<210> SEQ ID NO 16
<211> LENGTH: 321
<212> TYPE: PRT
<213> ORGANISM: Artificial Sequence
<220> FEATURE:
<223> OTHER INFORMATION: synthetic infrared fluorescent protein (IFP),
      truncated bacteriophytochrome chromophore-binding
      domain from Deinococcus radiodurans with a single
      mutation, DrCBD/D207H (IFP1.0)

<400> SEQUENCE: 16

Met Ser Arg Asp Pro Leu Pro Phe Phe Pro Pro Leu Tyr Leu Gly Gly
1               5                   10                  15

Pro Glu Ile Thr Thr Glu Asn Cys Glu Arg Glu Pro Ile His Ile Pro
            20                  25                  30

Gly Ser Ile Gln Pro His Gly Ala Leu Leu Thr Ala Asp Gly His Ser
        35                  40                  45

Gly Glu Val Leu Gln Met Ser Leu Asn Ala Ala Thr Phe Leu Gly Gln
    50                  55                  60

Glu Pro Thr Val Leu Arg Gly Gln Thr Leu Ala Ala Leu Leu Pro Glu
65                  70                  75                  80

Gln Trp Pro Ala Leu Gln Ala Ala Leu Pro Pro Gly Cys Pro Asp Ala
                85                  90                  95

Leu Gln Tyr Arg Ala Thr Leu Asp Trp Pro Ala Ala Gly His Leu Ser
            100                 105                 110

Leu Thr Val His Arg Val Gly Glu Leu Leu Ile Leu Glu Phe Glu Pro
        115                 120                 125

Thr Glu Ala Trp Asp Ser Thr Gly Pro His Ala Leu Arg Asn Ala Met
    130                 135                 140

Phe Ala Leu Glu Ser Ala Pro Asn Leu Arg Ala Leu Ala Glu Val Ala
145                 150                 155                 160

Thr Gln Thr Val Arg Glu Leu Thr Gly Phe Asp Arg Val Met Leu Tyr
                165                 170                 175

Lys Phe Ala Pro Asp Ala Thr Gly Glu Val Ile Ala Glu Ala Arg Arg
            180                 185                 190

Glu Gly Leu His Ala Phe Leu Gly His Arg Phe Pro Ala Ser His Ile
```

```
                 195                 200                 205
Pro Ala Gln Ala Arg Ala Leu Tyr Thr Arg His Leu Leu Arg Leu Thr
    210                 215                 220
Ala Asp Thr Arg Ala Ala Val Pro Leu Asp Pro Val Leu Asn Pro
225                 230                 235                 240
Gln Thr Asn Ala Pro Thr Pro Leu Gly Gly Ala Val Leu Arg Ala Thr
                245                 250                 255
Ser Pro Met His Met Gln Tyr Leu Arg Asn Met Gly Val Gly Ser Ser
            260                 265                 270
Leu Ser Val Ser Val Val Gly Gly Gln Leu Trp Gly Leu Ile Ala
        275                 280                 285
Cys His His Gln Thr Pro Tyr Val Leu Pro Pro Asp Leu Arg Thr Thr
    290                 295                 300
Leu Glu Tyr Leu Gly Arg Leu Leu Ser Leu Gln Val Gln Val Lys Glu
305                 310                 315                 320
Ala

<210> SEQ ID NO 17
<211> LENGTH: 321
<212> TYPE: PRT
<213> ORGANISM: Artificial Sequence
<220> FEATURE:
<223> OTHER INFORMATION: synthetic infrared fluorescent protein (IFP),
      truncated bacteriophytochrome chromophore-binding
      domain from Deinococcus radiodurans (DrCDB),
      IFP1.1

<400> SEQUENCE: 17

Met Ser Arg Asp Pro Leu Pro Phe Phe Pro Pro Leu Tyr Leu Gly Gly
1               5                   10                  15
Pro Glu Ile Thr Thr Glu Asn Cys Glu Arg Glu Pro Ile His Ile Pro
            20                  25                  30
Gly Ser Ile Gln Pro His Gly Ala Leu Leu Thr Ala Asp Gly His Ser
        35                  40                  45
Gly Glu Val Leu Gln Met Ser Leu Asn Ala Ala Thr Phe Leu Gly Gln
    50                  55                  60
Glu Pro Thr Val Leu Arg Gly Gln Thr Leu Ala Ala Leu Leu Pro Glu
65                  70                  75                  80
Gln Trp Pro Ala Leu Gln Ala Ala Leu Pro Pro Gly Cys Pro Asp Ala
                85                  90                  95
Leu Gln Tyr Arg Ala Thr Leu Asp Trp Pro Ala Ala Gly His Leu Ser
            100                 105                 110
Leu Thr Val His Arg Val Gly Glu Leu Leu Ile Leu Glu Phe Glu Pro
        115                 120                 125
Thr Glu Ala Trp Asp Ser Thr Gly Pro His Ala Leu Arg Asn Ala Met
    130                 135                 140
Phe Ala Leu Glu Ser Ala Pro Asn Leu Arg Ala Leu Ala Glu Val Ala
145                 150                 155                 160
Thr Gln Thr Val Arg Glu Leu Thr Gly Phe Asp Arg Val Met Leu Tyr
                165                 170                 175
Lys Phe Ala Pro Asp Ala Thr Gly Glu Met Ile Ala Glu Ala Arg Arg
            180                 185                 190
Glu Gly Leu His Ala Phe Leu Gly His Arg Phe Pro Ala Ser His Thr
        195                 200                 205
Pro Ala Gln Ala Arg Ala Leu Tyr Thr Arg His Leu Leu Arg Leu Thr
    210                 215                 220
```

```
Ala Asp Thr Arg Ala Ala Val Pro Leu Asp Pro Val Leu Asn Pro
225                 230                 235                 240

Gln Thr Asn Ala Pro Thr Pro Leu Gly Gly Ala Val Leu Arg Ala Thr
            245                 250                 255

Ser Pro Met His Met Gln Tyr Leu Arg Asn Met Gly Val Gly Ser Ser
            260                 265                 270

Leu Ser Val Ser Val Val Gly Gly Gln Leu Trp Gly Leu Ile Val
        275                 280                 285

Cys His His Gln Thr Pro Tyr Val Leu Pro Pro Asp Leu Arg Thr Thr
        290                 295                 300

Leu Glu Tyr Leu Gly Arg Leu Leu Ser Leu Gln Val Gln Val Lys Glu
305                 310                 315                 320

Ala

<210> SEQ ID NO 18
<211> LENGTH: 321
<212> TYPE: PRT
<213> ORGANISM: Artificial Sequence
<220> FEATURE:
<223> OTHER INFORMATION: synthetic infrared fluorescent protein (IFP),
      truncated bacteriophytochrome chromophore-binding
      domain from Deinococcus radiodurans (DrCDB),
      IFP1.2

<400> SEQUENCE: 18

Met Ser Arg Asp Pro Leu Pro Phe Phe Pro Pro Leu Tyr Leu Gly Gly
1               5                   10                  15

Pro Glu Ile Thr Thr Glu Asn Cys Glu Arg Glu Pro Ile His Ile Pro
            20                  25                  30

Gly Ser Ile Gln Pro His Gly Ala Leu Leu Thr Ala Asp Gly His Ser
        35                  40                  45

Gly Glu Val Leu Gln Val Ser Leu Asn Ala Ala Thr Phe Leu Gly Gln
    50                  55                  60

Glu Pro Thr Val Leu Arg Gly Gln Thr Leu Ala Ala Leu Leu Pro Glu
65                  70                  75                  80

Gln Trp Pro Ala Leu Gln Ala Ala Leu Pro Pro Gly Cys Pro Asp Ala
                85                  90                  95

Leu Gln Tyr Arg Ala Thr Leu Asp Trp Pro Ala Ala Gly His Leu Ser
            100                 105                 110

Leu Thr Val His Arg Val Gly Glu Leu Leu Ile Leu Glu Phe Glu Pro
        115                 120                 125

Thr Glu Ala Trp Asp Ser Thr Gly Pro His Ala Leu Arg Asn Ala Met
130                 135                 140

Phe Ala Leu Glu Ser Ala Pro Asn Leu Arg Ala Leu Ala Glu Val Ala
145                 150                 155                 160

Thr Gln Thr Val Arg Glu Leu Thr Gly Phe Asp Arg Val Met Leu Tyr
                165                 170                 175

Lys Phe Ala Pro Asp Ala Thr Gly Glu Met Ile Ala Glu Ala Arg Arg
            180                 185                 190

Glu Gly Leu His Ala Phe Leu Gly His Arg Phe Pro Ala Ser His Thr
        195                 200                 205

Pro Ala Gln Ala Arg Ala Leu Tyr Thr Arg His Leu Leu Arg Leu Thr
    210                 215                 220

Ala Asp Thr Arg Ala Ala Val Pro Leu Asp Pro Val Leu Asn Pro
225                 230                 235                 240

Gln Thr Asn Ala Pro Thr Pro Leu Gly Gly Ala Val Leu Arg Ala Thr
            245                 250                 255
```

```
Ser Pro Met His Met Gln Tyr Leu Arg Asn Met Gly Val Gly Ser Ser
            260                 265                 270

Leu Ser Val Ser Val Val Val Gly Gly Gln Leu Trp Gly Leu Ile Val
        275                 280                 285

Cys His His Gln Thr Pro Tyr Val Leu Pro Pro Asp Leu Arg Thr Thr
        290                 295                 300

Leu Glu Tyr Leu Gly Arg Leu Leu Ser Leu Gln Val Gln Val Lys Glu
305                 310                 315                 320

Ala

<210> SEQ ID NO 19
<211> LENGTH: 321
<212> TYPE: PRT
<213> ORGANISM: Artificial Sequence
<220> FEATURE:
<223> OTHER INFORMATION: synthetic infrared fluorescent protein (IFP),
      truncated bacteriophytochrome chromophore-binding
      domain from Deinococcus radiodurans (DrCDB),
      IFP1.3

<400> SEQUENCE: 19

Met Ser Arg Asp Pro Leu Pro Phe Phe Pro Pro Leu Tyr Leu Gly Gly
1               5                   10                  15

Pro Glu Ile Thr Thr Glu Asn Cys Glu Arg Glu Pro Ile His Ile Pro
            20                  25                  30

Gly Ser Ile Gln Pro His Gly Ala Leu Leu Thr Ala Asp Gly His Ser
        35                  40                  45

Gly Glu Val Leu Gln Val Ser Leu Asn Ala Ala Thr Phe Leu Gly Gln
    50                  55                  60

Glu Pro Thr Val Leu Arg Gly Gln Thr Leu Ala Ala Leu Leu Pro Glu
65                  70                  75                  80

Gln Trp Pro Ala Leu Gln Ala Ala Leu Pro Pro Gly Cys Pro Asp Ala
                85                  90                  95

Leu Gln Tyr Arg Ala Thr Leu Asp Trp Pro Ala Ala Gly His Leu Ser
            100                 105                 110

Leu Thr Val His Arg Val Gly Glu Leu Leu Ile Leu Glu Phe Glu Pro
        115                 120                 125

Thr Glu Ala Trp Asp Ser Thr Gly Pro His Ala Leu Arg Asn Ala Met
    130                 135                 140

Phe Ala Leu Glu Ser Ala Pro Asn Leu Arg Ala Leu Ala Glu Val Ala
145                 150                 155                 160

Thr Gln Thr Val Arg Glu Leu Thr Gly Phe Asp Arg Val Met Leu Tyr
                165                 170                 175

Lys Phe Ala Pro Asp Ala Thr Gly Glu Met Ile Ala Glu Ala Arg Arg
            180                 185                 190

Glu Gly Leu His Ala Phe Leu Gly His Arg Phe Pro Ala Ser His Thr
        195                 200                 205

Pro Ala Gln Ala Arg Ala Leu Tyr Thr Arg His Leu Leu Arg Leu Thr
    210                 215                 220

Ala Asp Thr Arg Ala Ala Ala Val Pro Leu Asp Pro Val Leu Asn Pro
225                 230                 235                 240

Gln Thr Asn Ala Pro Thr Pro Leu Gly Gly Ala Val Leu Arg Ala Thr
                245                 250                 255

Ser Pro Met His Met Gln Tyr Leu Arg Asn Met Gly Val Gly Ser Ser
            260                 265                 270

Leu Ser Val Ser Val Val Val Gly Gly Gln Leu Trp Gly Leu Ile Val
```

```
                275                 280                 285
Cys His His Gln Thr Pro Tyr Val Leu Pro Pro Asp Leu Arg Thr Thr
    290                 295                 300

Leu Glu Tyr Leu Gly Arg Lys Leu Ser Leu Gln Val Gln Val Lys Glu
305                 310                 315                 320

Ala

<210> SEQ ID NO 20
<211> LENGTH: 321
<212> TYPE: PRT
<213> ORGANISM: Artificial Sequence
<220> FEATURE:
<223> OTHER INFORMATION: synthetic infrared fluorescent protein (IFP),
      truncated bacteriophytochrome chromophore-binding
      domain from Deinococcus radiodurans (DrCDB),
      IFP1.4

<400> SEQUENCE: 20

Met Ser Arg Asp Pro Leu Pro Phe Phe Pro Pro Leu Tyr Leu Gly Gly
1               5                   10                  15

Pro Glu Ile Thr Thr Glu Asn Cys Glu Arg Glu Pro Ile His Ile Pro
                20                  25                  30

Gly Ser Ile Gln Pro His Gly Ala Leu Leu Thr Ala Asp Gly His Ser
        35                  40                  45

Gly Glu Val Leu Gln Val Ser Leu Asn Ala Ala Thr Phe Leu Gly Gln
50                  55                  60

Glu Pro Thr Val Leu Arg Gly Gln Thr Leu Ala Ala Leu Leu Pro Glu
65                  70                  75                  80

Gln Trp Pro Ala Leu Gln Ala Ala Leu Pro Pro Gly Cys Pro Asp Ala
                85                  90                  95

Leu Gln Tyr Arg Ala Thr Leu Asp Trp Pro Ala Ala Gly His Leu Ser
            100                 105                 110

Leu Thr Val His Arg Val Ala Glu Leu Leu Ile Leu Glu Phe Glu Pro
        115                 120                 125

Thr Glu Ala Trp Asp Ser Ile Gly Pro His Ala Leu Arg Asn Ala Met
    130                 135                 140

Phe Ala Leu Glu Ser Ala Pro Asn Leu Arg Ala Leu Ala Glu Val Ala
145                 150                 155                 160

Thr Gln Thr Val Arg Glu Leu Thr Gly Phe Asp Arg Val Met Leu Tyr
                165                 170                 175

Lys Phe Ala Pro Asp Ala Thr Gly Glu Met Ile Ala Glu Ala Arg Arg
            180                 185                 190

Glu Gly Met Gln Ala Phe Leu Gly His Arg Phe Pro Ala Ser His Thr
        195                 200                 205

Pro Ala Gln Ala Arg Ala Leu Tyr Thr Arg His Leu Leu Arg Leu Thr
    210                 215                 220

Ala Asp Thr Arg Ala Ala Ala Val Pro Leu Asp Pro Val Leu Asn Pro
225                 230                 235                 240

Gln Thr Asn Ala Pro Thr Pro Leu Gly Gly Ala Val Leu Arg Ala Thr
                245                 250                 255

Ser Pro Met His Met Gln Tyr Leu Arg Asn Met Gly Val Gly Ser Ser
            260                 265                 270

Leu Ser Val Ser Val Val Val Gly Gly Gln Leu Trp Gly Leu Ile Val
        275                 280                 285

Cys His His Gln Thr Pro Tyr Val Leu Pro Pro Asp Leu Arg Thr Thr
    290                 295                 300
```

```
Leu Glu Glu Leu Gly Arg Lys Leu Ser Gly Gln Val Gln Arg Lys Glu
305                 310                 315                 320

Ala

<210> SEQ ID NO 21
<211> LENGTH: 6
<212> TYPE: PRT
<213> ORGANISM: Artificial Sequence
<220> FEATURE:
<223> OTHER INFORMATION: synthetic hexahistidine tag, his6, his-tag

<400> SEQUENCE: 21

His His His His His His
1               5
```